US008889412B2

(12) United States Patent
Lim et al.

(10) Patent No.: US 8,889,412 B2

(45) Date of Patent: Nov. 18, 2014

(54) METHODS OF ENHANCING PLURIPOTENTCY

(75) Inventors: Bing Lim, Singapore (SG); Jianyong Han, Singapore (SG); Wai-Leong Tam, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/510,750

(22) PCT Filed: Nov. 18, 2010

(86) PCT No.: PCT/SG2010/000437

§ 371 (c)(1), (2), (4) Date: May 18, 2012

(87) PCT Pub. No.: WO2011/062559

PCT Pub. Date: May 26, 2011

(65) Prior Publication Data

US 2013/0102479 A1 Apr. 25, 2013

Related U.S. Application Data

(60) Provisional application No. 61/262,741, filed on Nov. 19, 2009.

(30) Foreign Application Priority Data

Feb. 6, 2010 (SG) ................................ 201000825-8

(51) Int. Cl.

*C12N 5/00* (2006.01)
*C12N 5/02* (2006.01)
*C12N 5/071* (2010.01)
*C12N 5/07* (2010.01)
*C12N 5/10* (2006.01)
*C12N 5/074* (2010.01)
*C12N 15/00* (2006.01)
*A01K 67/027* (2006.01)
*C12N 15/873* (2010.01)

(52) U.S. Cl.

CPC .............. *C12N 5/0696* (2013.01); *C12N 15/00* (2013.01); *C12N 2501/00* (2013.01); *C12N 2506/00* (2013.01); *A01K 67/0271* (2013.01); *C12N 15/873* (2013.01); *C12N 2501/60* (2013.01); *C12N 2501/602* (2013.01); *C12N 2501/603* (2013.01); *C12N 2501/604* (2013.01); *C12N 2510/00* (2013.01); *C12N 2799/027* (2013.01)

USPC ............ 435/377; 435/375; 435/366; 435/354

(58) Field of Classification Search

CPC ........... C12N 2506/00; C12N 2506/02; C12N 2506/03; C12N 2506/04; C12N 5/0696

USPC ........................................................ 435/377

See application file for complete search history.

(56) References Cited

PUBLICATIONS

Kim, 2009, Cell Stem Cell, 4:472-476, attached as pp. 1-8.*

Zhou, 2009, Cell Stem Cell, 381-384 and Supplemental data pp. 1-8.*

NIH; Stem Cells: Scientific Progress and Future Research Directions, Department of Health and Human Services, Chapter 1, pp. 14, Jun. 2001.*

Nakagawa 2008, Nature Biotechnology, 26:101-106.*

Yu (2007, Science, 318:1917-1920).*

International Search Report and Written Opinion for PCT/SG2010/000437 dated Feb. 24, 2011.

International Preliminary Report on Patentability for PCT/SG2010/000437 dated Sep. 22, 2011.

GenBank Accession No. NM_005996.3 May 17, 2004.

GenBank Accession No. NP_005987.3 May 17, 2004.

GenBank Accession No. NM_016569.3 May 17, 2004.

GenBank Accession No. NP_057653.3 May 17, 2004.

Takahashi et al., "Induction of Pluripotent Stem Cells from Mouse Embryonic and Adult Fibroblast Cultures by Defined Factors." *Cell*, 2006, vol. 126, pp. 663-676.

Han et al., "Tbx3 improves the germ-line competency of induced pluripotent stem cells." *Nature*, Feb. 25, 2010, vol. 463, pp. 1096-1101.

Pirity et al., "Tbx3: another important piece fitted into the pluripotent stem cell puzzle." *Stem Cell Research*, May 20, 2010, vol. 1(2), p. 12.

* cited by examiner

*Primary Examiner* — Valarie Bertoglio

(74) *Attorney, Agent, or Firm* — Choate, Hall & Stewart LLP; Charles E. Lyon

(57) ABSTRACT

We provide for the use of Tbx3 (GenBank Accession Number: NM_005996.3 (SEQ ID NO. 1), NP_005987.3 (SEQ ID NO. 2), NM_016569.3 (SEQ ID NO. 3), NP_057653.3 (SEQ ID NO. 4)) in a method of enhancing or inducing pluripotency in a cell such as a somatic cell. We describe a method of reprogramming a cell, the method comprising modulating the expression and/or activity of Tbx3 in the cell. The cell may become a pluripotent cell such as a stem cell. We further describe a method of causing a cell such as a somatic cell to display one or more characteristics of a pluripotent cell, the method comprising modulating the expression and/or activity of Tbx3 in the cell. The method may further comprise modulating the expression and/or activity of one or more, a combination of or all of Oct4, Sox2 and Klf4 in the cell.

3 Claims, 38 Drawing Sheets

FIGURE 4C

| Combination | iPS clones | Total number of fetus examined | GFP+ gonads (Percentage) | Contribution of GFP+ cells to gonads | | |
|---|---|---|---|---|---|---|
| | | | | >90% | 50-90% | <50% |
| OSK | 11 | 178 | 42 (23.6%) | 11 (26.2%) | 9 (21.4%) | 22 (52.4%) |
| OSE | 3 | 24 | 2 (12.5%) | 0 | 0 | 2 (100%) |
| OSKT | 13 | 209 | 73 (34.9%*) | 42 (57.5%*) | 21 (28.8%) | 10 (13.7%*) |

FIGURE 4E

| | iPS Line | Chimera | Total offspring per litter (Frequency of Black) | Percentage |
|---|---|---|---|---|
| OSK | #1 | 1 | 11(11); 4(4) | 100% |
| | | 2 | 10(0) | 0 |
| | #2 | 3 | 6(2); 10(4) | 37.5% |
| | | 4 | 12(0) | 0 |
| | | 5 | 8(0) | 0 |
| | #12 | 8 | 8(0); 10(0) | 0 |
| | #13 | 6 | 11(3); 3(1) | 28.5% |
| | | 7 | 5(0) | 0 |
| | #14 | 9 | 9(0) | 0 |
| OSE | #1 | 1 | 10(2); | 20% |
| | | 2 | 13(0); 9(0) | 0 |
| | #2 | 3 | 9(0) | 0 |
| | | 4 | 10(0) | 0 |
| | | 5 | 8(0); 10(0) | 0 |
| OSKT* | #6 | 1 | 13(13); 10(10) | 100% |
| | | 2 | 7(7) | 100% |
| | | 3 | 8(4); 12(5) | 45% |
| | #11 | 4 | 6(6); 9(9); 10(10) | 100% |
| | | 5 | 10(0) | 0% |
| | #12 | 6 | 6(6) | 100% |
| | #13 | 7 | 7(2) | 28.6% |
| | #14 | 8 | 7(0) | 0% |
| | #15 | 9 | 4(4); 7(7) | 100% |

OSKT Line #16 Week 1

OSKT Line #16 Week 2

OSKT Line #14 E19

OSKT Line #14 E19

FIGURE 10

Vector (pLenti6-UBC)
Tbx3 (pLenti6-UBC)
Tbx3
Actin

FIGURE 11

| | Isolated GFP$^+$ colony number | Stable GFP$^+$ line | Percentage |
|---|---|---|---|
| OSK + c-Myc+ Tbx3 | 36 | 12 | 33.3% |
| OSK + cMyc | 36 | 18 | 50% |
| OSK | 36 | 33 | 91.6% |
| OSK + Tbx3 | 36 | 32 | 88.8% |

Teratoma (H&E stain)

METHODS OF ENHANCING PLURIPOTENTCY

PRIORITY CLAIM

This application is a national phase application under 35 U.S.C. §371 of PCT International Application No. PCT/SG2010/000437 (published PCT Application No. WO 2011/062559 A1), Filed Nov. 18, 2010, which claims priority from Singapore Patent Application No. 201000825-8, filed Feb. 6, 2010 and from U.S. Provisional Application No. 61/262741 filed Nov. 19, 2009, the contents of each of which are hereby incorporated by reference in their entirety for all purposes.

FIELD

The present invention relates to the fields of development, cell biology, molecular biology and genetics. More particularly, the invention relates to methods and compositions for reprogramming somatic cells, deriving stem cells from somatic cells and inducing pluripotency in somatic cells.

BACKGROUND

Sequence Listing

In accordance with 37 CFR §1.52(e)(5), a Sequence Listing in the form of a text file (entitled "Sequence Listing$_{13}$ST25.txt, "created on Dec. 7, 2012, and 96 kilobytes in size) is incorporated herein by reference in its entirety.

ESCs are pluripotent and can self-renew indefinitely. These properties, conferred by a set of core factors, determine the ESC identity.

It has been shown that adult somatic cells can be reprogrammed to resemble ESCs when key transcription factors are introduced. Induced pluripotent stem (iPS) cells may be obtained through the introduction of defined factors into somatic cells. This suggests that the shuffling between alternate cellular identities is largely defined by unique sets of regulatory molecules present in different cell types.

The induction of pluripotent stem cells can be achieved with the viral transduction of a few genes in both mouse and human cells, albeit at low efficiency. Supplementations with chemical compounds such as inhibitors to DNA methyltransferase, histone deacetylase, histone methyltransferase, mitogen-activated protein kinase and glycogen synthase kinase-3, has been reported to improve the reprogramming efficiency[2-5].

Recently, the generation of iPS cells has been achieved without viral vectors. Repeated transfection of plasmids over-expressing OSK+c-Myc (OSKC) resulted in iPS cells without exogenous DNA integration[6]. The combination of Oct4, Sox2 and Klf4 (OSK) constitutes the minimal requirement for generating iPS cells from mouse embryonic fibroblasts (MEFs).

Induced pluripotent stem (iPS) cells are thought to resemble embryonic stem cells (ESCs) based on global gene expression analyses. While ESC-like iPS cells can be routinely obtained with these methods, very few studies have carefully examined their germ-line contribution and transmission frequency.

Thus, although iPS cells have a distinct morphology and express molecular markers very similar to ESCs, their ability and degree of contribution to the chimera appears highly varied[4,7,9]. This suggests that iPS cells do not completely resemble ESCs[10], and there is marked disparity in the quality of different iPS cell lines.

Specifically, the ability and efficiency of these iPS cell clones in contributing to chimerism, colonization of germ tissues, and most importantly, germ-line transmission and life-birth from iPS cells generated with tetraploid complementation has not been established.

There is therefore a need in the art for other factors, in addition to the basal requirements of OSK, to improve the quality of reprogrammed iPS cells as defined by their capacity for high germ-line competency.

SUMMARY

According to a 1$^{st}$ aspect of the present invention, we provide for use of Tbx3 (GenBank Accession Number: NM_005996.3(SEQ ID NO. 1), NP_005987.3(SEQ ID No. 2), NM_016569.3(SEQ ID NO. 3), NP_057653.3(SEQ ID NO 4)) in a method of inducing or enhancing pluripotency in a cell such as a somatic cell.

There is provided, according to a 2$^{nd}$ aspect of the present invention, a method of reprogramming a cell, the method comprising modulating the expression and/or activity of Tbx3 (GenBank Accession Number: NM_005996.3(SEQ ID NO. 1), NP_005987.3(SEQ ID NO. 2), NM_016569.3(SEQ ID NO. 3), NP_057653.3(SEQ ID NO. 4)) in the cell.

The method or use may be such that the cell becomes a pluripotent cell such as a stem cell.

We provide, according to a 3$^{rd}$ aspect of the present invention, a method of causing a cell such as a somatic cell to display one or more characteristics of a pluripotent cell, the method comprising modulating the expression and/or activity of Tbx3 (GenBank Accession Number: NM_005996.3(SEQ ID NO. 1), NP_005987.3(SEQ ID NO. 2), NM_0165693 (SEQ ID NO. 3), NP_057653.3(SEQ ID NO. 4)) in the cell.

The use or method may further comprise modulating the expression and/or activity of one or more, a combination of or all of Oct4, Sox2 and Klf4 in the cell, optionally without the introduction of c-Myc into the cell.

The method or use may be such that the cell displays one or more characteristics of a pluripotent cell, such as expression of one or more pluripotent markers, such as Oct4, Nanog, Gdf3, Dppa4 and Tbx3 (GenBank Accession Number: NM_005996.3(SEQ ID NO. 1), NP_005987.3(SEQ ID NO. 2), NM_016569.3(SEQ ID NO. 3), NP_057653.3(SEQ ID NO. 4)).

The use or method may be such that the cell is capable of contributing to chimerism such as when introduced into an embryo of different genetic background.

The use or method may be such that the cell is able to colonise germ tissue, such as by germ cell contribution to gonads.

The use or method may be such that the cell is capable of colonising germ tissue with a high germ-line competency or at a high germ-line transmission frequency.

The use or method may be such that the cell is capable of generating full-term live-born progeny via tetraploid blastocyst complementation.

As a 4$^{th}$ aspect of the present invention, there is provided Tbx3 (GenBank Accession Number: NM_005996.3(SEQ ID NO. 1), NP_005987.3(SEQ ID NO. 2), NM_016569.3(SEQ ID NO. 3), NP_057653.3(SEQ ID NO. 4)) for use in a method of inducing pluripotency in a cell, reprogramming a cell, or causing a cell to express one or more one or more characteristics of a pluripotent cell, in which the cell for example comprises a somatic cell.

The use or method may be such that the cell comprises a mammalian cell such as a mouse cell or a human cell.

We provide, according to a $5^{th}$ aspect of the present invention, a method of obtaining a stem cell line, the method comprising performing a method as set out above and deriving a cell line therefrom.

The present invention, in a $6^{th}$ aspect, provides an induced, reprogrammed, pluripotent or a stem cell or cell line obtainable by a method as described.

In a $7^{th}$ aspect of the present invention, there is provided a method of identifying a molecule capable of enhancing differentiation of a cell, the method comprising performing a method as set out above in the presence of a candidate molecule and detecting a reduced induction of pluripotency by the cell, reduced reprogramming of the cell or reduced expression of one or more characteristics of a pluripotent cell by the cell, compared to in the absence of the candidate molecule.

According to an $8^{th}$ aspect of the present invention, we provide a method of identifying a molecule capable of enhancing differentiation of a cell, the method comprising obtaining a induced, reprogrammed, pluripotent or a stem cell by a method as set out above, exposing the cell to a candidate molecule and detecting differentiation of the cell.

We provide, according to a $9^{th}$ aspect of the invention, a method of identifying a molecule capable of enhancing or inducing the pluripotency of a cell, the method comprising performing a method as set out above in the presence of a candidate molecule and detecting an increased induction of pluripotency by the cell, increased reprogramming of the cell or increased expression of one or more characteristics of a pluripotent cell by the cell, compared to in the absence of the candidate molecule.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA Methods in Enzymology*, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

BRIEF DESCRIPTION OF THE FIGURES

FIG. 1A. Modified ESCs with Nanog over-expression (OE) or Tcf3 RNAi were fused with MEFs to generate tetraploid ESC/MEF hybrids resistant to neomycin and puromycin.

FIG. 1B. Nanog OE, Tbx3 OE and Tcf3 RNAi enhanced cell fusion-mediated reprogramming of MEFs. Representative examples illustrate the emergence of ESC/MEF hybrid colonies. Control ESC fusion with MEFs resulted in an average of one per experiment whereas Tcf3 RNAi, Nanog OE or Tbx3 OE ESCs produced numerous hybrid clones after fusion.

FIG. 1C. Nanog OE ESCs were efficient in reprogramming MEFs, generating 13 colonies, followed by Tcf3 RNAi (10) and Tbx3 OE (4.5). The numbers represent the average of four independent fusion experiments. * denotes significantly different from vector, $^+$ denotes significantly different from control shRNA.

FIG. 1D. The heat-map shows all genes which were increased in treated ESCs compared to controls. Tbx3 was among the most highly up-regulated genes in Nanog OE and Tcf3 RNAi ESCs. The left-most column in red indicates direct gene targets of Nanog or Tcf3 based on the ChIP-PET[29] and ChIP-chip[14] databases respectively.

FIG. 1E. RNAi knockdown of Tbx3 in ESCs led to a loss of self-renewal and induced differentiation.

FIG. 1F. Enrichment of Tcf3 and Nanog occupancy on the Tbx3 gene, as measured by ChIP-qPCR.

FIG. 2A. OSKC and OSKCT induced ~300 ESC-like colonies (per $5\times10^4$ MEFs) with ~10% expressing GFP. Under the same experimental conditions, OSKT induced an average of 38 compared to 26 ESC-like colonies from OSK, with 89% and 74% GFP activation respectively. Colonies were assessed and counted on day 16. Data represents the average of three independent transduction experiments. * denotes significantly different from OSK; $p<0.05$.

FIG. 2B. OSK and OSKT iPS cell clones showed tight, domed-shaped ESC-like morphology and uniform GFP expression throughout the colony, whereas OSKC clones appeared as flattened, transformed cells with sparse GFP expression. Scale bar=100 μm.

FIG. 2C. OSKT induced the activation of Oct4-GFP transgene in iPS derived from primary MEFs at 9-10 days post-infection, whereas OSK and OSKC combinations required 14 days observed in four independent transduction experiment.

FIG. 2D. PCR analysis confirmed the genomic integration of over-expression plasmids for specific factors in iPS cells generated with the different combinations.

FIG. 2E. OSKT iPS cells expressed typical ESC proteins detected by antibodies specific to Nanog, Sox2, SSEA1, and by alkaline phosphatase activity. Scale bar=100 μm.

FIG. 3A. Hierarchical clustering of global expression profiling showed that OSKT and OSK clones are more similar to wild-type ESCs than OSE, but indistinguishable from each other based on correlation coefficient ($R^2=0.94$). $R^2$ value was obtained from the average individual gene signal intensity of all iPS clones in each combination and compared against R1 ESCs. The independent transduction experiments where the clones were isolated are denoted as A, B, C, and D.

FIG. 3B. Analysis of individual ESC-associated gene profiles revealed a subset that could distinguish OSKT from OSK-derived iPS cells. 'Distinguishing' ESC genes were expressed at levels similar between OSKT and ESCs but significantly lower in OSK. The majority of other ESC-associated genes were 'non-distinguishing' and present at levels similar between both OSKT and OSK. * denotes significantly different from OSKT; + denotes significantly different from ESC; p<0.05. Changes in gene expression based on microarray were confirmed with qPCR (Figure S9).

FIG. 4A to FIG. 4G are figures showing that OSKT iPS cells show enhanced germ-line contribution and transmission.

FIG. 4A. Injection of $GFP^+$ iPS cells into 4-8 cell morula (top panel), followed by in vitro maturation into blastocysts and re-implantation into surrogates. $GFP^+$ cells were localized specifically to the ICM (bottom panel).

FIG. 4B. Representative photos showing the quantitative contribution and spatial distribution of $GFP^+$ cells generated with different reprogramming factor combinations in the gonads of chimeric E13.5 embryos.

FIG. 4C. Tabulation comparing the contribution of $GFP^+$ iPS cell-derived germ cells to the gonads of chimeric fetuses and their spatial distribution with different combinations of factors. OSKT iPS cells were most effective at colonizing the gonads, compared to OSK and OSE iPS cells. * denotes significantly different from OSK, p<0.01. Eleven independent sets of microinjections were performed for OSK versus OSKT comparison.

FIG. 4D. Representative photos showing the contribution of iPS cells to chimeric coat and the production of $F_2$ offspring after crossing with albino mice. Black offspring is indicates the germ-line transmission of iPS cells.

FIG. 4E. Table summarizing the germ-line transmission frequency for iPS cells generated with the different combination of factors. For each combination, between two to six iPS cell lines were used to obtain live chimeras, of which, at least one male from each combination were crossed with an albino female to determine the frequency of black $F_2$. * denotes significantly different from OSK and OSE, p<0.005 and p<0.001 respectively.

FIG. 4F. Two OSKT iPS cell lines were tested for their ability to generate live animals from tetraploid complementation. Two fetuses from an initial 33 tetraploid complementation generated embryos were obtained through C-section at E19 for OSKT #14 due to suspected uterine regression of the surrogate female. With OSKT #16, ten live births were obtained from 50 embryos. Eight survived on day 1, five on day 2, and three by week 1. One overweight pup died before week 2, with two remaining mice surviving past two months.

FIG. 4G. Co-occurrence of transcription factor (TF) groups within the multiple transcription factor-bound loci. Colors in the heat-map reflect the colocalization frequency of each pair of TFs (yellow means more frequently colocalized, red means less).

FIG. 10 is a diagram showing Western blot analysis showing the over-expression of Tbx3 from pLenti6-UBC and pMXs plasmids in HEK293T cells 48 h after infection.

FIG. 11 is a diagram showing a summary of iPS cell line isolation. A total of 36 iPS cell lines, from transduction experiment sets A and B, showing reactivation of the Oct4-GFP transgene were isolated for each combination of reprogramming factors. These were expanded and propagated for an average of six passages before microarray analyses and validation of in vivo developmental potential. The combinations OSK and OSKT produced stable iPS cell lines at ~90% efficiency whereas the efficiencies for deriving iPS lines were 33.3% for OSKCT and 50% for OSKC.

[CBA-Tg(Pou5f1-EGFP)$_2$Mnn/J]. Induced-PS cells were injected into the 4-8 cell embryos of albino mice, maturated into blastocysts which contained GFP$_+$ cells in the inner cell mass, and transplanted into pseudopregnant surrogate mice. At E13.5, half the mice were sacrificed to assess the contribution of iPS cells to the gonads of chimeras. At this stage, Oct4 would be reactivated solely in germ cells. Live chimeras (F$_1$) were obtained from the remaining surrogate mice, and subsequently bred with albino mice. F$_2$ offspring include albinos and heterozygous mice which are black. Black F$_2$ generation indicates the transmission of at least one allele (specifying coat color) and chromosomes from iPS cells.

FIG. 15 is a diagram showing the contribution of iPS cells to the gonads of chimeras. We assessed the contribution of iPS cells to the testes and ovaries of E13.5 chimeras derived from the injection of iPS cells to wild-type embryos. An arbitrary reference for the percentage distribution of GFP cells within each gonad was set at >90%, 50-90% and <50%, based on visual assessment. Only gonads with GFP$_+$ iPS-derived germ cell contribution for each combination are shown.

Figure 16:
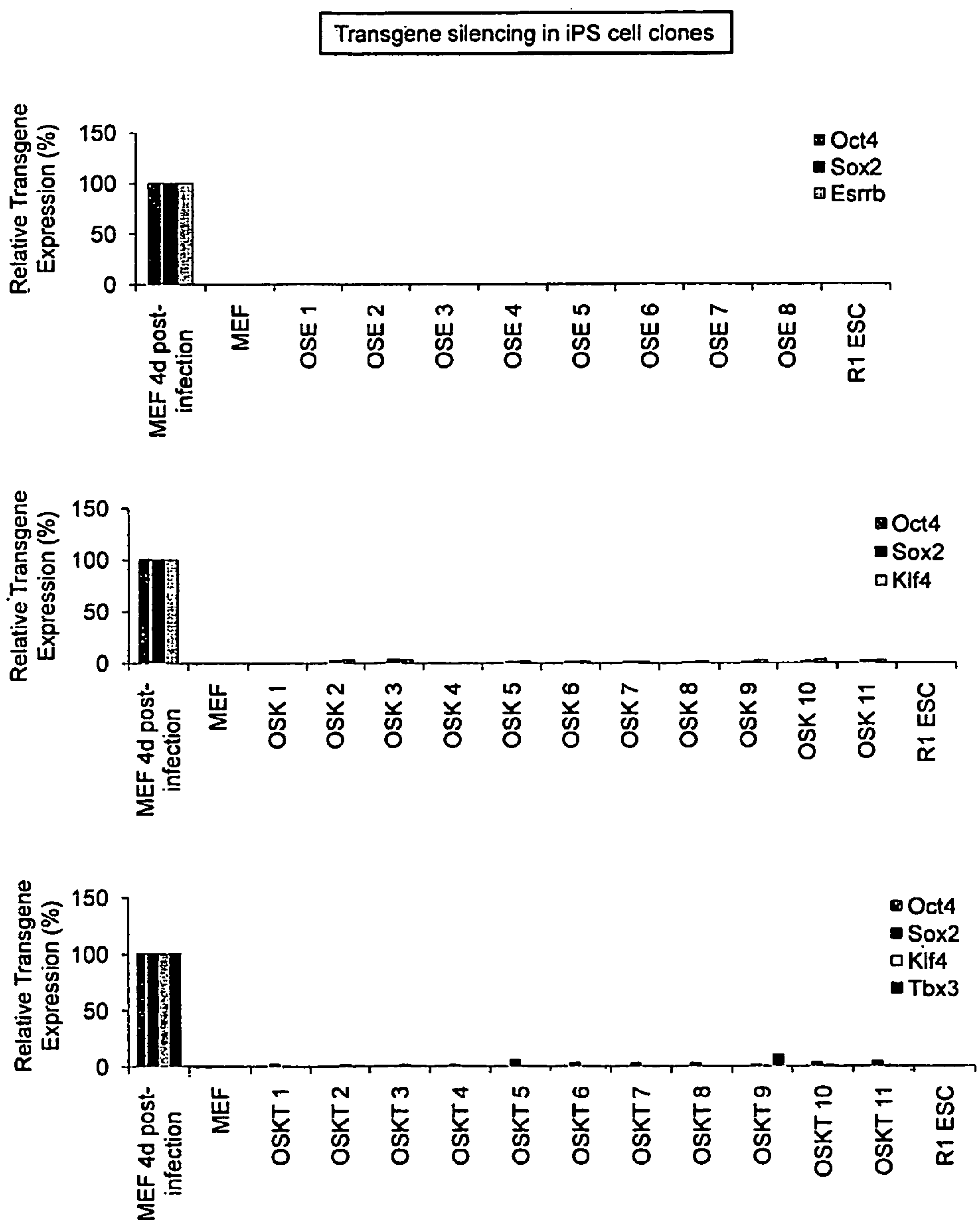

FIG. 16 is a diagram showing silencing of integrated transgenes in iPS cells. Four days after retroviral infection of MEFs with reprogramming factors, expression of the exogenous factors can be detected with qPCR primers specific to the transgenes. In fully reprogrammed iPS cell clones, the expression of transgenes could not be detected. n=3 technical replicates for each iPS cell clone.

Figure 17:
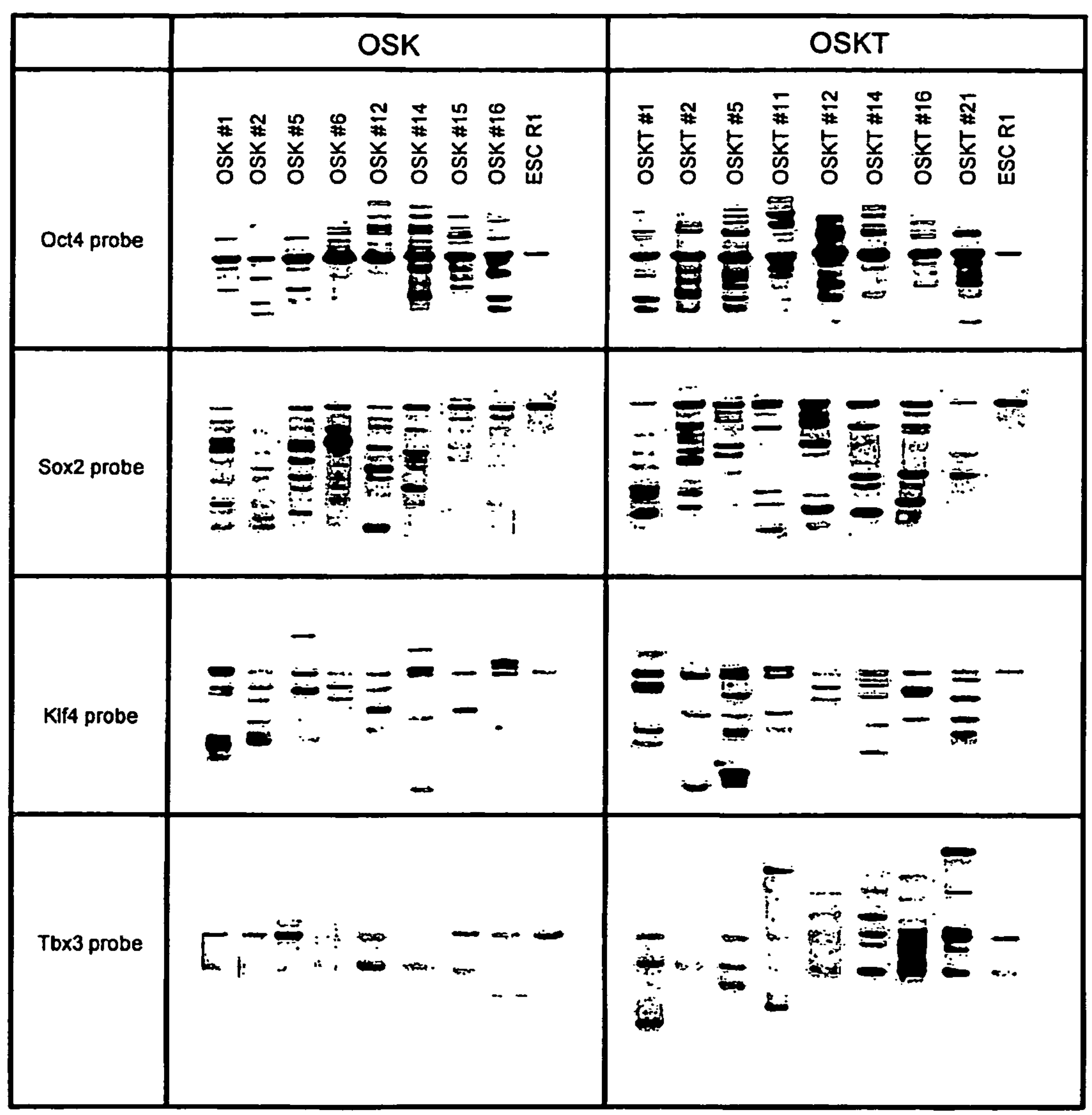

FIG. 17 is a diagram showing Southern hybridization analysis reveals multiple integrations of the Oct4, Sox2 and Klf4 transgenes in both OSK and OSKT clones. The frequencies of integrations, appeared similar between various clones derived with both combinations. Tbx3 integration was only detected in the OSKT clones at varying frequencies.

FIG. 18 is a diagram.

Figure 19:
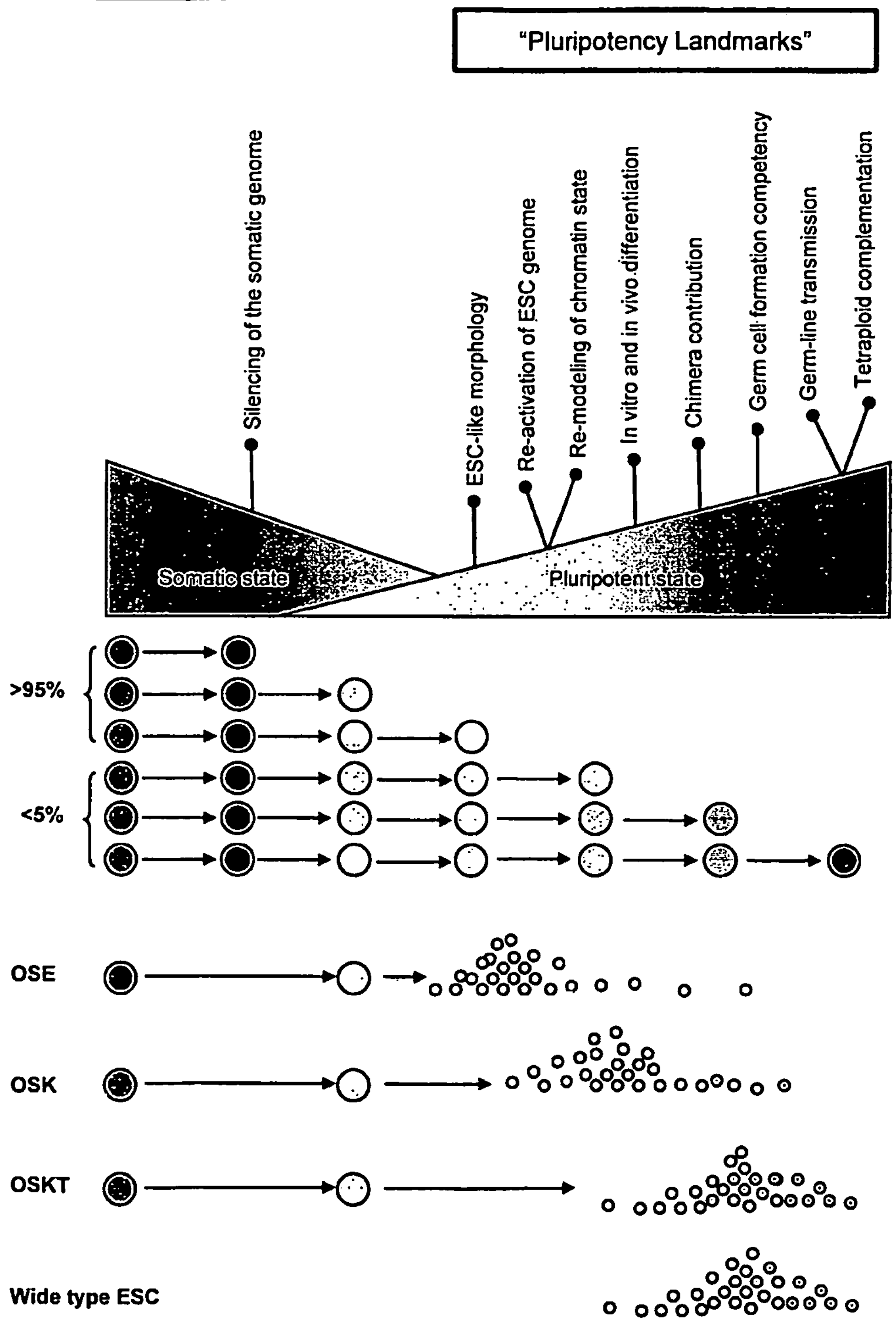

FIG. 19 is a diagram showing a model of "pluripotency landmarks" that can be employed to assess the reprogramming progress of the somatic genome to full developmental competency. The use of different factor combinations results in the generation of iPS populations and clones with markedly different developmental potentials centered upon progressive "landmarks" of pluripotency. The addition of Tbx3 to the existing reprogramming factors increases the probabilistic frequency of iPS cells that attains a pluripotent state equivalent or closest to ESCs within the entire population of reprogrammed cells.

DETAILED DESCRIPTION

Enhancing Pluripotency with Tbx3

We have now identified Tbx3 as a transcription factor that significantly improves the quality of iPS cells. Specifically, we establish that Tbx3 is capable of enhancing the pluripotency of cells such as stem cells.

As demonstrated in the Examples, induced-PS cells generated with Oct4, Sox2 and Klf4 (OSK)+Tbx3 (i.e., OSKT) are superior in both germ cell contribution to the gonads and germ-line transmission frequency. In particular, we find that global gene expression profiling could not distinguish between OSK and OSKT iPS cells.

We further show in the Examples that genome-wide ChIP-sequencing analysis of Tbx3 binding sites in ESCs suggests that Tbx3 regulates pluripotency-associated and reprogramming factors, in addition to sharing many common downstream regulatory targets with Oct4, Sox2, Nanog and Smad1.

We therefore describe generally methods of enhancing or inducing pluripotency of cells such as somatic cells or stem cells (including induced pluripotent stem cells). We describe methods of inducing pluripotency in such cells. We describe methods for preparing stem cells such as induced pluripotent stem cells.

Our methods rely on the up-regulation of activity or expression, or both, of a reprogramming factor including Tbx3. In particular, we describe a method of preparation of enhancing or inducing pluripotency of cells such as somatic cells or stem cells (including induced pluripotent stem cells) in the presence of one or more reprogramming factors and Tbx3. Our methods may be used with or without using c-Myc, which is a suspected tumorigenic factor.

We have determined that pluripotency of cells may be increased and induced pluripotent stem cells may be efficiently prepared by introduction of nuclear reprogramming inducing genes, such as an Oct family gene, a Klf family gene, a Sox family gene (or any combination of the above) into somatic cells in the presence of Tbx3.

We therefore describe a method of preparing induced pluripotent stem cells and a method of enhancing the pluripotency of stem cells, comprising nuclear reprogramming with a nuclear reprogramming factor in the presence of Tbx3. The Tbx3 may have a property of providing a higher nuclear reprogramming efficiency in the presence of the Tbx3 than in the absence thereof.

For example, our method may comprise expressing Tbx3 in embryonic stem cells at a higher level than in somatic cells. Our method may comprise the feature that Tbx3 has a property of providing a higher nuclear reprogramming efficiency in the presence of the Tbx3 than in the absence of Tbx3.

Our method may comprise the feature that the nuclear reprogramming is performed in the presence of increased levels of Tbx3 as compared to the levels present in the somatic cell prior to nuclear reprogramming.

The cells suitable for use in the methods and compositions described here may be derived from any suitable source. Examples include human, mouse, rat, cattle, sheep, horse, monkey, and hamster cells, such as somatic or stem cells from human or mouse, for example somatic or stem cells from human.

The somatic cells may comprise human embryonic cells, or adult human-derived somatic cells. The somatic cells may be specific to one or more individuals, such as a collection of somatic cells from a group of individuals or a population.

The somatic cells may comprise somatic cells collected from a patient.

We further provide for stem cells or cells in which pluripotency has been enhanced, including induced pluripotent stem cells, which may be made by the methods and compositions described here. We further provide for somatic cells obtained by inducing differentiation from such cells. We further provide for a therapy (which may be termed a stem cell therapy) comprising introducing or transplanting such cells into a patient.

We also describe a therapy in which somatic cells are introduced or transplanted into a patient. Such somatic cells may be obtained by inducing differentiation from cells such as induced pluripotent stem cells that are obtained according to the methods described here. The source somatic cells may be isolated and collected from a patient.

We also describe a method for evaluation of physiological effect or toxicity of a compound, a drug, or a toxic agent, with use of various cells obtained by inducing differentiation from cells in which pluripotency is enhanced, such as induced pluripotent stem cells, that are obtained by a method described in this document.

We describe a method for enhancing or inducing pluripotency of cells such as somatic cells or stem cells (including induced pluripotent stem cells), such as a method of preparing induced pluripotent stem cells, which uses Tbx3 expressed in embryonic stem cells at a higher level than in somatic cells, and having a property of providing a higher nuclear reprogramming efficiency in the presence of the Tbx3 than in the absence thereof.

We describe a nuclear reprogramming method of somatic cells which uses Tbx3 expressed in embryonic stem cells at a higher level than in somatic cells, and having a property of providing a higher nuclear reprogramming efficiency in the presence of the Tbx3 than in the absence of Tbx3.

The methods described here comprise the use of Tbx3 expressed in embryonic stem cells at a higher level than in somatic cells (e.g., the Tbx3 may be expressed at levels which are higher in the ES cell as compared to the ES cell which has differentiated or which has begun differentiating such as determined by RT-PCR or Nerthem blot analysis), and having a property of providing a higher nuclear reprogramming efficiency in the presence of the Tbx3 than in the absence thereof, for enhancing or inducing pluripotency of cells such as somatic cells or stem cells (including induced pluripotent stem cells) or for the preparation of induced pluripotent stem cells.

We describe methods relating to the use of Tbx3 expressed in embryonic stem cells at a higher level than in somatic cells, and having a property of providing a higher nuclear reprogramming efficiency in the presence of the Tbx3 than in the absence thereof, for nuclear reprogramming of somatic cells. In other words, nuclear reprogramming, and thus, induced pluripotent stem cell production or enhancement of pluripotency, may be performed in, the presence of Tbx3 and in the absence of Tbx3.

The nuclear reprogramming may also be performed in the presence of various amounts and/or forms sush as isoforms of Tbx3 (as described elsewhere in this document), such that, for example, the efficiency of the nuclear reprogramming is increased when the level of the Tbx3 is increased in the somatic cell prior to nuclear reprogramming.

We also describe methods comprising the use of Tbx3 having a property of providing a higher nuclear reprogramming efficiency in the presence of the Tbx3 than in the absence thereof, for enhancing or inducing pluripotency of cells such as somatic cells or stem cells (including induced pluripotent stem cells) such as for the preparation of induced pluripotent stem cells.

For example, the presence of added Tbx3 can provide the formation of an induced pluripotent stem cell as compared to the lack of formation in the absence of the Tbx3. Also, for example when nuclear reprogramming is performed on the same number of somatic cells in the presence of a nuclear reprogramming factor containing the same components in the same concentrations with and without addition of Tbx3, increased efficiency can be observed when a greater number of induced pluripotent stem cells are generated in the sample (or when a greater number of cells display pluripotentcy characteristics) which comprises the addition of Tbx3 than in the sample without the addition of Tbx3.

In another example, increased efficiency of induced pluripotent stems cell production may also be achieved with increased amounts of Tbx3 as compared to Tbx3 amounts present in the somatic cell prior to nuclear reprogramming.

Nuclear Reprogramming Factors

Our methods rely on exposing a cell such as a somatic cell, stem cell or induced pluripotent stem cell, to one or more nuclear reprogramming factors (such as a combination of these) in the presence of Tbx3.

The nuclear reprogramming factor may comprise either a single substance or a combination of a plurality of substances, which has nuclear reprogramming activity.

Nuclear reprogramming activity may be assayed or detected by a number of methods known in the art, such as those disclosed in International Publication No. WO2005/80598 A1. This document further describes methods of screening nuclear reprogramming factors, and any molecules detected in such a screening method or which are determined to be positive for nuclear reprogramming activity may be used in the methods and compositions described in this document for preparing stem cells or increasing: their pluripotentcy.

Those skilled in the art are able to screen a nuclear reprogramming factor for use in the methods and compositions described here by referring to the above publication. In addition, the nuclear reprogramming factor can also be confirmed by using a method in which appropriate modification or alteration has been made in the above screening method.

The nuclear reprogramming factor may comprise a single gene product, i.e., the expression product of a single gene. It may alternatively or in addition comprise a combination of gene products of a number of genes such as a plurality of genes, each of which may be deemed positive for nuclear reprogramming factor activity by a suitable assay, such as that disclosed in International Publication No. WO2005/80598 A1.

The nuclear reprogramming as described in the methods and compositions described here may comprise nuclear reprogramming with the nuclear reprogramming factor by introducing the relevant substance as assayed as having nuclear reprogramming activity (including a plurality of substances such as a gene or genes), as determined above, into a cell such as a somatic cell.

The gene or genes or substance or substances may also be introduced into a cell such as a stem cell, such as an induced pluripotent stem cell. Doing so may cause the cell to become a stem cell, where it is somatic, or display one or more characteristics or activities of a stem cell. Our methods may, alternatively or in addition, increase or enhance the pluripotency of a stem cell such as an induced pluripotent stem cell.

The substance having nuclear reprogramming activity may be introduced into a cell such as a somatic cell or stem cell or induced pluripotent stem cell by any means suitable for the situation, and in any suitable form. For example, the substance having nuclear reprogramming activity may be introduced into the cell in the form of a recombinant vector.

For example, the substance with nuclear reprogramming activity may comprise a gene, and the gene may be contained in a recombinant vector which is introduced into a cell such as a somatic cell or stem cell or induced pluripotent stem cell.

Combinations of Nuclear Reprogramming Factors

Examples of the combination of genes encoding reprogramming factors are disclosed in International Publication No. WO2007/069666 A1 and its family member U.S. patent application Ser. No. 12/213,035 and U.S. patent application Ser. No. 12/289,873, filed Nov. 6, 2008, entitled "Nuclear Reprogramming Factor and Induced Pluripotent Stem Cells" which are incorporated by reference herein in their entireties.

Those skilled in the art are able to appropriately select a gene that may be used for the methods described here by referring to the above publication. In addition, other examples of the combinations of genes encoding reprogramming factors are disclosed, for example, in Yu et al., Science 318:1917-20, 2007, incorporated by reference herein in its entirety.

Accordingly, those skilled in the art are able to understand the variety of the combination of genes encoding reprogramming factors, and are able to employ an appropriate combination of genes in the methods described here, which combination is not disclosed in International Publication No. WO2007/069666 A1 or Yu et al., Science 318:1917-20, 2007, by using the screening method of nuclear reprogramming factor described in International Publication No. WO2005/80598 A1.

Examples of the gene encoding a reprogramming factor that can be used for the methods described here can include: one or more gene(s) selected from an Oct family gene, a Klf family gene, a Sox family gene, a Myc family gene, a Lin family gene, and a Nanog gene; such as one or more gene(s) selected from an Oct family gene, a Klf family gene, a Sox family gene, a Lin family gene, and a Nanog gene, and excluding a Myc family gene; for example a combination of two genes; such as a combination of three genes; for example a combination of four genes.

Regarding the Oct family gene, Klf family gene, Sox family gene, and Myc family gene, specific examples of these family genes are described in International Publication No. WO2007/069666 A1. Regarding the Lin family gene, those skilled in the art are able to extract the family gene in a similar way. Examples of the Lin family genes include, for example, Lin28 and Lin28b. The NCBI accession numbers of Lin28 are NM 145833 (mouse; SEQ ID NO. 16) and NM 024674 (human; SEQ ID NO. 17). The NCBI accession numbers of Lin28b are NM 001031772 (mouse; SEQ ID NO. 18) and NM 001004317 (human; SEQ ID NO. 19).

Low Molecular Weight Compounds

In addition, reprogramming factor(s) encoded by one or more gene(s) selected from an Oct family gene, a Klf family gene, a Sox family gene, a Myc family gene, a Lin family gene, and a Nanog gene, may be substituted by, for example a cytokine, or one or more other low molecular weight compound(s) in some cases.

Examples of such low molecular weight compound(s) can include low molecular weight compounds having an enhancing action on the expression of one or more gene(s) selected from an Oct family gene, a Klf family gene, a Sox family gene, a Myc family gene, a Lin family gene, and a Nanog gene. Those skilled in the art are able to readily screen such low molecular weight compound(s).

Specific combinations of genes are as follows: (a) a combination of two genes comprising an Oct family gene and a Sox family gene; (b) a combination of three genes comprising an Oct family gene, a Klf family gene, and a Sox family gene; (c) a combination of four genes comprising an Oct family gene, a Sox family gene, a Lin family gene, and a Nanog gene; (d) a combination of two genes comprising an Oct family gene and a Klf family gene; and (e) a combination of three genes comprising an Oct family gene, a Klf family gene, and a Myc family gene. However, these combinations are not to be considered as limiting.

All of these genes are commonly present in mammals, including human. In order to use the above genes according to the methods and compositions described here, genes derived from any mammal (for example, derived from a mammal such as human, mouse, rat, cattle, sheep, horse, and monkey) can be employed.

In addition, it is also possible to use a wild type gene product, as well as mutant gene products in which several amino acids (for example 1 to 10 amino acids such as 1 to 6 amino acids, such as 1 to 4 amino acids, for example 1 to 3 amino acids, for example 1 or 2 amino acids) have been substituted, inserted, and/or deleted, and which have comparable equivalent functions to those of the wild type gene product.

For example, as to the c-Myc gene product, a stable type variant, e.g., (T58A) and the like may also be used as well as the wild type. The same principle can be applied to other gene products.

Immortalising Genes

In addition to the above genes, a gene encoding a factor which induces immortalization of cells may also be combined. As disclosed in International Publication No. WO2007/069666 A1, for example, one or more gene(s) selected from a TERT gene, and following genes: SV40 Large T antigen, HPV16 E6; HPV16 E7, and Bmi1, can be either solely used or jointly used, in an appropriate combination.

Specific other combinations are as follows, for example: (e) a combination of four genes comprising an Oct family gene, a Klf family gene, a Sox family gene, and a TERT gene; (f) a combination of four genes comprising an Oct family gene, a Klf family gene, a Sox family gene, and a SV40 Large T antigen gene; and (g) a combination of five genes comprising an Oct family gene, a Klf family gene, a Sox family gene, a TERT gene, and a SV40 Large T antigen gene. The Klf family gene may be omitted from the above combinations.

Other Genes

Further, in addition to the above genes, one or more gene(s) selected from Fbx15, ERas, ECAT15-2, Tell, and β-catenin may be combined, and/or one or more gene(s) selected from ECAT1, Esg1, Dnmt3L, ECAT8, Gdf3, Sox15, ECAT15-1, Fthl17, Sal14, Rex1, UTF1, Stella, Stat3, and Grb2 may also be combined. These combinations are specifically described in International Publication. No. WO2007/069666 A1.

Other combinations of genes are as follows: (1) a combination of two genes comprising Oct3/4 and Sox2; (2) a combination of three genes comprising Oct3/4, Klf4, and Sox2; (3) a combination of four genes comprising Oct3/4, Sox2, Lin28, and Nanog; (4) a combination of four genes comprising Oct3/4, Sox2, TERT, and SV40 Large T antigen gene; (5) a combination of five genes comprising Oct3/4, Klf4, Sox2, TERT, and SV40 Large T antigen gene; (6) a combination of two genes comprising Oct3/4 and Klf4; (7) a combination of three genes comprising Oct3/4, Klf4, and c-Myc; and (8) a combination of four genes comprising Oct3/4, Sox2, Klf4, and c-Myc. However, these combinations are not to be considered as limiting.

The factors including the gene products as mentioned above may also be combined with one or more gene product(s) of gene(s) selected from: Fbx15, Nanog, ERas, ECAT15-2, Tell, and β-catenin. Further, these factors may also be combined with one or more gene product(s) of gene(s) selected from: ECAT1, Esg1, Dnmt3L, ECAT8, Gdf3, Sox15, ECAT15-1, Fthl17, Sal14, Rex1, UTF1, Stella, Stat3, and Grb2, for example.

These gene products are disclosed in International Publication No. WO2007/069666 A1. However, gene products that can be included in the nuclear reprogramming factors described here are not limited to the gene products of genes specifically described above.

The nuclear reprogramming factors described here can include other gene products which can function as a nuclear reprogramming factor, as well as one or more factors involving differentiation, development, or proliferation, and factors having other physiological activities.

Among these genes, if one or more gene product(s) is/are already expressed in somatic cells to be reprogrammed, such gene products can be excluded from the factors to be introduced. For example, one or more gene(s) besides the already-expressed gene(s) can be introduced into somatic cells by an appropriate gene introduction method, for example, a method using a recombinant vector.

Alternatively, among these genes, if one or more gene product(s) is/are introduced into nuclei by a technique such as addition of an HIV virus-derived TAT peptide and/or nuclear localization signal to form a fusion protein or by a technique such as nuclear microinjection, or simply by addition of a small molecule capable of diffusing across the plasma membrane, the other one or more gene(s) can be introduced by an appropriate gene introduction method, for example, a method using a recombinant vector.

Fusion Products and Markers

In addition, a gene product serving as a nuclear reprogramming factor may be either a protein itself produced from the abovementioned gene, or in the form of a fusion gene product between such a protein and another protein, a peptide, or the like.

For example, a fusion protein having Green Fluorescent Protein (GFP) and a fusion gene product having a peptide such as a histidine tag may also be used. Further, use of a prepared fusion protein having a HIV virus-derived TAT peptide enables the promotion of endocytosis of a nuclear reprogramming factor through cell membrane, and also enables the induction of reprogramming by simply adding such a fusion protein into the medium while avoiding complicated manipulations such as gene introduction.

The preparation method of the aforementioned fusion gene product is well known to those skilled in the art, and therefore those skilled in the art are able to readily design and prepare an appropriate fusion gene product according to the purpose.

As described above, pluripotency may be enhanced by the addition of Tbx3.

TBX3

TBX3 is also known as T-box 3, and as UMS; XHL; TBX3-ISO; TBX3. Sequences of TBX3 include: NG_008315.1 RefSeqGene (SEQ ID NO.: 20).

T-box transcription factor TBX3 is a protein that in humans is encoded by the TBX3 gene (Li Q Y, Newbury-Ecob R A, Terrett J A, Wilson D I, Curtis A R, Yi C H, Gebuhr T, Bullen P J, Robson S C, Strachan T, Bonnet D, Lyonnet S, Young I D, Raebum J A, Buckler A J, Law D J, Brook J D (January 1997). "Holt-Oram syndrome is caused by mutations in TBX5, a member of the Brachyury (T) gene family". Nat Genet 15 (1): 21-9).

This gene is a member of a phylogenetically conserved family of genes that share a common DNA-binding domain, the T-box. T-box genes encode transcription factors involved in the regulation of developmental processes. This protein is a transcriptional repressor and is thought to play a role in the anterior/posterior axis of the tetrapod forelimb. Mutations in this gene cause ulnar-mammary syndrome, affecting limb, apocrine gland, tooth, hair, and genital development.

Alternative splicing of this gene results in three-transcript variants encoding different isoforms (as described below).

Tbx3 may be derived from the same animal species as the target animal whose somatic cells are to be reprogrammed. Tbx3 suitable for use in the methods and compositions described here includes wild type Tbx3 as well as Tbx3 in which one to several nucleotides (for example 1 to 6 nucleotides, such as 1 to 4 nucleotides, such as 1 to 3 nucleotides, for example 1 or 2 nucleotides, for example 1 nucleotide) are substituted, inserted, and/or deleted, and which are capable of exerting equivalent functions to those of the wild type Tbx3 in vivo.

For example, the Tbx3 which may be used includes Tbx3 in which one to several nucleotides are substituted, inserted, and/or deleted, and which increase the efficiency of iPS cell production. The Tbx3 described here also includes Tbx3 in which one to several nucleotides are substituted, inserted, and/or deleted, and which improve the efficiency of nuclear reprogramming.

Examples of the Tbx3 which may be used in the methods described here can include, but are not limited to, Tbx3 isoforms such as those set out in detail below.

TBX3 Isoform 1

This variant of Tbx3 (1) is a transcript variant and encodes the shorter isoform (1) of this protein. The mRNA sequence has GenBank Accession Number NM_005996.3 (SEQ ID NO. 1) T-box 3 protein isoform 1. The protein sequence has GenBank Accession Number NP_005987.3 (SEQ ID NO. 2)T-box 3 protein isoform 1.

The source sequence(s) include AF140240(SEQ ID NO. 21), AK054604 (SEQ ID NO. 22) and BC025258(SEQ ID NO. 23). A consensus CDS has the accession number CCDS9175.1(SEQ ID NO. 24). The UniProtKB/Swiss-Prot accession number is O15119. Related Ensembl sequences have accession numbers ENSP00000257567, ENST00000349155.

```
MSLSMRDPVIPGTSMAYHPFLPHRAPDFAMSAVLGHQPPFFPALTLPPNGAAALSLPGAL

AKPIMDQLVGAAETGIPFSSLGPQAHLRPLKTMEPEEEVEDDPKVHLEAKELWDQFHKRG

TEMVITKSGRRMFPPFKVRCSGLDKKAKYILLMDIIAADDCRYKFHNSRWMVAGKADPEM

PKRMYIHPDSPATGEQWMSKVVTFHKLKLTNNISDKHGFTILNSMHKYQPRFHIVRANDI

LKLPYSTFRTYLFPETEFIAVTAYQNDKITQLKIDNNPFAKGFRDTGNGRREKRKQLTLQ

SMRVFDERHKKENGTSDESSSEQAAFNCFAQASSPAASTVGTSNLKDLCPSEGESDAEAE

SKEEHGPEACDAAKISTTTSEEPCRDKGSPAVKAHLFAAERPRDSGRLDKASPDSRHSPA

TISSSTRGLGAEERRSPVREGTAPAKVEEARALPGKEAFAPLTVQTDAAAAHLAQGPLPG

LGFAPGLAGQQFFNGHPLFLHPSQFAMGGAFSSMAAAGMGPLLATVSGASTGVSGLDSTA

MASAAAAQGLSGASAATLPFHLQQHVLASQGLAMSPFGSLFPYPYTYMAAAAAASSAAAS

SSVHRHPFLNLNTMRPRLRYSPYSIPVPVPDGSSLLTTALPSMAAAAGPLDGKVAALAAS

PASVAVDSGSELNSRSSTLSSSSMSLSPKLCAEKEAATSELQSIQRLVSGLEAKPDRSRS

ASP (SEQ ID NO.:2)
```

(SEQ ID NO.: 2)

TBX3 Isoform 2

This variant of Tbx3 (2) contains an alternate in-frame exon compared to variant 1. The resulting isoform (2) has the same N- and C-termini and is longer compared to isoform 1.

The mRNA sequence has GenBank Accession Number NM_016569.3 (SEQ ID NO. 3) T-box 3 protein isoform 2. The protein sequence has GenBank Accession Number NP_057653.3 (SEQ ID NO. 4) T-box 3 protein isoform 2. The source sequence(s) include AF140240, (SEQ ID NO. 21), AK054604 (SEQ ID NO. 22) and BC025258(SEQ ID NO. 23). A consensus CDS has the accession number CCDS9176.1(SEQ ID NO. 25). The UniProtKB/Swiss-Prot accession number is O15119. Related Ensembl sequences have accession numbers ENSP00000257566, ENST00000257566.

```
MSLSMRDPVIPGTSMAYHPFLPHRAPDFAMSAVLGHQPPFFPALTLPPNGAAALSLPGAL
AKPIMDQLVGAAETGIPFSSLGPQAHLRPLKTMEPEEEVEDDPKVHLEAKELWDQFHKRG
TEMVITKSGRRMFPPFKVRCSGLDKKAKYILLMDIIAADDCRYKFHNSRWMVAGKADPEM
PKRMYIHPDSPATGEQWMSKVVTFHKLKLTNNISDKHGFTLAFPSDHATWQGNYSFGTQT
ILNSMHKYQPRFHIVRANDILKLPYSTFRTYLFPETEFIAVTAYQNDKITQLKIDNNPFA
KGFRDTGNGRREKRKQLTLQSMRVFDERHKKENGTSDESSSEQAAFNCFAQASSPAASTV
GTSNLKDLCPSEGESDAEAESKEEHGPEACDAAKISTTTSEEPCRDKGSPAVKAHLFAAE
RPRDSGRLDKASPDSRHSPATISSSTRGLGAEERRSPVREGTAPAKVEEARALPGKEAFA
PLTVQTDAAAAHLAQGPLPGLGFAPGLAGQQFFNGHPLFLHPSQFAMGGAFSSMAAAGMG
PLLATVSGASTGVSGLDSTAMASAAAAQGLSGASAATLPFHLQQHVLASQGLAMSPFGSL
FPYPYTYMAAAAAASSAAASSSVHRHPFLNLNTMRPRLRYSPYSIPVPVPDGSSLLTTAL
PSMAAAAGPLDGKVAALAASPASVAVDSGSELNSRSSTLSSSSMSLSPKLCAEKEAATSE
LQSIQRLVSGLEAKPDRSRSASP (SEQ ID NO.: 4)
```

Tbx3 Isoform 3

```
MSLSMRDPVIPGTSMAYHPFLPHRAPDFAMSAVLGHQPPFFPALTLPPNGAAALSLPGAL
AKPIMDQLVGAAETGIPFSSLGPQAHLRPLKTMEPEEEVEDDPKVHLEAKELWDQFHKRG
TEMVITKSGRRMFPPFKVRCSGLDKKAKYILLMDIIAADDCRYKFHNSRWMVAGKADPEM
PKRMYIHPDSPATGEQWMSKVVTFHKLKLTNNISDKHGFTLAFPSDHATWQGNYSFGTQT
ILNSMHKYQPRFHIVRANDILKLPYSTFRTYLFPETEFIAVTAYQNDKITQLKIDNNPFA
KGFRDTGNGRREKRKQLTLQSMRVFDERHKKENGTSDESSSEQAAFNCFAQASSPAASTV
GTSNLKDLCPSEGESDAEAESKEEHGPEACDAAKISTTTSEEPCRDKGSPAVKAHLFAAE
RPRDSGRLDKASPDSRHSPATISSSTRGLGAEERRSPVREGTAPAKVEEARALPGKEAFA
PLTVQTDAASAAASSSVHRHPFLNLNTMRPRLRYSPYSIPVPVPDGSSLLTTALAASPAS
VAVDSGSELNSRSSTLSSSSMSLSPKLCAEKEAATSELQSIQRLVSGLEAKPDRSRSASP
(SEQ ID NO.: 5)
```

TBOX

TBOX refers to the T-box DNA binding domain of the T-box family of transcriptional regulators. The T-box family is an ancient group that appears to play a critical role in development in all animal species. These genes were uncovered on the basis of similarity to the DNA binding domain of murine Brachyury (T) gene product, the defining feature of the family.

Common features shared by T-box family members are DNA-binding and transcriptional regulatory activity, a role in development and conserved expression patterns, most of the known genes in all species being expressed in mesoderm or mesoderm precursors.

Tbx3 Polypeptides

The methods and compositions described here make use of Tbx3 polypeptides, which are described in detail below.

Tbx3 is also known as T-box 3, and as UMS; XHL; Tbx3-ISO; Tbx3.

As used here, the term "Tbx3 polypeptide" is intended to refer to a sequence having GenBank Accession Number NP_005987.3 (SEQ ID NO. 2) T-box 3 protein isoform 1 or NP_057653.3 (SEQ ID NO. 4) T-box 3 protein isoform 2.

A "Tbx3 polypeptide" may comprise or consist of a human Tbx3 polypeptide.

Homologues variants and derivatives thereof of any, some or all of these polypeptides are also included.

A "polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids.

"Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-inking, cyclization, disulfide bond formation, demethylation, formation of covalent cross-inks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, *Proteins—Structure and Molecular Properties,* 2nd Ed., T. E. Creighton, W.H. Freeman and Company, New York, 1993 and Wold, F., *Post-translational Protein Modifications: Perspectives and Prospects*, pgs. 1-12 in *Posttranslational Covalent Modification of Proteins*, B. C. Johnson, Ed., Academic Press, New York, 1983; Seifter et al., "Analysis for protein modifications and nonprotein cofactors", *Meth Enzymol* (1990) 182:626-646 and Rattan et al., "Protein Synthesis: Posttranslational Modifications and Aging", *Ann NY Acad Sci* (1992) 663:48-62.

The term "polypeptide" includes the various synthetic peptide variations known in the art, such as a retroinverso 13 peptides. The peptide may be an antigenic determinant and/or a T-cell epitope. The peptide may be immunogenic in vivo. The peptide may be capable of inducing neutralising antibodies in vivo.

As applied to Tbx3, the resultant amino acid sequence may have one or more activities, such as biological activities in common with a Tbx3 polypeptide, for example a human Tbx3 polypeptide. For example, a Tbx3 homologue may have the ability to enhance pluripotency in a cell that has been exposed to Tbx3 compared to a cell that has not. In particular, the term "homologue" covers identity with respect to structure and/or function providing the resultant amino acid sequence has Tbx3 activity. With respect to sequence identity (i.e. similarity), there may be at least 70%, such as at least 75%, such as at least 85%, such as at least 90% sequence identity. There may be at least 95%, such as at least 98%, sequence identity. These terms also encompass polypeptides derived from amino acids which are allelic variations of the Tbx3 nucleic acid sequence.

Where reference is made to the "activity" or "biological activity" of a polypeptide such as Tbx3, these terms are intended to refer to the metabolic or physiological function of Tbx3, including similar activities or improved activities or these activities with decreased undesirable side effects. Also included are antigenic and immunogenic activities of Tbx3. Examples of such activities, and methods of assaying and quantifying these activities, are known in the art, and are described in detail elsewhere in this document.

Other Tbx3 Polypeptides

Tbx3 variants, homologues, derivatives and fragments are also of use in the methods and compositions described here.

The terms "variant", "homologue", "derivative" or "fragment" in relation to Tbx3 include any substitution of, variation of, modification of, replacement of, deletion of or addition of one (or more) amino acid from or to a sequence. Unless the context admits otherwise, references to "Tbx3" includes references to such variants, homologues, derivatives and fragments of Tbx3.

As used herein a "deletion" is defined as a change in either nucleotide or amino acid sequence in which one or more nucleotides or amino acid residues, respectively, are absent. As used herein an "insertion" or "addition" is that change in a nucleotide or amino acid sequence which has resulted in the addition of one or more nucleotides or amino acid residues, respectively, as compared to the naturally occurring substance. As used herein "substitution" results from the replacement of one or more nucleotides or amino acids by different nucleotides or amino acids; respectively.

Tbx3 polypeptides as described here may also have deletions, insertions or substitutions of amino acid residues which produce a silent change and result in a functionally equivalent amino acid sequence. Deliberate amino kid substitutions may be made on the basis of similarity in polarity, charge, solubility, hydrophobicity, hydrophilicity, and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the table below. Amino acids in the same block in the second column and in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Tbx3 polypeptides may further comprise heterologous amino acid sequences, typically at the N-terminus or C-terminus, such as the N-terminus. Heterologous sequences may include sequences that affect intra or extracellular protein targeting (such as leader sequences). Heterologous sequences may also include sequences that increase the immunogenicity of the Tbx3 polypeptide and/or which facilitate identification, extraction and/or purification of the polypeptides. Another heterologous sequence that may be used is a polyamino acid sequence such as polyhistidine which may be N-terminal. A polyhistidine sequence of at least 10 amino acids, such as at least 17 amino acids but fewer than 50 amino acids may be employed.

The Tbx3 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Tbx3 polypeptides as described here are advantageously made by recombinant means, using known techniques. However they may also be made by synthetic means using techniques well known to skilled persons such as solid phase synthesis. Such polypeptides may also be produced as fusion proteins, for example to aid in extraction and purification. Examples of fusion protein partners include glutathione-S-transferase (GST), 6xHis, GAL4 (DNA binding and/or transcriptional activation domains) and β-galactosidase. It may also be convenient to include a proteolytic cleavage site between the fusion protein partner and the protein sequence of interest to allow removal of fusion protein sequences, such as a thrombin cleavage site. The fusion protein may be one which does not hinder the function of the protein of interest sequence.

The Tbx3 polypeptides may be in a substantially isolated form. This term is intended to refer to alteration by the hand of man from the natural state. If an "isolated" composition, or substance occurs in nature, it has been changed or removed from its original environment, or both. For example, a polynucleotide, nucleic acid or a polypeptide naturally present in a living animal is not "isolated," but the same polynucleotide, nucleic acid or polypeptide separated from the coexisting materials of its natural state is "isolated", as the term is employed herein.

It will however be understood that the Tbx3 protein may be mixed with carriers or diluents which will not interfere with the intended purpose of the protein and still be regarded as substantially isolated. A Tbx3 polypeptide may also be in a substantially purified form, in which case it will generally comprise the protein in a preparation in which more than 90%, for example, 95%, 98% or 99% of the protein in the preparation is a Tbx3 polypeptide.

By aligning Tbx3 sequences from different species, it is possible to determine which regions of the amino acid sequence are conserved between different species ("homologous regions"), and which regions vary between the different species ("heterologous regions").

The Tbx3 polypeptides may therefore comprise a sequence which corresponds to at least part of a homologous region. A homologous region shows a high degree of homology between at least two species. For example, the homologous region may show at least 70%, at least 80%, at least 90% or at least 95% identity at the amino acid level using the tests described above. Peptides which comprise a sequence which corresponds to a homologous region may be used in therapeutic strategies as explained in further detail below. Alternatively, the Tbx3 peptide may comprise a sequence which corresponds to at least part of a heterologous region. A heterologous region shows a low degree of homology between at least two species.

Tbx3 Homologues

The Tbx3 polypeptides disclosed for use include homologous sequences obtained from any source, for example related viral/bacterial proteins, cellular homologues and synthetic peptides, as well as variants or derivatives thereof. Thus polypeptides also include those encoding homologues of Tbx3 from other species including animals such as mammals (e.g. mice, rats or rabbits), especially primates, more especially humans. More specifically, homologues include human homologues.

In the context of this document, a homologous sequence is taken to include an amino acid sequence which is at least 15, 20, 25, 30, 40, 50, 60, 70, 80 or 90% identical, such as at least 95 or 98% identical at the amino acid level, for example over at least 50, 100, 150, 200, 250, 300, 350, 400, 450, 500, 550, 600, 650, 700 or more amino acids with the sequence of a relevant Tbx3 sequence.

In particular, homology should typically be considered with respect to those regions of the sequence known to be essential for protein function rather than non-essential neighbouring sequences. This is especially important when considering homologous sequences from distantly related organisms. Example include residue numbers 107-220 for DNA binding comprising the T-box; first part, residue numbers 241-305 for DNA binding comprising the T-box; second part and residue numbers 544-695 for transcription repression.

Although homology can also be considered in terms of similarity (i.e. amino acid residues having similar chemical properties/functions), in the context of the present document homology may be expressed in terms of sequence identity.

Homology comparisons can be conducted by eye, or more usually, with the aid of readily available sequence comparison programs. These publicly and commercially available computer programs can calculate % identity between two or more sequences.

% identity may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local identity or similarity.

However, these more complex methods assign "gap penalties" to each gap that occurs in the alignment so that, for the same number of identical amino acids, a sequence alignment with as few gaps as possible reflecting higher relatedness between the two compared sequences will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, the default values may be used when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Altschul et al., 1990, J. Mol. Biol., 403.410) and the GENEWORKS suite of comparison tools. Both BLAST and FASTA are available for offline and online searching (see Ausubel et al., 1999 ibid, pages 7-58 to 7-60). The GCG Bestfit program may be used.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). The public default values for the GCG package may be used, or in the case of other software, the default matrix, such as BLOSUM62.

Once the software has produced an optimal alignment, it is possible to calculate % homology, such as % sequence identity. The software typically does this as part of the sequence comparison and generates a numerical result.

The terms "variant" or "derivative" in relation to amino acid sequences includes any substitution of, variation of, modification of, replacement of, deletion of or addition of one (or more) amino acids from or to the sequence providing the resultant amino acid sequence retains substantially the same activity as the unmodified sequence, such as having at least the same activity as the Tbx3 polypeptides.

Polypeptides having the Tbx3 amino acid sequence disclosed here, or fragments or homologues thereof may be modified for use in the methods and compositions described here. Typically, modifications are made that maintain the biological activity of the sequence. Amino acid substitutions may be made, for example from 1, 2 or 3 to 10, 20 or 30 substitutions provided that the modified sequence retains the biological activity of the unmodified sequence. Alternatively, modifications may be made to deliberately inactivate one or more functional domains: of the polypeptides described here. Amino acid substitutions may include the use of non-naturally occurring analogues, for example to increase blood plasma half-life of a therapeutically administered polypeptide.

Tbx3 Fragments

Polypeptides for use in the methods and compositions described here also include fragments of the full length sequence of any of the Tbx3 polypeptides identified above. Fragments may comprise at least one epitope. Methods of identifying epitopes are well known in the art. Fragments will typically comprise at least 6 amino acids, such as at least 10, 20, 30, 50 or 100 amino acids.

Included are fragments comprising or consisting of, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 200, 250, 300, 350, 400, 450, 500, 550, 600, 650, 700 or more residues from a relevant Tbx3 amino acid sequence.

We further describe peptides comprising a portion of a Tbx3 polypeptide as described here. Thus, fragments of Tbx3 and its homologues, variants or derivatives are included. The peptides may be between 2 and 200 amino acids, such as between 4 and 40 amino acids in length. The peptide may be derived from a Tbx3 polypeptide as disclosed here, for example by digestion with a suitable enzyme, such as trypsin. Alternatively the peptide, fragment, etc may be made by recombinant means, or synthesised synthetically.

Such Tbx3 fragments may be used to generate probes to preferentially detect Tbx3 expression, for example, through antibodies generated against such fragments. These antibodies would be expected to bind specifically to Tbx3, and are useful in the methods of diagnosis and treatment disclosed here.

Tbx3 and its fragments, homologues, variants and derivatives, may be made by recombinant means. However they may also be made by synthetic means using techniques well known to skilled persons such as solid phase synthesis. The proteins may also be produced as fusion proteins, for example to aid in extraction and purification. Examples of fusion protein partners include glutathione-S-transferase (GST), 6xHis, GAL4 (DNA binding and/or transcriptional activation domains) and β-galactosidase. It may also be convenient to include a proteolytic cleavage site between the fusion protein partner and the protein sequence of interest to allow removal of fusion protein sequences. The fusion protein may be one which will not hinder the function of the protein of interest sequence. Proteins may also be obtained by purification of cell extracts from animal cells.

The Tbx3 polypeptides, variants, homologues, fragments and derivatives disclosed here may be in a substantially isolated form. It will be understood that such polypeptides may be mixed with carriers or diluents which will not interfere with the intended purpose of the protein and still be regarded as substantially isolated. A Tbx3 variant, homologue, fragment or derivative may also be in a substantially purified form, in which case generally comprise the protein in a preparation in which more than 90%, e.g. 95%, 98% or 99% of the protein in the preparation is a protein.

The Tbx3 polypeptides, variants, homologues, fragments and derivatives disclosed here may be labelled with a revealing label. The revealing label may be any suitable label which allows the polypeptide, etc to be detected. Suitable labels include radioisotopes, e.g. 125/, enzymes, antibodies, polynucleotides and linkers such as biotin. Labelled polypeptides may be used in diagnostic procedures such as immunoassays to determine the amount of a polypeptide in a sample. Polypeptides or labelled polypeptides may also be used in serological or cell-mediated immune assays for the detection of immune reactivity to said polypeptides in animals and humans using standard protocols.

A Tbx3 polypeptides, variants, homologues, fragments and derivatives disclosed here, optionally labelled, may also be fixed to a solid phase, for example the surface of an immunoassay well or dipstick. Such labelled and/or immobilised polypeptides may be packaged into kits in a suitable container along with suitable reagents, controls, instructions and the like. Such polypeptides and kits may be used in methods of detection of antibodies to the polypeptides or their allelic or species variants by immunoassay.

Immunoassay methods are well known in the art and will generally comprise: (a) providing a polypeptide comprising an epitope bindable by an antibody against said protein; (b)

incubating a biological sample with said polypeptide under conditions which allow for the formation of an antibody-antigen complex; and (c) determining whether antibody-antigen complex comprising said polypeptide is formed.

The Tbx3 polypeptides, variants, homologues, fragments and derivatives disclosed here may be used in in vitro or in vivo cell culture systems to study the role of their corresponding genes and homologues thereof in cell function, including their function in disease. For example, truncated or modified polypeptides may be introduced into a cell to disrupt the normal functions which occur in the cell. The polypeptides may be introduced into the cell by in situ expression of the polypeptide from a recombinant expression vector (see below). The expression vector optionally carries an inducible promoter to control the expression of the polypeptide.

The use of appropriate host cells, such as insect cells or mammalian cells, is expected to provide for such post-translational modifications (e.g. myristolation, glycosylation, truncation, lapidation and tyrosine, serine or threonine phosphorylation) as may be needed to confer optimal biological activity on recombinant expression products. Such cell culture systems in which the Tbx3 polypeptides, variants, homologues, fragments and derivatives disclosed here are expressed may be used in assay systems to identify candidate substances which interfere with or enhance the functions of the polypeptides in the cell.

Tbx3 Nucleic Acids

The methods and compositions described here may employ, as a means for detecting expression levels of Tbx3, Tbx3 polynucleotides, Tbx3 nucleotides and Tbx3 nucleic acids, as well as variants, homologues, derivatives and fragments of any of these. In addition, we disclose particular Tbx3 fragments useful for the methods of diagnosis described here. The Tbx3 nucleic acids may also be used for the methods of treatment or prophylaxis described.

The terms "Tbx3 polynucleotide", "Tbx3 nucleotide" and "Tbx3 nucleic acid" may be used interchangeably, and should be understood to specifically include both cDNA and genomic Tbx3 sequences. These terms are also intended to include a nucleic acid sequence capable of encoding a Tbx3 polypeptide and/or a fragment, derivative, homologue or variant of this.

Where reference is made to a Tbx3 nucleic acid, this should be taken as a reference to any member of the Tbx3 family of nucleic acids. Of particular interest are Tbx3 nucleic acids selected from the group consisting of: GenBank Accession Number NM_005996.3 (SEQ ID NO. 1) T-box 3 protein isoform 1 and GenBank Accession Number NM_016569.3 (SEQ ID NO. 3) T-box 3 protein isoform 2.

Also included are any one or more of the nucleic acid sequences set out as "Other Tbx3 nucleic acid sequences" below.

For example, the Tbx3 nucleic acid may comprise a human Tbx3 sequence having GenBank Accession Number NM_005996.3 (SEQ ID NO. 1) T-box 3 protein isoform 1 or GenBank Accession Number NM_016569.3 (SEQ ID NO. 3) T-box 3 protein isoform 2.

Tbx3 nucleic acids may be used for a variety of means, for example, for enhancing or inducing pluripotency in cells such as somatic cells, stem cells and induced pluripotent stem cells. Tbx3 nucleic acids may also be used for the expression or production of Tbx3 polypeptides.

"Polynucleotide" generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

It will be understood by the skilled person that numerous nucleotide sequences can encode the same polypeptide as a result of the degeneracy of the genetic code.

As used herein, the term "nucleotide sequence" refers to nucleotide sequences, oligonucleotide sequences, polynucleotide sequences and variants, homologues, fragments and derivatives thereof (such as portions thereof). The nucleotide sequence may be DNA or RNA of genomic or synthetic or recombinant origin which may be double-stranded or single-stranded whether representing the sense or antisense strand or combinations thereof. The term nucleotide sequence may be prepared by use of recombinant DNA techniques (for example, recombinant DNA).

The term "nucleotide sequence" may means DNA.

Other Nucleic Acids

We also provide nucleic acids which are fragments, homologues; variants or derivatives of Tbx3 nucleic acids. The terms "variant", "homologue", "derivative" or "fragment" in relation to Tbx3 nucleic acid include any substitution of, variation of, modification of, replacement of, deletion of or addition of one (or more) nucleic acids from or to the sequence of a Tbx3 nucleotide sequence. Unless the context admits otherwise, references to "Tbx3" and "Tbx3" include references to such variants, homologues, derivatives and fragments of Tbx3.

The resultant nucleotide sequence may encode a polypeptide having any one or more Tbx3 activity. The term "homologue" may be intended to cover identity with respect to structure and/or function such that the resultant nucleotide sequence encodes a polypeptide which has Tbx3 activity. For example, a homologue etc of Tbx3 may have be capable of inducing or enhancing pluripotency in a cell such as a stem cell, somatic cell or induced pluripotent stem cell, when exposed to such a cell, compared to a cell which has not been so exposed.

With respect to sequence identity (i.e. similarity), there may be at least 70%, at least 75%, at least 85% or at least 90% sequence identity. There may be at least 95%, such as at least 98%, sequence identity to a relevant sequence (e.g., a Tbx3 sequence having GenBank Accession Number NM_005996.3 (SEQ ID NO. 1) T-box 3 protein isoform 1 or GenBank Accession Number NM_016569.3 (SEQ ID NO. 3) T-box 3 protein isoform 2). These terms also encompass allelic variations of the sequences.

Variants, Derivatives and Homologues

Tbx3 nucleic acid variants, fragments, derivatives and homologues may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of this document, it is to be understood that the polynucleotides may be modified by any method available in the art. Such modifications may be carried-out in order to enhance the in vivo activity or life span of polynucleotides of interest.

Where the polynucleotide is double-stranded, both strands of the duplex, either individually or in combination, are encompassed by the methods and compositions described here. Where the polynucleotide is single-stranded, it is to be understood that the complementary sequence of that polynucleotide is also included.

The terms "variant", "homologue" or "derivative" in relation to a nucleotide sequence include any substitution of, variation of, modification of, replacement of, deletion of or addition of one (or more) nucleic acid from or to the sequence. Said variant, homologues or derivatives may code for a polypeptide having biological activity. Such fragments, homologues, variants and derivatives of Tbx3 may comprise modulated activity, as set out above.

As indicated above, with respect to sequence identity, a "homologue" may have at least 5% identity, at least 10% identity, at least 15% identity, at least 20% identity, at least 25% identity, at least 30% identity, at least 35% identity, at least 40% identity, at least 45% identity, at least 50% identity, at least 55% identity, at least 60% identity, at least 65% identity, at least 70% identity, at least 75% identity, at least 80% identity, at least 85% identity, at least 90% identity, or at least 95% identity to the relevant sequence (e.g., a Tbx3 sequence having GenBank Accession Number NM_005996.3 (SEQ ID NO. 1) T-box 3 protein isoform 1 or GenBank Accession Number NM_016569.3 (SEQ ID NO. 3) T-box 3 protein isoform 2).

There may be at least 95% identity, at least 96% identity, at least 97% identity, at least 98% identity or at least 99% identity. Nucleotide identity-comparisons may be conducted as described above. A sequence comparison program which may be used is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

Hybridisation

We further describe nucleotide sequences that are capable of hybridising selectively to any of the sequences presented herein, or any variant, fragment or derivative thereof, or to the complement of any of the above. Nucleotide sequences may be at least 15 nucleotides in length, such as at least 20, 30, 40 or 50 nucleotides in length.

The term "hybridization" as used herein shall include "the process by which a strand of nucleic acid joins with a complementary strand through base pairing" as well as the process of amplification as carried out in polymerase chain reaction technologies.

Polynucleotides capable of selectively hybridising to the nucleotide sequences presented herein, or to their complement, may be at least 40% homologous, at least 45% homologous, at least 50% homologous, at least 55% homologous, at least 60% homologous, at least 65% homologous, at least 70% homologous, at least 75% homologous, at least 80% homologous, at least 85% homologous, at least 90% homologous, or at least 95% homologous to the corresponding nucleotide sequences presented herein (e.g., a Tbx3 sequence having GenBank Accession Number NM_005996.3 (SEQ ID NO. 1) T-box 3 protein isoform 1 or GenBank Accession Number NM_016569.3 (SEQ ID NO. 3) T-box 3 protein isoform 2.). Such polynucleotides may be generally at least 70%, at least 80 or 90% or at least 95% or 98% homologous to the corresponding nucleotide sequences over a region of at least 20, such as at least 25 or 30, for instance at least 40, 60 or 100 or more contiguous nucleotides.

The term "selectively hybridizable" means that the polynucleotide used as a probe is used under conditions where a target polynucleotide is found to hybridize to the probe at a level significantly above background. The background hybridization may occur because of other polynucleotides present, for example, in the cDNA or genomic DNA library being screening. In this event, background implies a level of signal generated by interaction between the probe and a non-specific DNA member of the library which is less than 10 fold, such as less than 100 fold as intense as the specific interaction observed with the target DNA. The intensity of interaction may be measured, for example, by radiolabelling the probe, e.g. with $^{32}P$ or $^{33}P$ or with non-radioactive probes (e.g., fluorescent dyes, biotin or digoxigenin).

Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

We provide nucleotide sequences that may be able to hybridise to the Tbx3 nucleic acids, fragments, variants, homologues or derivatives under stringent conditions (e.g. 65° C. and 0.1×SSC (1×SSC=0.15 M NaCl, 0.015 M $Na_3$ Citrate pH 7.0)).

Generation of Homologues, Variants and Derivatives

Polynucleotides which are not 100% identical to the relevant sequences (e.g., a Tbx3 sequence having GenBank Accession Number NM_005996.3 (SEQ ID NO. 1) T-box 3 protein isoform 1 or GenBank Accession Number NM_016569.3 (SEQ ID NO. 3) T-box 3 protein isoform 2) but which are also included, as well as homologues, variants and derivatives of Tbx3 can be obtained in a number of ways. Other variants of the sequences may be obtained for example by probing DNA libraries made from a range of individuals, for example individuals from different populations. For example, Tbx3 homologues may be identified from other individuals, or other species. Further recombinant Tbx3 nucleic acids and polypeptides may be produced by identifying corresponding positions in the homologues, and synthesising or producing the molecule as described elsewhere in this document.

In addition, other viral/bacterial, or cellular homologues of Tbx3, particularly cellular homologues found in mammalian cells (e.g. rat, mouse, bovine and primate cells), may be obtained and such homologues and fragments thereof in general will be capable of selectively hybridising to human Tbx3. Such homologues may be used to design non-human Tbx3 nucleic acids, fragments, variants and homologues. Mutagenesis may be carried out by means known in the art to produce further variety.

Sequences of Tbx3 homologues may be obtained by probing cDNA libraries made from or genomic DNA libraries from other animal species, and probing such libraries with probes comprising all or part of any of the Tbx3 nucleic acids, fragments, variants and homologues, or other fragments of Tbx3 under conditions of medium to high stringency.

Similar considerations apply to obtaining species homologues and allelic variants of the polypeptide or nucleotide sequences disclosed here.

Variants and strain/species homologues may also be obtained using degenerate PCR which will use primers designed to target sequences within the variants and homologues encoding conserved amino acid sequences within the sequences of the Tbx3 nucleic acids. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences. It will be appreciated by the skilled person that overall nucleotide homology between sequences from distantly related organisms is likely to be very low and thus in these situations degenerate PCR may be the method of choice rather than screening libraries with labelled fragments the Tbx3 sequences.

In addition, homologous sequences may be identified by searching nucleotide and/or protein databases using search algorithms such as the BLAST suite of programs.

Alternatively, such polynucleotides may be obtained by site directed mutagenesis of characterised sequences, for example, Tbx3 nucleic acids, or variants, homologues, derivatives or fragments thereof. This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

The polynucleotides described here may be used to produce a primer, e.g. a PCR primer, a primer for an alternative amplification reaction; a probe e.g. labelled with a revealing label by conventional means using radioactive or non-radioactive labels, or the polynucleotides may be cloned into vectors. Such primers, probes and other fragments will be at least 8, 9, 10, or 15, such as at least 20, for example at least 25, 30 or 40 nucleotides in length, and are also encompassed by the term “polynucleotides” as used herein.

Polynucleotides such as a DNA polynucleotides and probes may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Primers comprising fragments of Tbx3 are particularly useful in the methods of detection of Tbx3 expression, such as up-regulation of Tbx3 expression. Suitable primers for amplification of Tbx3 may be generated from any suitable stretch of Tbx3. Primers which may be used include those capable of amplifying a sequence of Tbx3 which is specific.

Although Tbx3 primers may be provided on their own, they are most usefully provided as primer pairs, comprising a forward primer and a reverse primer.

Longer polynucleotides will generally be produced using recombinant means, for example using a PCR (polymerase chain reaction) cloning techniques. This will involve making a pair of primers (e.g. of about 15 to 30 nucleotides), bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector Polynucleotides or primers may carry a revealing label. Suitable labels include radioisotopes such as $^{32}P$ or $^{35}S$, digoxigenin, fluorescent dyes, enzyme labels, or other protein labels such as biotin. Such labels may be added to polynucleotides or primers and may be detected using by techniques known per se. Polynucleotides or primers or fragments thereof labelled or unlabeled may be used by a person skilled in the art in nucleic acid-based tests for detecting or sequencing polynucleotides in the human or animal body.

Such tests for detecting generally comprise bringing a biological sample containing DNA or RNA into contact with a probe comprising a polynucleotide or primer under hybridising conditions and detecting any duplex formed between the probe and nucleic acid in the sample. Such detection may be achieved using techniques such as PCR or by immobilising the probe on a solid support, removing nucleic acid in the sample which is not hybridised to the probe, and then detecting nucleic acid which has hybridised to the probe. Alternatively, the sample nucleic acid may be immobilised on a solid support, and the amount of probe bound to such a support can be detected. Suitable assay methods of this and other formats can be found in for example WO89/03891 and WO90/13667.

Tests for sequencing nucleotides, for example, the Tbx3 nucleic acids, involve bringing a biological sample containing target DNA or RNA into contact with a probe comprising a polynucleotide or primer under hybridising conditions and determining the sequence by, for example the Sanger dideoxy chain termination method (see Sambrook et al.).

Such a method generally comprises elongating, in the presence of suitable reagents, the primer by synthesis of a strand complementary to the target DNA or RNA and selectively terminating the elongation reaction at one or more of an A, C, G or T/U residue; allowing strand elongation and termination reaction to occur; separating out according to size the elongated products to determine the sequence of the nucleotides at which selective termination has occurred. Suitable reagents include a DNA polymerase enzyme, the deoxynucleotides dATP, dCTP, dGTP and dTTP, a buffer and ATP. Dideoxynucleotides are used for selective termination.

Tbx3 Control Regions

For some purposes, it may be necessary to utilise or investigate control regions of Tbx3. Such control regions include promoters, enhancers and locus control regions. By a control region we mean a nucleic acid sequence or structure which is capable of modulating the expression of a coding sequence which is operatively linked to it.

For example, control regions are useful in generating transgenic animals expressing Tbx3. Furthermore, control regions may be used to generate expression constructs for Tbx3. This is described in further detail below.

Identification of control regions of Tbx3 is straightforward, and may be carried out in a number of ways. For example, the coding sequence of Tbx3 may be obtained from an organism, by screening a cDNA library using a human or mouse Tbx3 cDNA sequence as a probe. 5' sequences may be obtained by screening an appropriate genomic library, or by primer extension as known in the art. Database searching of genome databases may also be employed. Such 5' sequences which are particularly of interest include non-coding regions. The 5' regions may be examined by eye, or with the aid of computer programs, to identify sequence motifs which indicate the presence of promoter and/or enhancer regions.

Furthermore, sequence alignments may be conducted of Tbx3 nucleic acid sequences from two or more organisms. By aligning Tbx3 sequences from different species, it is possible to determine which regions of the amino acid sequence are conserved between different species. Such conserved regions are likely to contain control regions for the gene in question (i.e., Tbx3). The mouse and human genomic sequences as disclosed here, for example, a mouse Tbx3 genomic sequence, may be employed for this purpose. Furthermore, Tbx3 homologues from other organisms may be obtained using standard methods of screening using appropriate probes generated from the mouse and human Tbx3 sequences. The genome of the pufferfish (*Takifugu rubripes*) or zebrafish may also be screened to identify a Tbx3 homologue; thus, several zebrafish sequences of Tbx3 have been identified (noted above). Comparison of the 5' non-coding region of the Fugu or zebrafish Tbx3 gene with a mouse or human genomic Tbx3 sequence may be used to identify conserved regions containing control regions.

Deletion studies may also be conducted to identify promoter and/or enhancer regions for Tbx3.

The identity of putative control regions may be confirmed by molecular biology experiments, in which the candidate sequences are linked to a reporter gene and the expression of the reporter detected.

Exposing Cells to Tbx3

Tbx3 may be exposed to a cell in the presence of one or more nuclear reprogramming factors for enhancing pluripotency.

The production method of Tbx3 for use in the methods and compositions described here is not specifically limited, although the production can be achieved, for example, by chemical synthetic method or a method using genetic recombination technique.

When the production is carried out by a method using genetic recombination technique, Tbx3 for use in the methods and compositions described here can, for example, be produced through transcription reaction with use of a DNA template and a RNA polymerase obtained by means of gene recombination. Examples of usable RNA polymerase include a T7 RNA polymerase, a T3 RNA polymerase, and a SP6 RNA polymerase.

Alternatively, a recombinant vector capable of expressing Tbx3 can be produced by insertion of Tbx3-encoding DNA into an appropriate vector under the regulation of expression control sequences (promoter and enhancer sequences and the like). The type of vector used herein is not specifically limited, although DNA vectors may be specifically used. Examples thereof can include viral vectors and plasmid vectors. The viral vector is not specifically limited, although retroviral vectors, adenoviral vectors, adeno-associated viralvectors, and the like can be employed. In addition, as to the above plasmids, mammalian expression plasmids well known to those skilled in the art can be employed.

Methods for using a retrovirus as a vector are disclosed in WO 2007/69666 A1; Takahashi et al., Cell 126:663-676, 2006; and Takahashi et al., Cell 131:861-872, 2007, which are herein incorporated by reference in their entireties. Methods for using a lentivirus as a vector are disclosed in Yu et al.; Science 318:1917-1920, 2007, which is herein incorporated by reference in its entirety. Methods for using adenovirus as a vector are disclosed in Stadtfeld et al., Science 322:945-949, 2008, which is herein incorporated by reference in its entirety. Methods for using a plasmid as a non-viral vector are disclosed in U.S. Provisional Application No. 61/071,508; U.S. Provisional Application No. 61/136,246; U.S. Provisional Application No. 61/136,615; and Okita et al., Science 322: 949-953, 2008, which are herein incorporated by reference in their entireties. One of ordinary skill in the art could choose and use an appropriate method from among the above known methods, or from any of the other known methods or vectors available in the prior art.

Nuclear reprogramming can be performed in the presence of Tbx3 in any number of ways. The manner of providing the Tbx3 is not specifically limited, although examples thereof can include a method for directly injecting Tbx3 into nuclei of somatic cells, and a method for introducing an appropriate recombinant vector capable of expressing Tbx3 into somatic cells. However, these methods are not to be considered as limiting.

The method for introducing a recombinant vector into somatic cells is not specifically limited, and can be carried out by any method well known to those skilled in the art. Examples of the employable methods can include transient transfection, microinjection, a calcium phosphate precipitation method, liposome-mediated transfection, DEAE dextran-mediated transfection, electroporation, and methods comprising the use of a gene gun.

Induction or Enhancement of Pluripotency

Cells treated by the methods and compositions described here display induced or enhanced pluripotency. In other words, such cells obtain or retain at least one characteristic of a stem cell, such as a primate or human stem cell. Such cells may retain the characteristic after one or more passages. They may do so after a plurality of passages.

The pluripotency or stem cell characteristic may comprise a morphological characteristic, immunohistochemical characteristic, a molecular biological characteristic, etc. The characteristic may comprise a biological activity.

Stem Cell Characteristics

The cells treated by our methods, in which pluripotency is enhanced or induced, may display any of the following stem cell characteristics.

Stem cells may display increased expression of Oct4 and/or SSEA-1. Expression of any one or more of Flk-1, Tie-2 and c-kit may be decreased. Stem cells which are self-renewing may display a shortened cell cycle compared to stem cells which are not self-renewing.

Stem cells may display defined morphology. For example, in the two dimensions of a standard microscopic image, human embryonic stem cells display high nuclear/cytoplasmic ratios in the plane of the image, prominent nucleoli, and compact colony formation with poorly discernable cell junctions.

Stem cells may also be characterized by expressed cell markers as described in further detail below.

Expression of Pluripotency Markers

The biological activity that is retained may comprise expression of a pluripotency marker.

Stage-specific embryonic antigens (SSEA) are characteristic of certain embryonic cell types. Antibodies for SSEA markers are available from the Developmental Studies Hybridoma Bank (Bethesda Md.). Other useful markers are detectable using antibodies designated Tra-1-60 and Tra-1-81 (Andrews et al., Cell Linesfrom Human Gem Cell Tumors, in E. J. Robertson, 1987, supra). Human embryonic stem cells are typically SSEA-1 negative and SSEA-4 positive. hEG cells are typically SSEA-1 positive. Differentiation of pPS cells in vitro results in the loss of SSEA-4, Tra-1-60, and Tra-1-81 expression and increased expression of SSEA-1. pPS cells can also be characterized by the presence of alkaline phosphatase activity, which can be detected by fixing the cells with 4% paraformaldehyde, and then developing with Vector Red as a substrate, as described by the manufacturer (Vector Laboratories, Burlingame Calif.).

Embryonic stem cells are also typically telomerase positive and OCT-4 positive. Telomerase activity can be determined using TRAP activity assay (Kim et al., Science 266:2011, 1997), using a commercially available kit (TRAPeze® XK Telomerase Detection Kit, Cat. s7707; Intergen Co., Purchase N.Y.; or TeloTAGGG™ Telomerase PCR ELISA plus, Cat. 2,013,89; Roche Diagnostics, Indianapolis). hTERT expression can also be evaluated at the mRNA level by RT-PCR. The LightCycler TeloTAGGG™ hTERT quantification kit (Cat. 3,012,344; Roche Diagnostics) is available commercially for research purposes.

Any one or more of these pluripotency markers, including FOXD3, PODXL, alkaline phosphatase, OCT-4, SSEA-4 and TRA-1-60, etc, may be retained by the cells produced by the methods and compositions described here.

Detection of markers may be achieved through any means known in the art, for example immunologically. Histochemical staining, flow cytometry (FACs), Western Blot, enzyme-linked immunoassay (ELISA), etc may be used.

Flow immunocytochemistry may be used to detect cell-surface markers immunohistochemistry (for example, of fixed cells or tissue sections) may be used for intracellular or cell-surface markers. Western blot analysis may be conducted on cellular extracts. Enzyme-linked immunoassay may be used for cellular extracts or products secreted into the medium.

For this purpose, antibodies to the pluripotency markers as available from commercial sources may be used.

Antibodies for the identification of stem cell markers including the Stage-Specific Embryonic Antigens 1 and 4 (SSEA-1 and SSEA-4) and Tumor Rejection Antigen 1-60 and 1-81 (TRA-1-60, TRA-1-81) may be obtained commercially, for example from Chemicon International, Inc (Temecula, Calif., USA). The immunological detection of these antigens using monoclonal antibodies has been widely used to characterize pluripotent stem cells (Shamblott M. J. et. al. (1998) PNAS 95: 13726-13731; Schuldiner M. et. al. (2000). PNAS 97: 11307-11312; Thomson J. A. et. al. (1998). Science 282: 1145-1147; Reubinoff B. E. et. al. (2000). Nature Biotechnology 18: 399-404; Henderson J. K. et. al. (2002). Stem Cells 20: 329-337; Pera M. et. al. (2000). J. Cell Science 113: 5-10.).

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. Sequence data for the particular markers listed in this disclosure can be obtained from public databases such as GenBank (URL www.ncbi.nlm.nih.gov:80/entrez). See U.S. Pat. No. 5,843,780 for further details.

Substantially all of the cells treated by the methods and compositions described here, or a substantial portion of them, may express the marker(s). For example, the percentage of cells that express the marker or markers may be 50% or more, 60% or more, 70% or more, 80% or more, 90% or more, 93% or more, 95% or more, 97% or more, 97% or more, 99% or more, or substantially 100%.

Cell Viability

The biological activity may comprise cell viability after treatment by the methods and compositions described here, or after propagation following treatment. Cell viability may be assayed in various ways, for example by Trypan Blue exclusion.

A protocol for vital staining follows. Place a suitable volume of a cell suspension (20-200 μL) in appropriate tube add an equal volume of 0.4% Trypan blue and gently mix, let stand for 5 minutes at room temperature. Place 10 μl of stained cells in a hemocytometer and count the number of viable (unstained) and dead (stained) cells. Calculate the average number of unstained cells in each quadrant, and multiply by $2\times10^4$ to find cells/ml. The percentage of viable cells is the number of viable cells divided by the number of dead and viable cells.

The viability of cells may be 50% or more, 60% or more, 70% or more, 80% or more, 90% or more, 93% or more, 95% or more, 97% or more, 97% or more, 99% or more, or substantially 100%.

Karyotype

The cells treated by the methods and compositions described here, in which pluripotency is enhanced or induced, may retain a normal karyotype during or after propagation. A "normal" karyotype is a karyotype that is identical, similar or substantially similar to a karyotype of a parent stem cell from which the propagule is derived, or one which varies from it but not in any substantial manner. For example, there should not be any gross anomalies such as translocations, loss of chromosomes, deletions, etc.

Karyotype may be assessed by a number of methods, for example visually under optical microscopy. Karyotypes may be prepared and analyzed as described in McWhir et al. (2006), Hewitt et al. (2007), and Gallimore and Richardson (1973). Cells may also be karyotyped using a standard G-banding technique (available at many clinical diagnostics labs that provides routine karyotyping services, such as the Cytogenetics Lab at Oakland Calif.) and compared to published stem cell karyotypes.

All or a substantial portion of cells treated by the methods and compositions described here may retain a normal karyotype. This proportion may be 50% or more, 60% or more, 70% or more, 80% or more, 90% or more, 93% or more, 95% or more, 97% or more, 97% or more, 99% or more, or substantially 100%.

Pluripotency

The cells treated by our methods may retain the capacity to differentiate into all three cellular lineages, i.e., endoderm, ectoderm and mesoderm. Methods of induction of stem cells to differentiate each of these lineages are known in the art and may be used to assay the capability of the cells to differentiate. All or a substantial portion of the treated cells may retain this ability. This may be 50% or more, 60% or more, 70% or more, 80% or more, 90% or more, 93% or more, 95% or more, 97% or more, 97% or more, 99% or more, or substantially 100% of the treated cells.

Assay for Nuclear Reprogramming by TBX3

The difference in the nuclear reprogramming efficiency with and without Tbx3 can be understood by, for example, the following manner.

Transgenic mice may be generated by insertion of sequences encoding Enhanced Green Fluorescent Protein (EGFP) and an antibiotic (such as neomycin or puromycin) resistance gene downstream of a gene promoter region, the expression of which is specific to ES cells (such as Nanog). Three genes, for example, Oct3/4, Sox2, and Klf4, and various Tbx3 are then introduced into embryonic fibroblasts derived from these transgenic mice to induce nuclear reprogramming, followed by confirmation of the production efficiency of induced pluripotent stem cells.

The production efficiency can be determined, for example, by counting the number of colonies. More specifically, the number of colonies can be compared by the following manner: drug selection is started from the 21st day after introduction of the above genes and Tbx3; and the number of total colonies and the number of Nanog GFP positive colonies (GFP, the expression of which is induced by the Nanog gene promoter region, is observable under fluorescent microscopy) are counted on the 28th day.

It should be understood, however, that: the confirmation of the nuclear reprogramming efficiency is not limited to the above method; appropriate modification and alteration can be made in the above method; and any appropriate method can be employed by those skilled in the art.

Co-Culture and Feeders

Our methods may comprise culturing stem cells in the presence or absence of co-culture. The term "co-culture" refers to a mixture of two or more different kinds of cells that are grown together, for example, stromal feeder cells. The two or more different kinds of cells may be grown on the same surfaces, such as particles or cell container surfaces, or on different surfaces. The different kinds of cells may be grown on different particles or container surfaces.

Feeder cells, as the term is used in this document, may mean cells which are used for or required for cultivation of cells of a different type. In the context of stem cell culture, feeder cells have the function of securing the survival, proliferation, and maintenance of ES-cell pluripotency. ES-cell pluripotency may be achieved by directly co-cultivating the feeder cells. Alternatively, or in addition, the feeder cells may be cultured in a medium to condition it. The conditioned medium may be used to culture the stem cells.

The inner surface of the container such as a culture dish may be coated with a feeder layer of mouse embryonic skin cells that have been treated so they will not divide. The feeder cells release nutrients into the culture medium which are required for ES cell growth. The stem cells may be grown in such coated containers.

The feeder cells may themselves be grown on particles. They may be seeded on particles in a similar way as described for stem cells. The stem cells to be propagated may be grown together with or separate from such feeder particles. The stem cells may therefore be grown on a layer on such feeder cell coated particles. On the other hand, the stem cells may be grown on separate particles. Any combinations of any of these arrangements are also possible, for example, a culture which comprises feeder cells grown on particles, particles with feeder cells and stem cells, and particles with stem cells growing. These combinations may be grown in containers with a feeder layer or without.

Arrangements in which feeder cells are absent or not required are also possible. For example, the cells may be grown in medium conditioned by feeder cells or stem cells.

Media and Feeder Cells

Media for isolating and propagating pluripotent stem cells can have any of several) different formulas, as long as the cells obtained have the desired characteristics, and can be propagated further.

Suitable sources are as follows: Dulbecco's modified Eagles medium (DMEM), Gibco#11965-092; Knockout Dulbecco's modified Eagles medium (KO DMEM), Gibco#10829-018; 200 mM L'-glutamine, Gibco#15039-027; non-essential amino acid solution, Gibco 11140-050; beta-mercaptoethanol, Sigma#M7522; human recombinant basic fibroblast growth factor (bFGF), Gibco#13256-029. Exemplary serum-containing embryonic stem (ES) medium is made with 80% DMEM (typically KO DMEM), 20% defined fetal bovine serum (FBS) not heat inactivated, 0.1 mM non-essential amino acids, 1 mM glutamine, and 0.1 mM beta-mercaptoethanol. The medium is filtered and stored at 4 degrees C. for no longer than 2 weeks. Serum-free embryonic stem (ES) medium is made with 80% KO DMEM, 20% serum replacement, 0.1 mM non-essential amino acids, 1 mM L-glutamine, and 0.1 mM beta-mercaptoethanol. An effective serum replacement is Gibco#10828-028. The medium is filtered and stored at 4 degrees C. for no longer than 2 weeks. Just before use, human bFGF is added to a final concentration of 4 ng/mL (Bodnar et al., Geron Corp, International Patent Publication WO 99/20741).

The media may comprise Knockout DMEM media (Invitrogen-Gibco, Grand Island, N.Y.), supplemented with 10% serum replacement media (Invitrogen-Gibco, Grand Island, N.Y.), 5 ng/ml FGF2 (Invitrogen-Gibco, Grand Island, N.Y.) and 5 ng/ml PDGF AB (Peprotech, Rocky Hill, N.J.).

Feeder cells (where used) may be propagated in mEF medium, containing 90% DMEM (Gibco#11965-092), 10% FBS (Hyclone#30071-03), and 2 mM glutamine. mEFs are propagated in T150 flasks (Coming#430825), splitting the cells 1:2 every other day with trypsin, keeping the cells subconfluent. To prepare the feeder cell layer, cells are irradiated at a dose to inhibit proliferation but permit synthesis of important factors that support human embryonic stem cells (.about.4000 rads gamma irradiation); Six-well culture plates (such as Falcon#304) are coated by incubation at 37 degrees C. with 1 mL 0.5% gelatin per well overnight, and plated with 375,000 irradiated mEFs per well. Feeder cell layers are typically used 5 h to 4 days after plating. The medium is replaced with fresh human embryonic stem (hES) medium just before seeding pPS cells.

Conditions for culturing other stem cells are known, and can be optimized appropriately according to the cell type. Media and culture techniques for particular cell types referred to in the previous section are provided in the references cited.

Serum Free Media

The methods and compositions described here may include culture of cells such as stem cells in a serum-free medium.

The term "serum-free media" may comprise cell culture media which is free of serum proteins, e.g., fetal calf serum. Serum-free media are known in the art, and are described for example in U.S. Pat. Nos. 5,631,159 and 5,661,034. Serum-free media are commercially available from, for example, Gibco-BRL (Invitrogen).

The serum-free media may be protein free, in that it may lack proteins, hydiolysates, and components of unknown composition. The serum-free media may comprise chemically-defined media in which all components have a known chemical structure. Chemically-defined serum-free media is advantageous as it provides a completely defined system which eliminates variability allows for improved reproducibility and more consistent performance, and decreases possibility of contamination by adventitious agents.

The serum-free media may comprise Knockout DMEM media (Invitrogen-Gibco, Grand Island, N.Y.).

The serum-free media may be supplemented with one or more components, such as serum replacement media, at a concentration of for example, 5%, 10%, 15%, etc. The serum-free media may be supplemented with 10% serum replacement media from Invitrogen-Gibco (Grand Island, N.Y.).

The serum-free medium in which the dissociated or disaggregated embryonic stem cells are cultured may comprise one or more growth factors. A number of growth factors are known in the art, including FGF2, IGF-2, Noggin, Activin A, TGF beta 1, HRG1 beta, LIF, SIP, PDGF, BAFF, April, SCF, Flt-3 ligand, Wnt3A and others. The growth factor(s), may be used at any suitable concentration such as between 1 pg/ml to 500 ng/ml.

Stem Cells

As used in this document, the term "stem cell" refers to a cell that on division faces two developmental options: the daughter cells can be identical to the original cell (self-renewal) or they may be the progenitors of more specialised cell types (differentiation). The 120 stem cell is therefore capable of adopting one or other pathway (a further pathway exists in which one of each cell type can be formed). Stem cells are therefore cells which are not terminally differentiated and are able to produce cells of other types.

Stem cells as referred to in this document may include totipotent stem cells, pluripotent stem cells, and multipotent stem cells. They also specifically include induced pluripotent stem cells (iPS).

Totipotent Stem Cells

The term "totipotent" cell refers to a cell which has the potential to become any Cell type in the adult body, or any cell of the extraembryonic membranes (e.g., placenta). Thus, the only totipotent cells are the fertilized egg and the first 4 or so cells produced by its cleavage.

Pluripotent Stem Cells

"Pluripotent stem cells" are true stem cells, with the potential to make any differentiated cell in the body. However, they cannot contribute to making the extraembryonic membranes which are derived from the trophoblast. Several types of pluripotent stem cells have been found.

Embryonic Stem Cells

Embryonic Stem (ES) cells may be isolated from the inner cell mass (ICM) of the blastocyst, which is the stage of embryonic development when implantation occurs.

Embryonic Germ Cells

Embryonic Germ (EG) cells may be isolated from the precursor to the gonads in aborted fetuses.

Embryonic Carcinoma Cells

Embryonic Carcinoma (EC) cells may be isolated from teratocarcinomas, a tumor that occasionally occurs in a gonad of a fetus. Unlike the first two, they are usually aneuploid. All three of these types of pluripotent stem cells can only be isolated from embryonic or fetal tissue and can be grown in culture. Methods are known in the art which prevent these pluripotent cells from differentiating.

Adult Stem Cells

Adult stem cells comprise a wide variety of types including neuronal, skin and the blood forming stem cells which are the active component in bone marrow transplantation. These latter stem cell types are also the principal feature of umbilical cord-derived stem cells. Adult stem cells can mature both in the laboratory and in the body into functional, more specialised cell types although the exact number of cell types is limited by the type of stem cell chosen.

Multipotent Stem Cells

Multipotent stem cells are true stem cells but can only differentiate into a limited number of types. For example, the bone marrow contains multipotent stem cells that give rise to all the cells of the blood but not to other types of cells. Multipotent stem cells are found in adult animals. It is thought that every organ in the body (brain, liver) contains them where they can replace dead or damaged cells.

Methods of characterising stem cells are known in the art, and include the use of standard assay methods such as clonal assay, flow cytometry, long-term culture and molecular biological techniques e.g. PCR, RT-PCR and Southern blotting.

In addition to morphological differences, human and murine pluripotent stem cells differ in their expression of a number of cell surface antigens (stem cell markers). Markers for stem cells and methods of their detection are described elsewhere in this document (under "Maintenance of Stem Cell Characteristics").

Induced Pluripotent Stem Cells (iPS Cells)

Our methods include the preparation of cells which display enhanced pluripotency, such as induced pluripotent stem cells.

In this document, the term "induced pluripotent stem cells (iPS cells)" refers to cells having similar properties to those of ES cells, and more specifically the term includes undifferentiated cells which are reprogrammed from somatic cells and have pluripotency and proliferation potency.

However, this term is not to be construed as limiting in any sense, and should be construed to have its broadest meaning. Thus, any cell which displays an enhanced level of pluripotency, e.g., by displaying one or more enhanced characteristics of embryonic stem cells, as compared to a cell which has not been treated by the methods described here, may qualify as an iPS cell.

The preparation method of induced pluripotent stem cells with the use of a nuclear reprogramming factor is described in International Publication No. WO2005/80598 A1 (the term "ES-like cell" is used in this publication), and methods for isolating induced pluripotent stem cells are also specifically described. In addition, specific examples of the reprogramming factor and specific examples of the reprogramming method of somatic cells with use of such a reprogramming factor are disclosed in International Publication No. WO2007/069666.

The preparation method of induced pluripotent stem cells from somatic cells by the methods described here is not specifically limited, and any method can be employed as long as the method enables nuclear reprogramming of somatic cells with a nuclear reprogramming factor in the presence of Tbx3 in an environment where somatic cells and induced pluripotent stem cells can grow.

For example, a vector comprising a gene which can express a nuclear reprogramming factor can be used to introduce such a gene into somatic cells, and at either the same or different timing, a recombinant vector which can express Tbx3 can be introduced into the somatic cells. If such vectors are used, two or more genes may be incorporated into a vector to effect simultaneous expression of respective gene products in somatic cells.

When gene(s) and/or Tbx3 are introduced into somatic cells with use of a vector which can express the above gene(s), the expression vector may be introduced into somatic cells that have been cultured on feeder cells, or the expression vector may also be introduced into somatic cells alone. The latter method is sometimes more suitable in order to improve the introduction efficiency of the expression vector.

As to the feeder cells, there may be appropriately used feeder cells for use in culture of embryonic stem cells. Examples thereof can include primary culture cells of 14 or 15 day-mouse embryonic fibroblasts and STO cells of fibroblast cell line, which are treated with either radiation or a drug such as mitomycin C.

The culture of somatic cells introduced with a nuclear reprogramming factor under an appropriate condition leads to autonomous nuclear reprogramming, as a result of which induced pluripotent stem cells can be produced from somatic cells. The process for introducing a gene encoding a nuclear reprogramming factor and/or Tbx3 into somatic cells with use of an expression vector to thereby obtain induced pluripotent stem cells can be performed in accordance with, for example, a method using a retrovirus.

Examples of such methods include methods described in publications such as Takahashi et al., Cell 126:663-76, 2006; Takahashi et al., Cell 131:861-72, 2007; Yu et al., Science 318:1917-20, 2007. When human induced pluripotent stem cells are to be produced, it is desirable to set the cell culture density after the introduction of an expression vector to be lower than normal cases for culturing animal cells. For example, it is possible to keep culturing at a density of $1\times10^4$ to $1\times10^5$ cells/10 cm dish, such as about $5\times10^4$ cells/10 cm dish.

The medium for use in culture is not specifically limited, and can be appropriately selected by those skilled in the art, although for example it is sometimes possible to use a medium suitable for human ES cell culture for the production of human induced pluripotent stem cells. The medium selection and culture condition can be referred to the above publications.

Thus produced induced pluripotent stem cells can be checked with various markers specific to undifferentiated cells, and the means therefor is described in the above publications specifically in detail. For example, some pluripotent cell markers include: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; βIII-tubulin; α-smooth muscle actin (α-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fthl17; Sal14; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); and T-cell lymphoma breakpoint 1 (Tell); DPPA3/Stella; DPPA4. Other markers can include Dnmt3L; Sox15; Stat3; Grb2; SV40 Large T Antigen; HPV16 E6; HPV16 E7, 13-catenin, and Bmi1. Such cells can also be characterized by the down-regulation of markers characteristic of the differentiated cell from which the iPS cell is induced. For example, iPS cells derived from fibroblasts may be characterized by down-regulation of the fibroblast cell marker Thy1 and/or up-regulation of SSEA-3 and 4. It is understood that description is not limited to those markers listed herein, and encompasses markers such as cell surface markers, antigens, and other gene products including ESTs, RNA (including microRNAs and antisense RNA), DNA (including genes and cDNAs), and portions thereof.

Media for Maintaining Pluripotency

Various media capable of retaining undifferentiation property and pluripotency of ES cells and various media incapable of retaining these properties are known in the art, and appropriate combination of these media enables efficient isolation of induced pluripotent stem cells.

The differentiation ability and proliferation potency of thus isolated induced pluripotent stem cells can be readily checked by those skilled in the art, with use of general checking means for ES cells. In addition, colonies of induced pluripotent stem cells may be obtained by growing thus produced induced pluripotent stem cells under an appropriate condition, and the presence of these induced pluripotent stem cells can be identified with reference to the shape of their colonies.

For example, it is known that mouse induced pluripotent stem cells form raised colonies, while human induced pluripotent stem cells form flat colonies. These colony shapes are respectively very similar to those of mouse ES cells and human ES cells, and those skilled in the art are thus able to identify these produced induced pluripotent stem cells with reference to the shape of their colonies.

Sources of Somatic Cells

The type of somatic cell to be reprogrammed by the methods described here is not specifically limited, and any somatic cell can be used. For example, somatic cells derived from any mammal (for example, derived from a mammal such as human, mouse, rat, cattle, sheep, horse, and monkey) can be employed.

Not only embryonic somatic cells but also neonatal somatic cells, matured somatic cells, and tissue stem cells may also be used. In addition, various somatic cells such as skin cells, liver cells, and gastric mucosa cells can be reprogrammed.

For use of induced pluripotent stem cells in therapies against diseases, it may be desirable to use somatic cells isolated from the patient. For example, somatic cells involved in a disease and somatic cells associated with a therapy for a disease may be used.

Uses

The possible uses of cells, which display enhanced or induced pluripotency such as induced pluripotent stem cells, produced by the methods described here is not specifically limited, and these cells can be used for every examination/study to be performed with use of ES cells, and for any disease therapy which utilizes ES cells.

For example, induced pluripotent stem cells obtained by the methods described here can be induced into desired differentiated cells (such as nerve cells, myocardial cells, blood cells and insulin-producing cells) by treatment with retinoic acid, a growth factor such as EGF, or glucocorticoid, so that appropriate tissue can be formed.

Stem cell therapies through autologous cell transplantation can be achieved by returning these differentiated cells or tissue obtained in the above manner, into the patient. However, the application of the induced pluripotent stem cells described here is not to be limited to the abovementioned specific aspects.

Uses

The methods and compositions described here may be employed for various means.

For example, the cells treated by the methods and compositions described her, which display enhanced or induced pluripotency, may be used for a variety of commercially important research, diagnostic, and therapeutic purposes. The treated cells, including stem cells, may be used directly for these purposes, or may be differentiated into any chosen cell type using methods known in the art. Progenitor cells may also be derived from the treated cells, including stem cells.

The differentiated cells or progenitor cells, or both, may be used in place of, or in combination with, the treated cells, including stem cells, for the same purposes. Thus, any use described in this document for treated cells, including stem cells, attaches equally to progenitor cells and differentiated cells derived from the treated cells, including stem cells. Similarly, any uses of differentiated cells will equally attach to those treated cells, including stem cells, for which they are progenitors, or progenitor cells.

The uses for treated cells, including stem cells, etc are generally well known in the art, but will be described briefly here.

Therapeutic Uses

The methods and compositions described here may be used to propagate treated cells, including stem cells, for regenerative therapy. Such cells may be expanded and directly administered into a patient. They may be used for the repopulation of damaged tissue following trauma.

Treated cells, including stem cells, may be used directly, or used to generate ectodermal, mesodermal or endodermal progenitor cell populations, for regenerative therapy. Progenitor cells may be made by ex vivo expansion or directly administered into a patient. They may also be used for the re-population of damaged tissue following trauma.

Thus, hematopoietic progenitor cells may be used for bone marrow replacement, while cardiac progenitor cells may be used for cardiac failure patients. Skin progenitor cells may be employed for growing skin grafts for patients and endothelial progenitor cells for endothelization of artificial prosthetics such as stents or artificial hearts.

Treated cells, including stem cells, may be used as sources of ectodermal, mesodermal or endodermal progenitor cells for the treatment of degenerative diseases such as diabetes, Alzheimer's disease, Parkinson's disease, etc. Treated cells, including stem cells, may be used as sources of mesodermal or endodermal progenitors for NK or dendritic cells for immunotherapy for cancer.

The methods and compositions described here enable the production of ectodermal, mesodermal or endodermal progenitor cells, which may of course be made to further differentiate using methods known in the art to terminally differentiated cell types.

Thus, any uses of terminally differentiated cells will equally attach to those ectodermal, mesodermal or endodermal progenitor cells (or stem cells) for which they are sources.

Treated cells, including stem cells, ectodermal, mesodermal or endodermal progenitor cells and differentiated cells produced by the methods and compositions described here may be used for, or for the preparation of a pharmaceutical composition for, the treatment of a disease. Such disease may comprise a disease treatable by regenerative therapy, including cardiac failure, bone marrow disease, skin disease, burns; degenerative disease such as diabetes, Alzheimer's disease, Parkinson's disease, etc and cancer.

Libraries

For example, populations of undifferentiated and differentiated cells may be used to prepare antibodies and cDNA libraries that are specific for the differentiated phenotype. General techniques used in raising, purifying and modifying antibodies, and their use in immunoassays and immunoisolation methods are described in Handbook of Experimental Immunology (Weir & Blackwell, eds.); Current Protocols in Immunology (Coligan et al., eds.); and Methods of Immunological Analysis (Masseyeff et al., eds., Weinheim: VCH Verlags GmbH). General techniques involved in preparation of mRNA and cDNA libraries are described in RNA Methodologies: A Laboratory Guide for Isolation and Characterization (R. E. Farrell, Academic Press, 1998); cDNA Library Protocols (Cowell & Austin, eds., Humana Press); and Functional Genomics (Hunt & Livesey, eds., 2000). Relatively homogeneous cell populations are particularly suited for use in drug screening and therapeutic applications.

Drug Screening

Treated cells, including stem cells, and differentiated cells may also be used to screen for factors (such as solvents, small molecule drugs, peptides, polynucleotides, and the like) or environmental conditions (such as culture conditions or manipulation) that affect the characteristics of treated cells, including stem cells, or differentiated cells.

Treated cells, including stem cells, may be used to screen for factors that promote pluripotency, or differentiation. In some applications, differentiated cells are used to screen factors that promote maturation, or promote proliferation and maintenance of such cells in long-term culture. For example, candidate maturation factors or growth factors are tested by adding them to cells in different wells, and then determining any phenotypic change that results, according to desirable criteria for further culture and use of the cells.

Particular screening applications relate to the testing of pharmaceutical compounds in drug research. The reader is referred generally to the standard textbook "In vitro Methods in Pharmaceutical Research", Academic Press, 1997, and U.S. Pat. No. 5,030,015), as well as the general description of drug screens elsewhere in this document. Assessment of the activity of candidate pharmaceutical compounds generally involves combining the treated cells, including stem cells, or differentiated cells with the candidate compound, determining any change in the morphology, marker phenotype, or metabolic activity of the cells that is attributable to the compound (compared with untreated cells or cells treated with an inert compound), and then correlating the effect of the compound with the observed change.

The screening may be done, for example, either because the compound is designed to have a pharmacological effect on certain cell types, or because a compound designed to have effects elsewhere may have unintended side effects. Two or more drugs can be tested in combination (by combining with the cells either simultaneously or sequentially), to detect possible drug-drug interaction effects. In some applications, compounds are screened initially for potential toxicity (Castell et al., pp. 375-410 in "In vitro Methods in Pharmaceutical Research," Academic Press, 1997). Cytotoxicity can be determined in the first instance by the effect on cell viability, survival, morphology, and expression or release of certain markers, receptors or enzymes. Effects of a drug on chromosomal DNA can be determined by measuring DNA synthesis or repair. [$^3$H]thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (PP 375-410 in "In vitro Methods in Pharmaceutical Research," Academic Press, 1997) for further elaboration.

Tissue Regeneration

Treated cells, including stem cells, generated according to the methods and compositions described here (and differentiated cells derived therefrom) may be used for therapy, for example tissue reconstitution or regeneration in a individual patient in need thereof. The cells may be administered in a manner that permits them to graft to the intended tissue site and reconstitute or regenerate the functionally deficient area.

Treated cells, including stem cells, or differentiated cells derived therefrom may be used for tissue engineering, such as for the growing of skin grafts. They may be used for the bioengineering of artificial organs or tissues, or for prosthetics, such as stents.

Differentiated cells may also be used for tissue reconstitution or regeneration in a human patient in need thereof. The cells are administered in a manner that permits them to graft to the intended tissue site and reconstitute or regenerate the functionally deficient area.

For example, the methods and compositions described here may be used to modulate the differentiation of treated cells, including stem cells. Differentiated cells may be used for tissue engineering, such as for the growing of skin grafts. Modulation of differentiation of treated cells, including stem cells, may be used for the bioengineering of artificial organs or tissues, or for prosthetics, such as stents.

In another example, neural stem cells are transplanted directly into parenchymal or intrathecal sites of the central nervous system, according to the disease being treated. Grafts are done using single cell suspension or small aggregates at a density of 25,000-500,000 cells per .mu.L (U.S. Pat. No. 5,968,829). The efficacy of neural cell transplants can be assessed in a rat model for acutely injured spinal cord as described by McDonald et al. (Nat. Med. 5:1410, 1999. A successful transplant will show transplant-derived cells present in the lesion 2-5 weeks later, differentiated into astrocytes, oligodendrocytes, and/or neurons, and migrating along the cord from the lesioned end, and an improvement in gate, coordination, and weight-bearing.

Certain neural progenitor cells are designed for treatment of acute or chronic damage to the nervous system. For example, excitotoxicity has been implicated in a variety of conditions including epilepsy; stroke, ischemia, Huntington's disease, Parkinson's disease and Alzheimer's disease. Certain differentiated cells as made according to the methods described here may also be appropriate for treating dysmyelinating disorders, such as Pelizaeus-Merzbacher disease, multiple sclerosis, leukodystrophies, neuritis and neuropathies. Appropriate for these purposes are cell cultures enriched in oligodendrocytes or oligodendrocyte precursors to promote remyelination.

Hepatocytes and hepatocyte precursors prepared using our methods can be assessed in animal models for ability to repair liver damage. One such example is damage caused by intraperitoneal injection of D-galactosamine (Dabeva et al., Am. J. Pathol. 143:1606, 1993). Efficacy of treatment can be determined by immunohistochemical staining for liver cell markers, microscopic determination of whether canalicular structures form in growing tissue, and the ability of the treatment to restore synthesis of liver-specific proteins. Liver cells can be used in therapy by direct administration, or as part of a bioassist device that provides temporary liver function while the subject's liver tissue regenerates itself following fulminant hepatic failure.

Cardiomyocytes may be prepared by inducing differentiation of stem cells by odulation of the MAP kinase pathway for example with SB203580, a specific p38 MAP kinase inhibitor, as described in Graichen et al (2007). The efficacy of such cardiomyocytes may be assessed in animal models for cardiac cryoinjury, which causes 55% of the left ventricular wall tissue to become scar tissue without treatment (Li et al., Ann. Thorac. Surg. 62:654, 1996; Sakai et al., Ann. Thorac. Surg. 8:2074, 1999, Sakai et al., J. Thorac Cardiovasc. Surg. 118: 715, 1999). Successful treatment will reduce the area of the scar, limit scar expansion, and improve heart function as determined by systolic, diastolic, and developed pressure. Cardiac injury can also be modeled using an embolization coil in the distal portion of the left anterior descending artery (Watanabe et al., Cell Transplant. 7:239, 1998), and efficacy of treatment can be evaluated by histology and cardiac function. Cardiomyocyte preparations can be used in therapy to regenerate cardiac muscle and treat insufficient cardiac function (U.S. Pat. No. 5,919,449 and WO 99/03973).

Cancer

Treated cells, including stem cells, generated according to the methods and compositions described here and differentiated cells derived therefrom may be used for the treatment of cancer.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia.

More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer. Further examples are solid tumor cancer including colon cancer, breast cancer, lung cancer and prostrate cancer, hematopoietic malignancies including leukemias and lymphomas, Hodgkin's disease, aplastic anemia, skin cancer and familiar adenomatous polyposis. Further examples include brain neoplasms, colorectal neoplasms, breast neoplasms, cervix neoplasms, eye neoplasms, liver neoplasms, lung neoplasms, pancreatic neoplasms, ovarian neoplasms, prostatic neoplasms, skin neoplasms, testicular neoplasths, neoplasms, bone neoplasms, trophoblastic neoplasms, fallopian tube neoplasms, rectal neoplasms, colonic neoplasms, kidney neoplasms, stomach neoplasms, and parathyroid neoplasms. Breast cancer, prostate cancer, pancreatic cancer, colorectal cancer, lung cancer, malignant melanoma, leukaemia, lympyhoma, ovarian cancer, cervical cancer and biliary tract carcinoma are also included.

Treated cells, including stem cells, generated and optionally differentiated according to the methods and compositions described here may also be used in combination with anticancer agents such as endostatin and angiostatin or cytotoxic agents or chemotherapeutic agent. For example, drugs such as such as adriamycin, daunomycin, cis-platinum, etoposide, taxol, taxotere and alkaloids, such as vincristine, and antimetabolites such as methotrexate. The term "cytotoxic agent" as used herein refers to a substance that inhibits or prevents the function of cells and/or causes destruction of cells. The term is intended to include radioactive isotopes (e.g. I, Y, Pr), chemotherapeutic agents, and toxins such as enzymatically active toxins of bacterial, fungal, plant or animal origin, or fragments thereof.

Also, the term includes oncogene product/tyrosine kinase inhibitors, such as the bicyclic ansamycins disclosed in WO 94/22867; 1,2-bis(arylamino) benzoic acid derivatives disclosed in EP 600832; 6,7-diamino-phthafazin-1-one derivatives disclosed in EP 600831; 4,5-bis(arylamino)-phthalimide derivatives as disclosed in EP 516598; or peptides which inhibit binding of a tyrosine kinase to a SH2-containing substrate protein (see WO 94/07913, for example). A "chemotherapeutic agent" is a chemical compound useful in the treatment of cancer. Examples of chemotherapeutic agents include Adriamycin, Doxorubicin, 5-Fluorouracil (5-FU), Cytosine arabinoside (Ara-C), Cyclophosphamide, Thiotepa, Busulfan, Cytoxin, Taxol, Methotrexate, Cisplatin, Melphalan; Vinblastine, Bleomycin, Etoposide, Ifosfamide, Mitomycin C, Mitoxantrone, Vincristine, VP-16, Vinorelbine, Carboplatin, Teniposide, Daunomycin, Caminomycin, Aminopterin, Dactinomycin, Mitomycins, Nicotinamide, Esperamicins (see U.S. Pat. No. 4,675,187), Melphalan and other related nitrogen mustards, and endocrine therapies (such as diethylstilbestrol (DES), Tamoxifen, LHRH antagonizing drugs, progestins, anti-progestins etc).

Further Aspects

Further aspects and embodiments of the invention are now set out in the following numbered; it is to be understood that the invention encompasses these aspects.

We describe methods for efficiently preparing induced pluripotent stem cells. We describe methods for achieving efficient preparation of induced pluripotent stem cells in the presence of Tbx3. We describe methods for efficient preparation of induced pluripotent stem cells with a nuclear reprogramming factor, including Tbx3. We describe methods for efficient preparation of induced pluripotent stem cells with a nuclear reprogramming factor in the presence of increased Tbx3 as compared to the level present in the somatic cell prior to nuclear reprogramming. We describe such methods in which the nuclear reprogramming factor does not include c-Myc.

We describe a method of preparing induced pluripotent stem cells, comprising nuclear reprogramming a somatic cell with nuclear reprogramming factor and Tbx3, in which Tbx3 increases efficiency of the nuclear reprogramming of the somatic cell compared to nuclear reprogramming of the somatic cell with the nuclear reprogramming factor in the absence of Tbx3.

We describe such a method, in which Tbx3 is expressed in embryonic stem cells at a higher level than in somatic cells.

We describe such a method, in which a gene encoding the nuclear reprogramming factor and/or Tbx3 is introduced into a somatic cell.

We describe such a method, in which a vector comprising the gene and/or a vector encoding Tbx3 is introduced into a somatic cell.

We describe such a method, in which the vector comprising the gene or encoding Tbx3 is a retroviral vector.

We describe such a method, in which the gene is selected from an Oct family gene, a Klf family gene, and a Sox family gene.

We describe such a method, in which the gene is selected from Oct3/4, Klf4, and Sox2.

We describe such a method, in which the nuclear reprogramming factor comprises Oct3/4, Klf4, and Sox2.

We describe such a method, in which Tbx3 is introduced into a somatic cell as a nucleic acid.

We describe such a method, in which the nuclear reprogramming factor does not include c-Myc.

In an alternative embodiment, the nuclear reprogramming factor includes a Myc family gene, such as c-Myc.

We describe such a method, in which the nuclear reprogramming factor comprises an Oct family gene member, a Sox family gene member, and a Klf family gene member.

We describe such a method, in which the nuclear reprogramming factor comprises a Klf family gene, and an Oct family gene.

We describe such a method, in which the nuclear reprogramming factor further comprises a Sox family gene.

We describe such a method, in which the nuclear reprogramming factor further comprises a Sox family gene.

We describe such a method, in which the nuclear reprogramming factor comprises KLF4 and OCT3/4.

We describe such a method, in which the nuclear reprogramming factor excludes a Sox family gene.

We describe such a method, in which the nuclear reprogramming factor excludes a Myc family gene.

We describe such a method, where the somatic cell comprises a plurality of somatic cells.

We describe a method of increasing the efficiency of nuclear reprogramming comprising: adding a nuclear reprogramming factor and Tbx3 to a somatic cell so that the number of induced pluripotent stem cells produced is greater than in the absence of the added Tbx3.

We describe an induced pluripotent stem cell induced by reprogramming a somatic cell, in which the reprogramming is performed by adding Tbx3 and in the absence of eggs, embryos, or embryonic stem (ES) cells.

We describe such an induced pluripotent stem cell, in which the induced pluripotent stem cell is a human cell.

We describe an induced pluripotent stem cell obtained by a method of preparing induced pluripotent stem cells, comprising nuclear reprogramming a somatic cell with nuclear reprogramming factor and Tbx3, in which the Tbx3 increases efficiency of the nuclear reprogramming of the somatic cell compared to nuclear reprogramming of the somatic cell with the nuclear reprogramming factor in the absence of Tbx3.

We describe an pluripotent stem cell obtained by a method of increasing the efficiency of nuclear reprogramming comprising: adding a nuclear reprogramming factor and Tbx3 to a somatic cell so that the number of induced pluripotent stem cells produced is greater than in the absence of the added Tbx3.

We describe somatic cell derived by inducing differentiation of any of the above pluripotent stem cells.

We further describe a method of preparing an induced pluripotent stem cell from a somatic cell, comprising nuclear reprogramming the somatic cell with a nuclear reprogramming factor and Tbx3, in which Tbx3 increases efficiency of the nuclear reprogramming of the somatic cell compared to nuclear reprogramming of the somatic cell with the nuclear reprogramming factor in the absence of Tbx3, and in which the nuclear reprogramming factor comprises at least (i) an Oct family gene, (ii) an Oct family gene and a Klf family gene, (iii) an Oct family gene and a Nanog gene, or (iv) an Oct family gene, Klf family gene, and a Myc family gene, but it does not comprise a Sox family gene.

We yet further describe a method of increasing the efficiency of nuclear reprogramming for inducing an induced pluripotent stem cell from a somatic cell, comprising subjecting the somatic cell to nuclear reprogramming with the nuclear reprogramming factor in the presence of Tbx3, so that the number of induced pluripotent stem cells produced is greater than in the absence of Tbx3, in which Tbx3 increases efficiency of the nuclear reprogramming of the somatic cell compared to nuclear reprogramming of the somatic cell with the nuclear reprogramming factor in the absence of Tbx3, and in which the nuclear reprogramming factor comprises at least (i) an Oct family gene, (ii) an Oct family gene and a Klf family gene, (iii) an Oct family gene and a Nanog gene, or (iv) an Oct family gene, Klf family gene, and a Myc family gene, but it does not comprise a Sox family gene.

We describe each of such methods, in which the Tbx3 is expressed in embryonic stem cells at a higher level than in somatic cells.

We describe each of such methods, in which the Oct family gene is an Oct3/4 gene, the Klf family gene is a Klf4 gene, the Myc family gene is a c-Myc gene, or the Sox family gene is a Sox2 gene.

We describe each of such methods, in which the nuclear reprogramming factor is (i) Oct3/4 gene, (ii) a combination of an Oct3/4 gene and a Klf4 gene, (iii) a combination of an Oct3/4 gene and a Nonog gene, or (iv) a combination of an Oct3/4 gene, a Klf4 gene and a c-Myc gene.

We describe each of such methods, in which the nuclear reprogramming factor is introduced in the form of a vector comprising DNA encoding the nuclear reprogramming factor, into the somatic cell.

We describe each of such methods, in which the Tbx3 is introduced in the form of a vector comprising DNA encoding Tbx3 into the somatic cell.

The somatic cell may comprise a human somatic cell.

EXAMPLES

Example 1

Materials and Methods—Cell culture and Transfection

All cell cultures were maintained at 37° C. with 5% $CO_2$. The culture of mouse R1 and D3 ESCs was described previously[25].

HEK293T cells were maintained in DMEM supplemented with 10% FBS and penicillin/streptomycin.

Transfection of plasmids into mouse ESCs and HEK293 cells was performed using Lipofectamine 2000 (Invitrogen).

Plat-E packaging cells (Cell Biolabs, INC), which were used to produce retrovirus, were maintained according to the manufacturer's guide.

Example 2

Materials and Methods—Plasmid Construction, Viral Packaging and Infection

Coding sequences of Tbx3 were amplified from mouse ESCs by RT-PCR and cloned into pLenti6-UBC (Invitrogen) and pMXs vectors; Oct4, Sox2, Klf4, c-Myc in pMXs were obtained from Addgene; Esrrb was obtained from Feng et al[7].

The retrovirus and lentivirus were generated as previously described[1,26].

For the generation of iPS cells, equal amounts of virus encoding different combination of factors were applied to $5\times10^4$ plated MEFs in 10 $cm^2$ dishes in 10% FBS DMEM media "containing 8 ng polybrene. After 24 h, inactivated feeder cells and fresh media were" added, and the culture was then maintained for up to 21 days. For RNA interference (RNAi) design and construction of plasmids for shRNA synthesis, 19 base-pair gene-specific regions were designed based on the algorithm of Reynolds et al[27].

Oligonucleotides were cloned into pSuper.puro (Oligoengine). All sequences were analyzed by BLAST to ensure specificity.

Example 3

Materials and Methods—Cell Fusion

For PEG-mediated fusions, cells of each type (~$1\times10^6$) were mixed in serum-free DMEM, pelleted, and the supernatant removed. The pellet was resuspended in 300 μl of 50% w/v PEG1500, and left for 3 min with occasional tapping to mix.

Then, 2 ml of medium was added and the cells were spun down, and supernatant discarded. The pellet was resuspended in ESC medium and plated on 10 $cm^2$ dishes. Puromycin (1 μg $ml^{-1}$) and Neomycin (300 mg $ml^{-1}$) were added after 24 h.

Example 4

Materials and Methods—Gene Expression Microarray and Analysis

Cells were rinsed twice in ice-cold PBS. Total RNA was extracted using Trizol (Invitrogen) and column-purified with RNeasy kits (Qiagen).

Expression profiling of coding genes was carried out using Illumina MouseRef-8v1.1 BeadArrays as per manufacturer's instructions. Total chip data is deposited for public access with GEO repository accession number: updating in process.

All data were subtracted from background intensities and were normalized across chips using the cross-correlation method[28]. The normalized data were first $\log_2$ transformed and then subtracted from the mean of the median intensities of the two groups (i.e. Nanog OE with control vector, Tcf3 RNAi with control RNAi).

Prior to clustering, the data were further sorted based on direct targets of Nanog or Tcf3, and subsequently arranged in the descending order of the fold change. The clustering tree was generated using hierarchical clustering with average linkage.

Example 5

Materials and Methods—Mouse Molecular Genetics

Oct4-GFP transgenic mice (Jackson's Lab, stock no. 004654) were used for MEF isolation at E13.5.

Albino embryos were isolated at 2-cell stage, matured to 4-8-cell stage and microinjected with iPS cells using the Piezo Micro Manipulator (PMAS-CT150, PMM) under the fluorescent microscope (Olympus) to generate chimeras. Injected embryos were cultured in KSOM media (Specialty Media) to the blastocyst stage and then transferred to the uterine horns of E2.5 pseudopregnant $F_1$ (CBA×C57BL/6J) females. Chimeric embryos were harvested at E13.5 for analysis of GFP expression in the gonads.

Example 6

Materials and Methods—Tetraploid Complementation

Tetraploid (4n) embryos were generated using 2-cell fusion by Electro cell manipulator (ECM 2001, BTX Har ard Apparatus) and incubated in KSOM till 4-8 cell stage prior to aggregation with iPS cells. The zona pellucida of the tetraploid 4-8 cell stage embryos were removed by brief exposure to acid Tyrode's solution. Three tetraploid embryos and ~40 iPS cells were aggregated in a single well, and incubated in KSOM medium for 24 h to form a morula or blastocyst[16,17].

Approximately 10-14 embryos were transferred into the uterus (for blastocysts) or oviducts (for morulas) of CBAB6$F_1$ pseudopregnent mice.

Example 7

Materials and Methods—Differentiation of ESCs

Mouse ESCs were grown in ESC medium without LIF plus the addition of all-trans retinoic acid (RA; 100 nM), maintained on 0.1% gelatin-coated plates with culture medium replenished every 24 h. In vivo differentiation of ESCs was performed in SCID mice.

Example 8

Materials and Methods—Tumorigenicity in SCID Mice

Female SCID mice 6-8 weeks old were housed under pathogen-free conditions in a temperature controlled room on 12/12 h light/dark schedule with food and water ad libitum.

All procedures involving animals and their care were in accordance with national and international regulations.

$5\times10^6$ cells from each condition were injected subcutaneously into the lower back of the mice. Five mice were used for each condition. At three weeks, the mice were euthanized and the tumors extracted.

For immunohistochemistry, four μm thick paraffin-embedded tumor tissue sections were stained with haematoxylin and eosin.

Example 9

Materials and Methods—Protein Extraction and Western Blotting

To obtain protein extracts, cells were scraped from culture dishes in chilled PBS, centrifuged at 450×g for 4 min at 4° C., washed again in PBS, and incubated for 20 min in ice cold lysis buffer containing freshly added protease inhibitors (0.5 mM phenylmethylsulfonyl fluoride, 10 μg $ml^{-1}$ leupeptin, 2 μg $ml^{-1}$ aprotonin).

Lysates were cleared by centrifugation at 12,100×g, 4° C. for 10 min and the supernatant was snap frozen in liquid nitrogen. Protein concentrations were determined using Bradford Dye (Bio-Rad). 10 μg total protein was separated by SDS-PAGE on NuPAge gels (Invitrogen), and transferred to Hybond-P PVDF membrane (GE Healthcare).

The membrane was probed with specific antibodies and antibody-protein complex detected by HRP-conjugated antibodies and ECL-Plus (Amersham Biosciences).

Example 10

Materials and Methods—RNAi Assay

The shRNA construct for Tbx3 was designed to target 19-base-pair (bp) transcript-specific regions. The sequence targeted by the shRNAs is as following:

```
                                   (SEQ ID NO.: 6)
GAGCCAACGATATCCTGAA
```

(SEQ ID NO.: 6)

The control shRNA sequence is GATGAAATGGGTAAGTACA (SEQ ID NO.: 7), which targets the luciferase gene. These oligonucleotides were cloned into pSuperpuro (BglII and HindIII sites; Oligoengine). The pSuperpuro plasmid expresses puromycin as the selective marker. Transfection of shRNA plasmids was performed using Lipofectamine 2000 (Invitrogen) according to the manufacturer's instructions.

Briefly, 2 μg of plasmids were transfected into ES cells on 60-mm plates. Puromycin (Sigma) selection was introduced 1 day after transfection at 1.0 μg/ml, and maintained for 3 days prior to harvesting.

Example 11

Materials and Methods—ChIP and ChIP-Seq Assay

ChIP assay was carried out as described previously (Jiang, J. et al. A core Klf circuitry regulates self-renewal of embryonic stem cells. *Nat Cell Biol* 10, 353-60 (2008)).

Briefly, the cells were cross-linked with 1% (w/v) formaldehyde for 10 min at room temperature, and formaldehyde was then inactivated by the addition of 125 mM glycine. Chromatin extracts containing DNA fragments with an average size of 500 bp were immunoprecipitated using anti-Tbx3 antibody (sc-31657; Santa Cruz Biotechnology).

The ChIP-enriched DNA was then decrosslinked and analyzed by realtime PCR using the ABI PRISM 7900 sequence detection system and SYBR green master mix. For ChIP-seq assay, 10 ng of ChIP DNA was end polished with T4 DNA polymerase and kinase. An A base was added to the polished DNA fragments followed by the Qiaquick columriclean up. Solexa adaptors were ligated to the ChIP DNA fragments and enriched by 15 cycles of PCR amplification.

150-300 bp size fractions were selectively cut out from the gel and eluted by Qiagen gel extraction kit. The extracted DNA was quantified by picogreen assay and subjected to Solexa sequencing according to the manufacturer's instruction. Tbx3 binding peak calling to mouse reference genome was done by MACS program.

Colocalization analysis of Tbx3 binding sites with sites of other TFs was done using ChIP-seq data (Chen, X. et al. Integration of external signaling pathways with the core transcriptional network in embryonic stem cells. *Cell* 133, 1106-17 (2008)). 200 bp distance between ChIP-seq peaks was used to count event of TF co-occurrence.

Example 12

Materials and Methods—Southern Hybridization

Genomic DNA isolated from iPS cell clones, or ESCs (WT) was digested with restriction enzymes, separated on an agarose gel, transferred to a nylon membrane, and hybridized with a cDNA probe for Oct4, Sox2 Klf4 or Tbx3. Oct4: SalI+EcoRI; Forward primer—AAAGCAACTCAGAGGGAACC (SEQ ID NO.: 8); Reverse primer—GGCAGAGGAAAGGATACAGC (SEQ ID NO.: 9)

Sox2: BamHI+EcoRI; Forward primer—AGAACCCCAAGATGCACAAC (SEQ ID NO.: 10); Reverse primer—AGTGGGAGGAAGAGGTAACCA (SEQ ID NO.: 11) Klf4: BamHI+HinDIII; Forward primer—TTTGTGCTGAAGGCGTCTCT (SEQ ID NO.: 12); Reverse primer—TGTGTGTTTGCGGTAGTGC (SEQ ID NO.: 13)

Tbx3: ClaI+BamHI; Forward primer—AGAGTGTTTGAGGAGAGGCA (SEQ ID NO.: 14); Reverse primer—TAGGGGTAAGGAAACAGGCT (SEQ ID NO.: 15)

Example 13

Results—Loss of Tcf3 Enhances Fusion-Mediated Reprogramming of Somatic Hybrid Cells To demonstrate that loss of Tcf3 enhances fusion-mediated reprogramming of somatic hybrid cells, we used polyethyleneglycol (PEG) to generate fusion hybrids between Nanog over-expressing (OE) or Tcf3 RNAi ESCs that were neomycin-resistant ($Neo^R$), and primary MEFs that were puromycin-resistant ($Puro^R$).

Figure 1A:
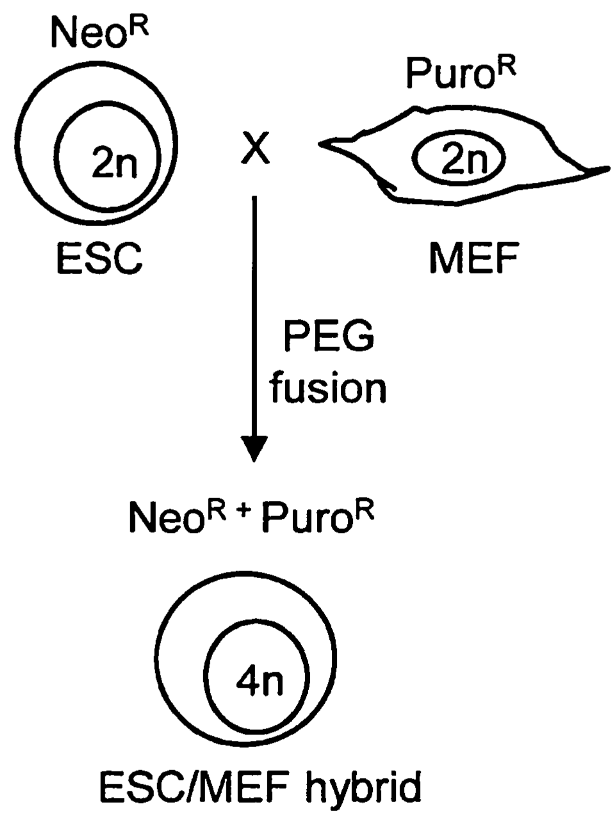
FIG. 1A to FIG. 1F are figure showing that global gene expression profiling reveals Tbx3 aids cell fusion-mediated reprogramming.

After fusion, the plated cells were double selected with neomycin and puromycin (FIG. 1A). Under these conditions, only reprogrammed ESC/MEF hybrids can survive.

Figure 1B:
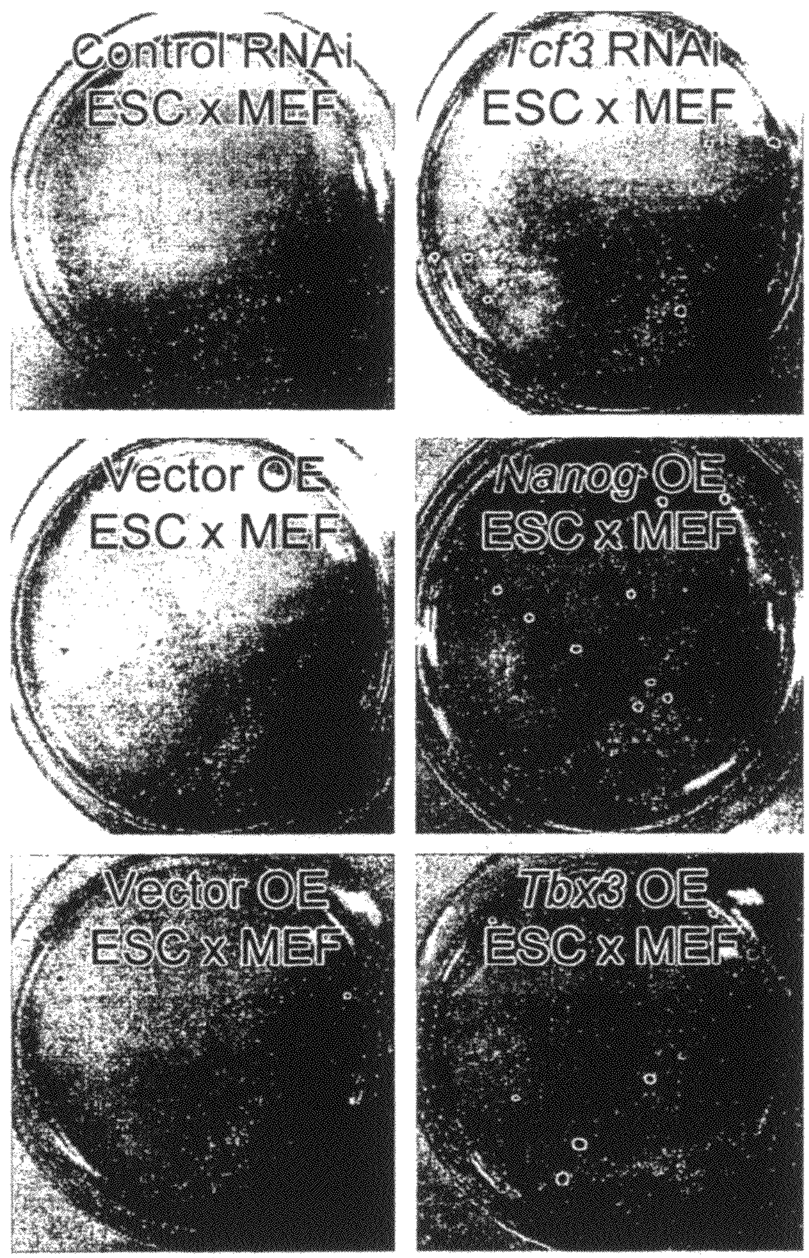
Figure 1C:
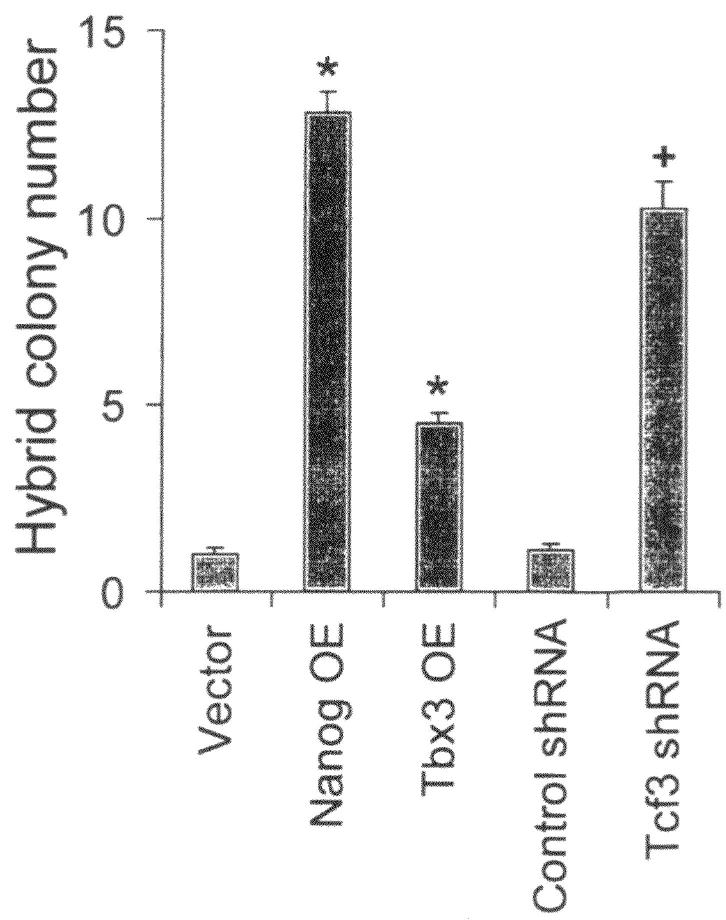
Figure 5:
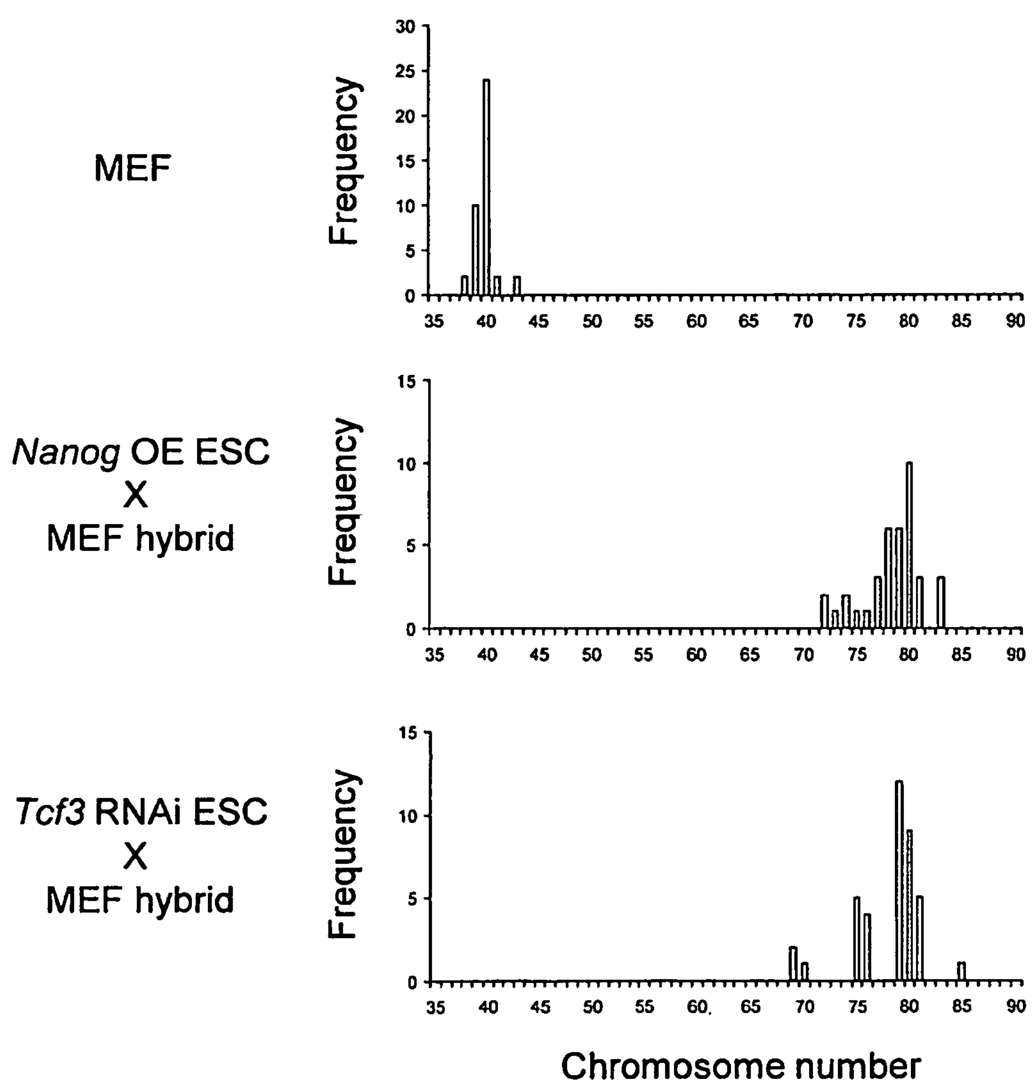
FIG. 5 is a diagram showing karyotype analyses of ESC/MEF hybrid cells. Primary MEFs showed a normal diploid karyotype, n=40 at metaphase. Nanog OE ESC/MEF and Tcf3 RNAi ESC/MEF hybrids were tetraploid with the median chromosome count at 80. A total of 20 metaphase spreads were analyzed for each condition.

Consistent with previous observations, Nanog OE ESCs showed enhance reprogramming efficiency, compared to control (FIGS. 1B & C). Using Tcf3-deficient ESC lines, there was also a marked increase in the number of hybrid clones (FIGS. 1B & C). Karyotype analysis confirmed that these were tetraploid (FIG. 5).

Figure 6:
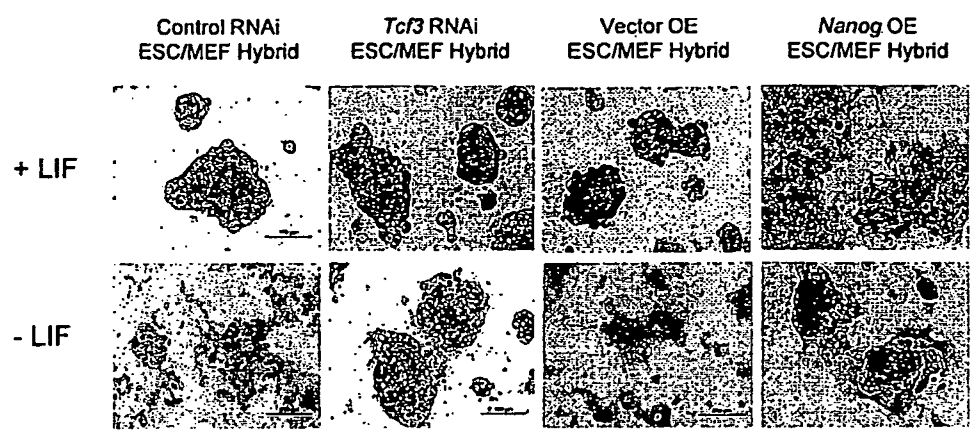
FIG. 6 is a diagram showing that Nanog OE and Tcf3 RNAi ESC/MEF hybrids resemble parental ESC lines. Nanog OE and Tcf3 RNAi ESCs were able to propagate in the absence of LIF where wild-type ESCs would differentiate (Tam, W. L. et al. T-cell factor 3 regulates embryonic stem cell pluripotency and self-renewal by the transcriptional control of multiple lineage pathways. *Stem Cells* 26, 2019-31 (2008); Silva, J., Chambers, I., Pollard, S. & Smith, A. Nanog promotes transfer of pluripotency after cell fusion. *Nature* 441, 997-1001 (2006)). The derived ESC/MEF hybrids from these cells were also able to grow without LIF, whereas control hybrid cells could not. Undifferentiated ESCs were alkaline phosphatase positive (Red). Scale bar=100 μm.
Figure 7:
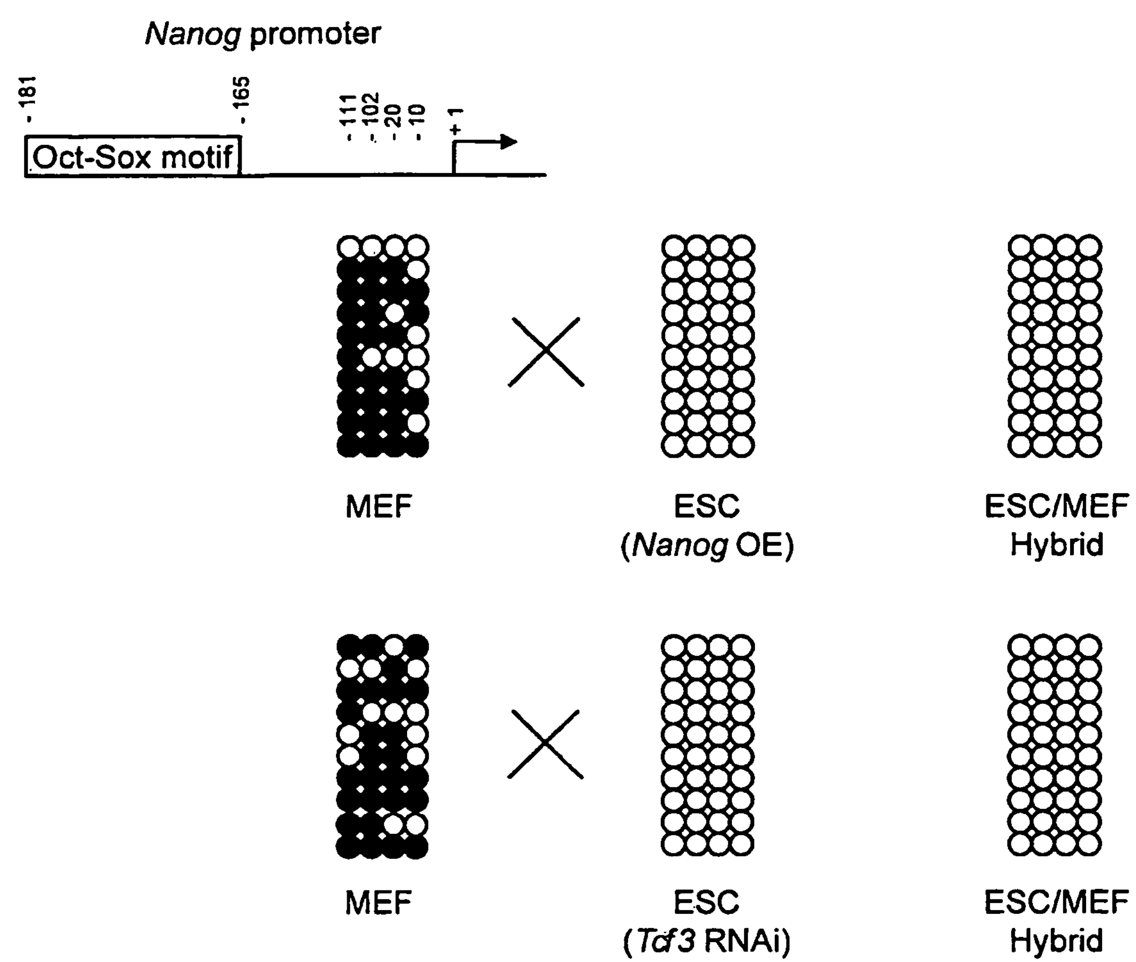
FIG. 7 is a diagram showing epigenetic analysis of Nanog promoter. The Nanog proximal promoter of MEF was highly methylated at CpG sites, and unmethylated in ESCs. Upon cell fusion, ESC/MEF hybrids derived from both Nanog OE and Tcf3 RNAi ESCs showed complete demethylation of the MEF Nanog promoter, resulting in unmethylated CpG sites in the tetraploid cells. Black circle represents a methylated CpG site, while uncolored circle represents unmethylated.
Figure 8:
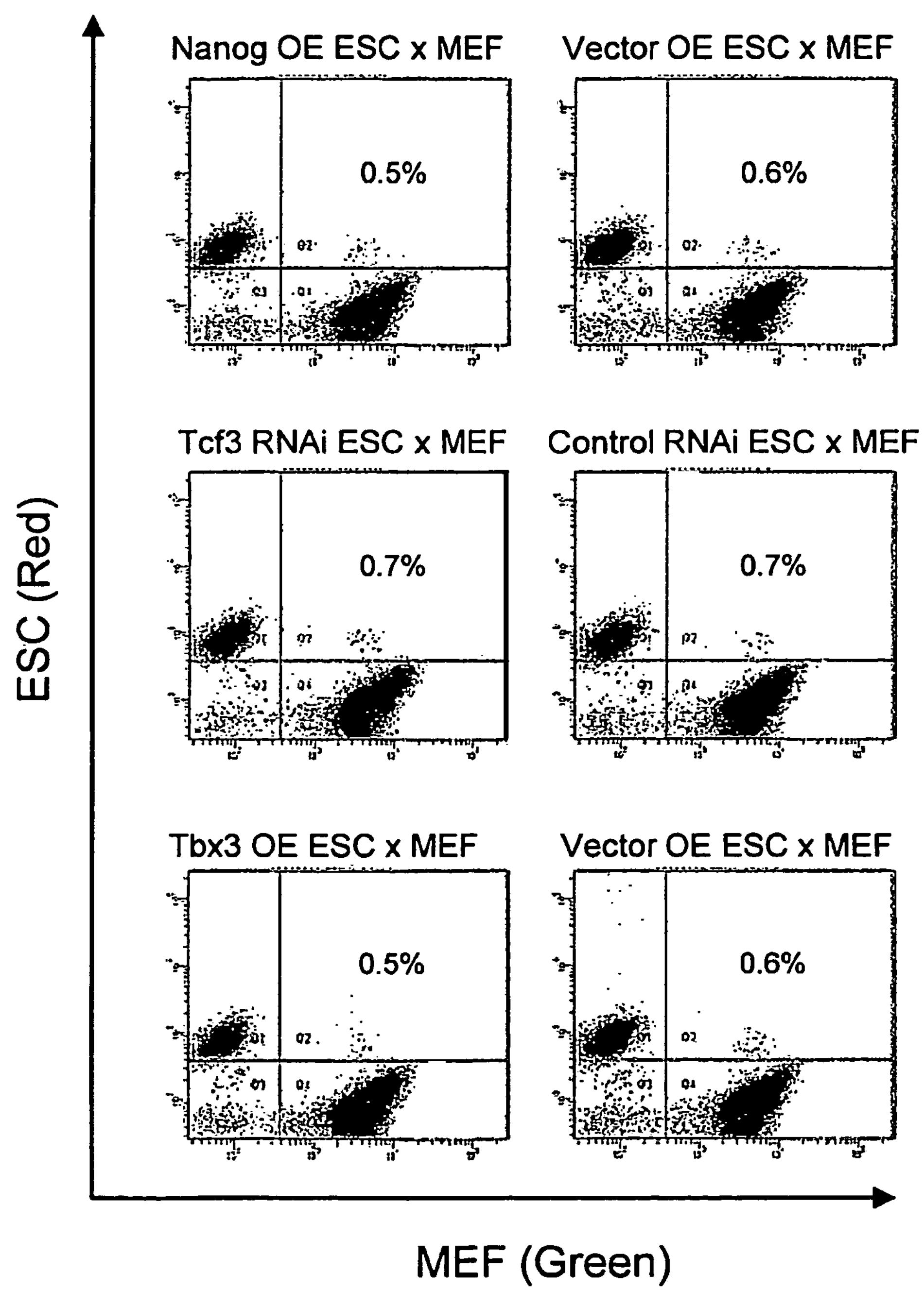
FIG. 8. FACS analyses of the frequency of cell fusion events. To eliminate the possibility that enhanced reprogramming could be due to increased cell fusion events as a result of genetic manipulation, we tracked cell fusion efficiency in modified versus control ES cells. Modified ESCs (Nanog OE, Tbx3 OE or Tcf3 RNAi) and MEFs were labeled with the florescent dyes SNARF-1 and CDFA-SE respectively, followed by cell fusion and plating. After 24 hours, the proportion of labeled cells was analyzed by FACS. In all three modified ESC lines which were fused with MEFs, there was no difference in the percentage of dual dye labeling compared with control ESCs.

We showed these hybrids to possess properties similar to the parental modified ESC lines, including their response to the lack of leukemia inhibitory factor (LIF) and epigenetic reprogramming of the Nanog promoter (FIG. 6 and FIG. 7). We also eliminated the possibility that the improvement in reprogramming frequency could be attributed to increased cell fusion events[13] (FIG. 8).

Example 14

Results—Tbx3 is a Shared Downstream Mediator of Nanog and Tcf3

We examined the repertoire of genes elevated in Nanog OE and Tcf3 RNAi ESCs that could suggest a shared downstream mediator.

Figure 1D:
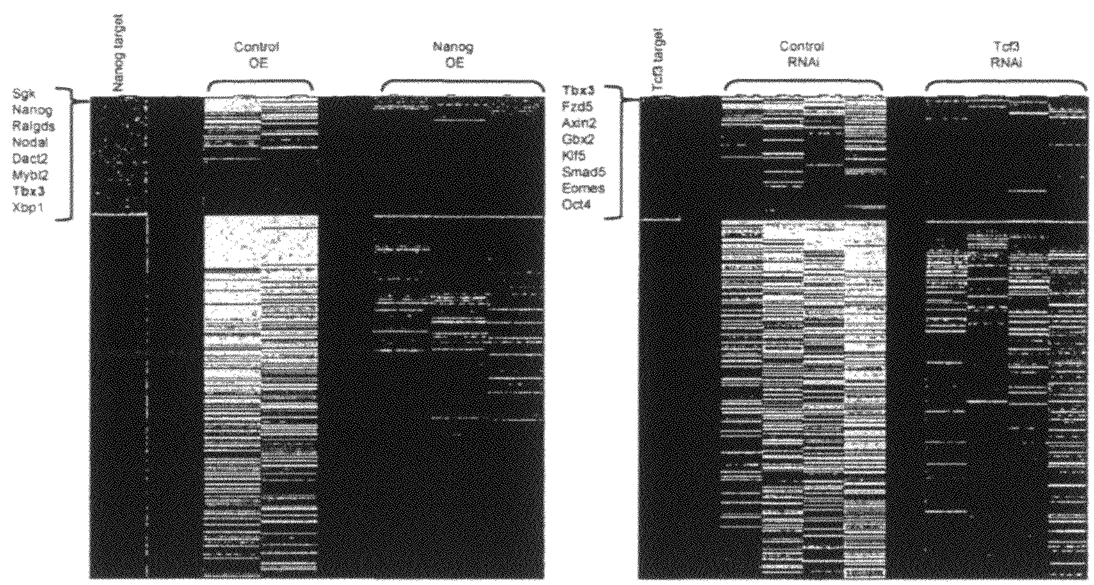
Figure 9A:
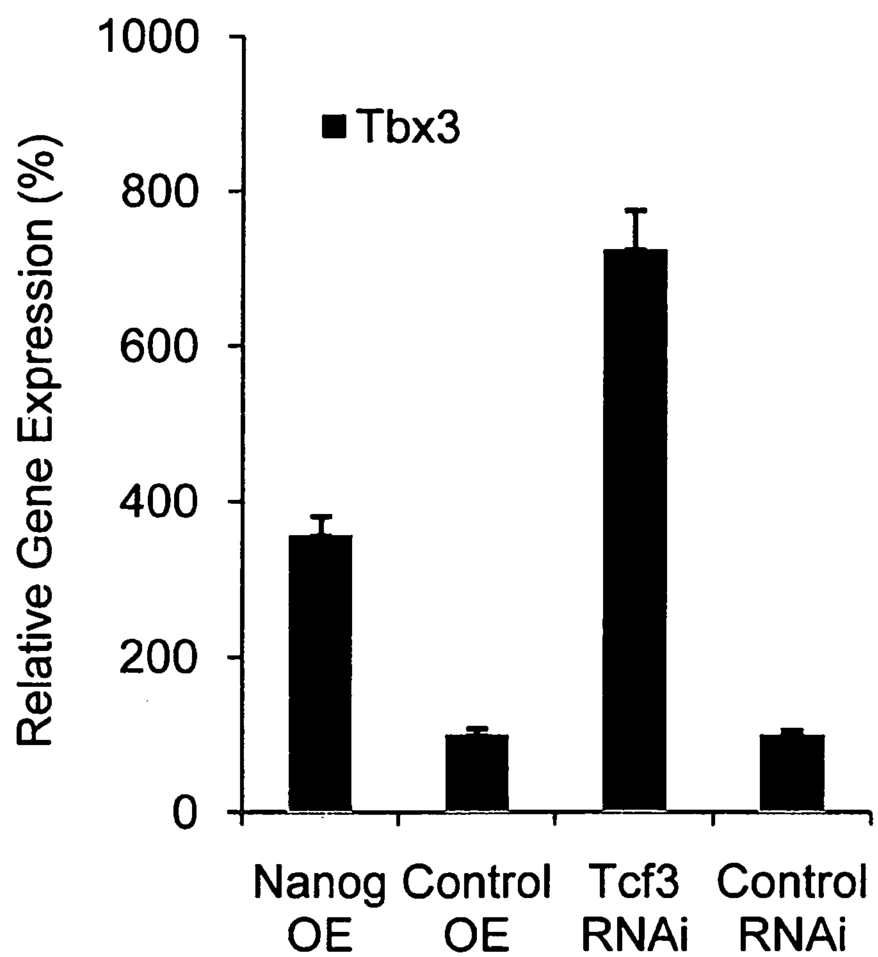
FIG. 9A is a diagram showing expression changes of Tbx3 as measured by qPCR. Both Nanog OE and Tcf3 RNAi knockdown in ESCs upregulated the levels of Tbx3, confirming microarray data shown in FIG. 1D; n=3; error bars represent s.e.m.

The intersected gene expression profiles of these two cell lines revealed a handful of genes such as Daz1, Fzd10, Hal, 4930502E18Rik, and Erf that were upregulated in both conditions. Strikingly, Tbx3, an ESC-associated transcription factor that has reported roles in sustaining pluripotency[15] was strongly elevated (FIG. 1D and FIG. 9A).

Figure 1E:
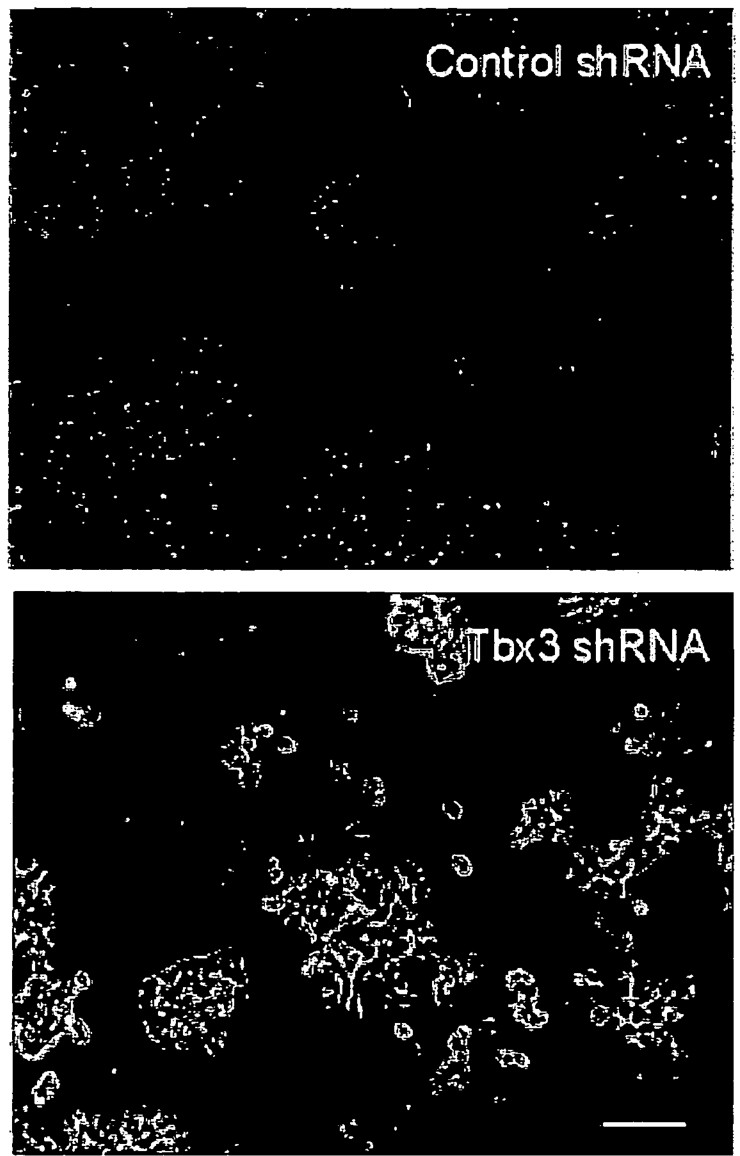
Figure 1F:
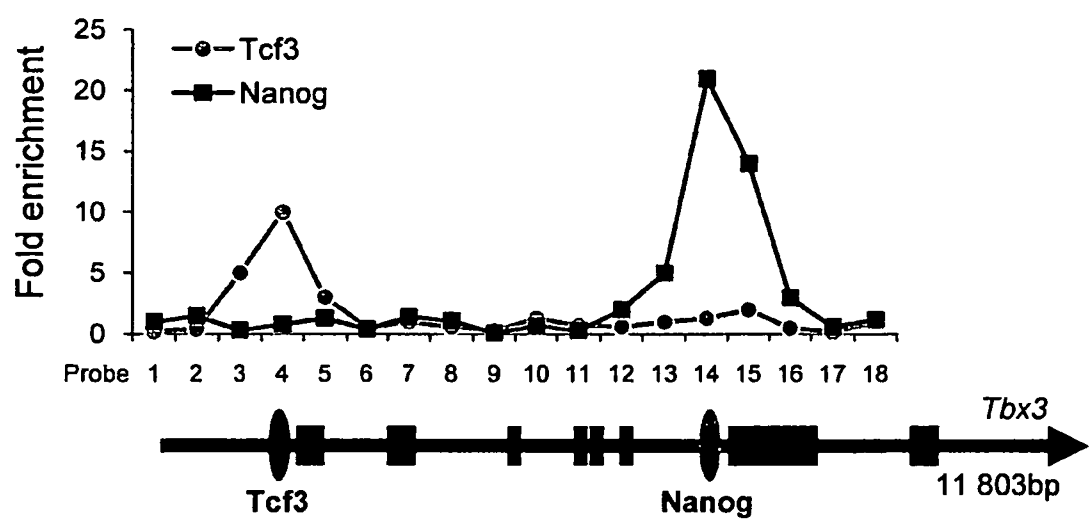

RNAi knockdown of Tbx3 in ESC induced striking differentiation (FIG. 1E), with the concomitant downregulation of pluripotency-associated genes. Tbx3 is also directly bound by both Nanog and Tcf3 (FIG. 1F). In reprogrammed ESC/MEF hybrids, Tbx3 levels remained highly elevated (FIG. 9A).

Figure 9B:
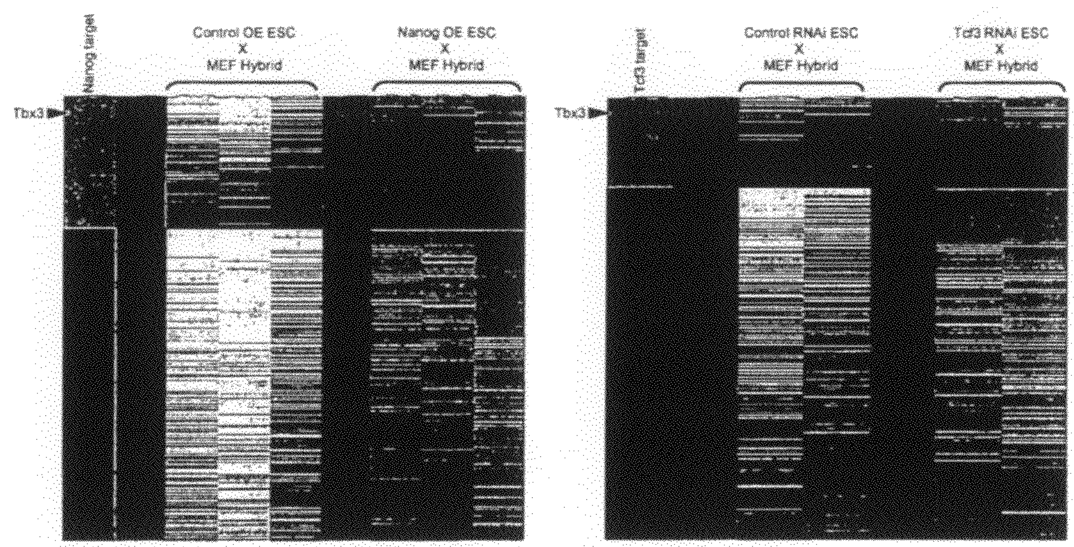
FIG. 9B is a diagram showing gene expression profiling of ESC/MEF hybrid clones. Hybrids obtained from MEF fusion with Nanog OE or Tcf3 RNAi ESCs were compared to control ESC/MEF hybrids. Of all genes up-regulated in Nanog OE or Tcf3 RNAi ESC/MEF hybrids, Tbx3 was among the most elevated genes. The red bars in the left-most column of each heat-map indicate genes which are direct targets of Nanog or Tcf3.
Figure 10:
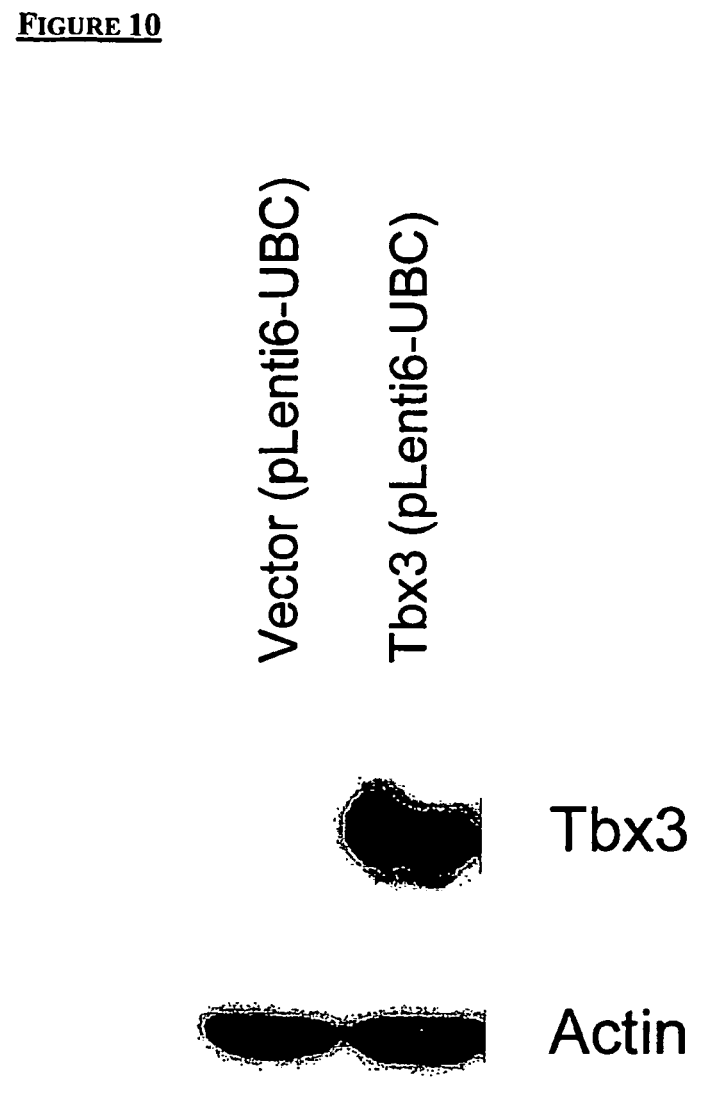

To test the role of Tbx3 in cell fusion-mediated reprogramming, we generated stable $Neo^R$ Tbx3 over-expressing ESC lines (FIG. 10), followed by fusion with MEFs. Indeed, there was an increase in the number of hybrids with Tbx3 OE ESCs compared to control (FIGS. 1B & C). We again eliminated enhanced cell fusion as a mechanism (FIG. 9).

Example 15

Results—Tbx3 Improves Reprogramming Efficiency of iPS Cells

Figure 2A:
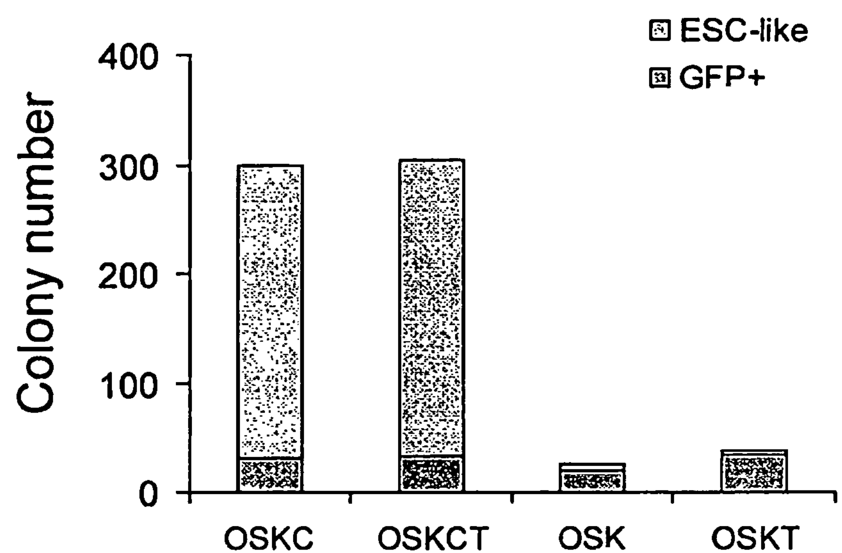
FIG. 2A to FIG. 2E are figures showing that generation of iPS cells with Oct4, Sox2, Klf4 and Tbx3 retroviral transduction.
Figure 2A:
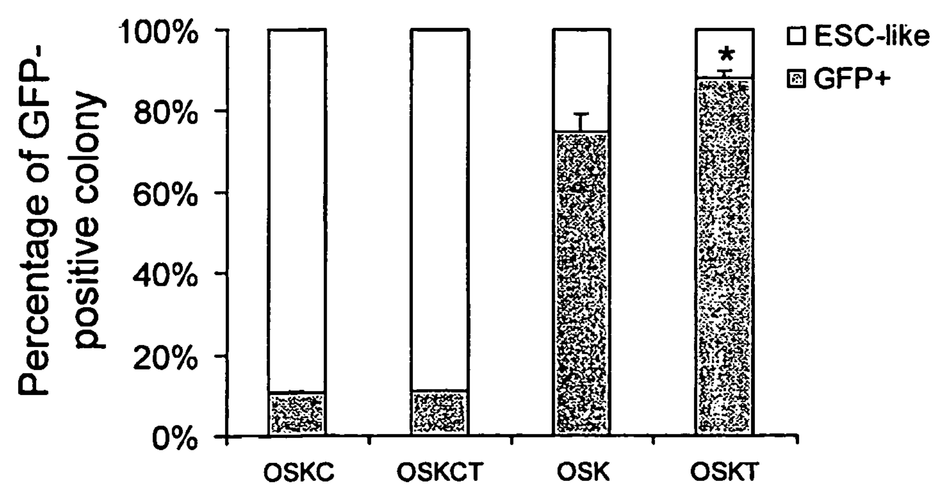

Retroviral infection of MEFs bearing the Oct4-GFP transgene with OSKC induced ~300 ESC-like colonies per $5\times10^4$ starting cells (FIG. 2A). However, only ~10% of these showed activation of the transgene.

The addition of Tbx3 (OSKCT) did not increase the frequency of $GFP^+$ colony numbers (FIG. 2A). With three factors (OSK), the total number of ESC-like colonies was dramatically reduced but false positive iPS cells were significantly eliminated as well. 74% of OSK colonies expressed GFP. (FIG. 2A).

The addition of Tbx3 (OSKT) improved the overall colony count (~38 on average) when compared with OSK (~26), and the percentage of $GFP^+$ colonies also significantly increased to 89% (FIG. 2A).

Figure 2B:
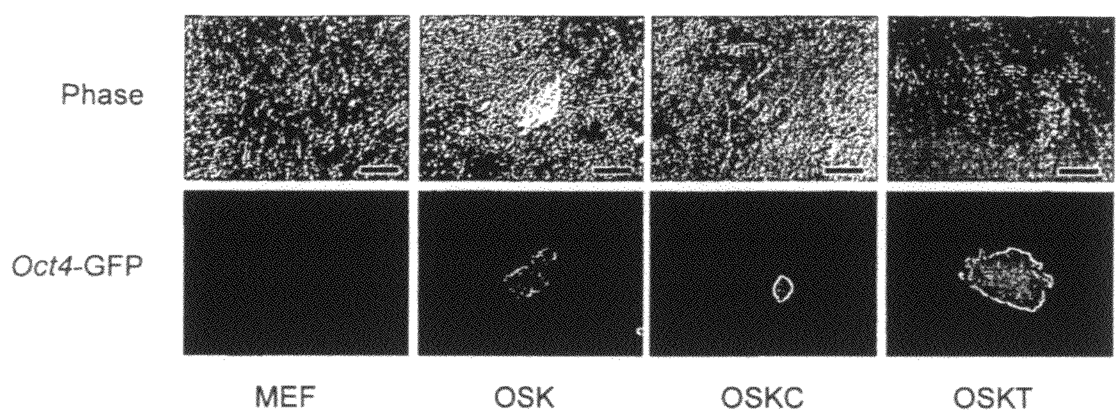

Other qualitative differences between iPS cells obtained with different factor combinations were observed. The iPS colonies derived with OSKC were interspersed and difficult to distinguish amongst transformed and partially reprogrammed cells that did not show GFP expression. OSK and OSKT iPS cell colonies were morphologically similar, with uniform GFP expression within individual colonies (FIG. 2B).

Figure 2C:
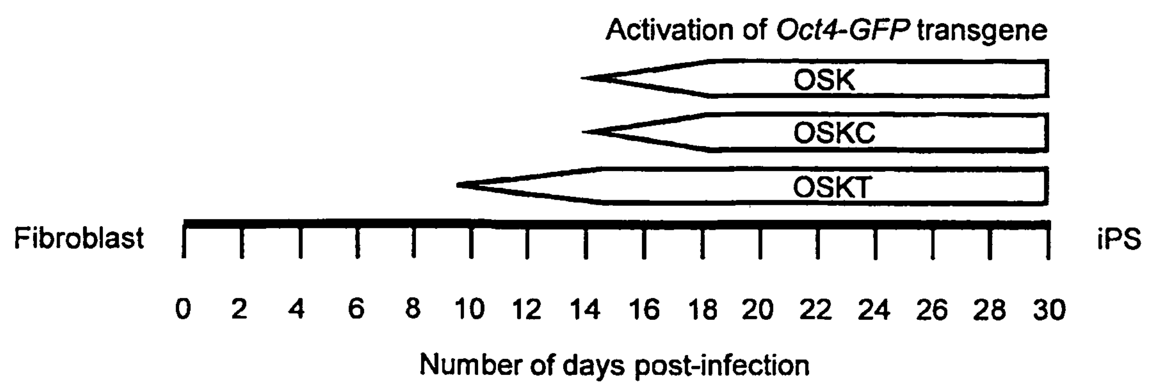
Figure 2D:
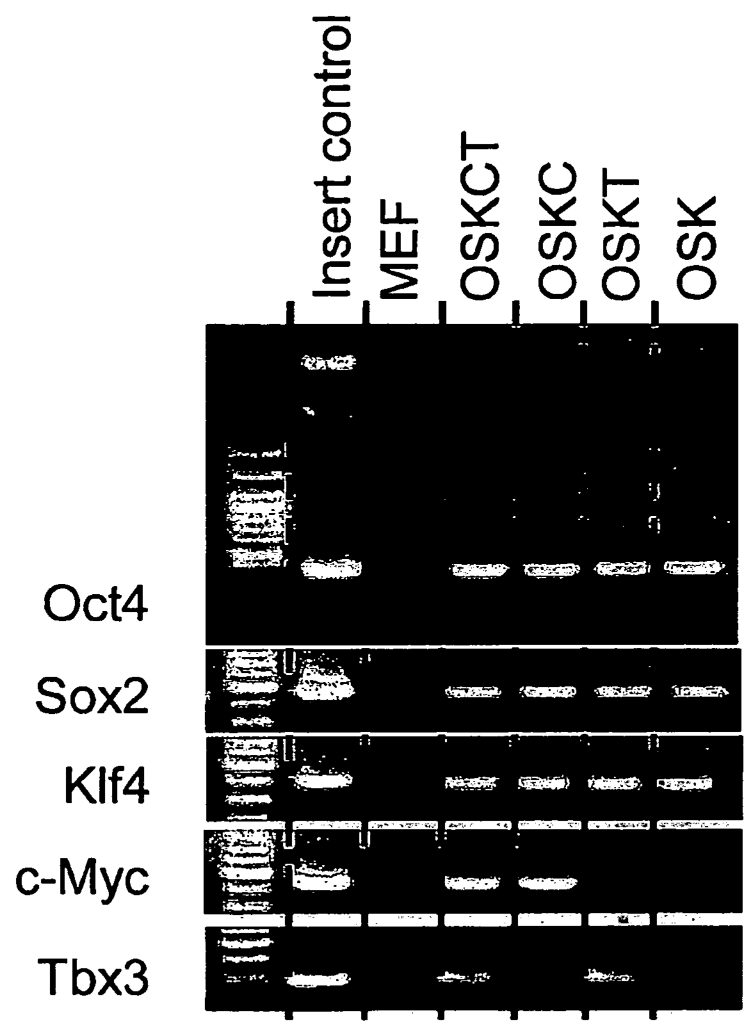

However, while the activation of Oct4 typically: required 14 days post-infection with OSK and OSKC, the use of OSKT took 9-10 days, suggesting that Tbx3 accelerated the reprogramming process (FIG. 2C). The efficiency of isolating stable iPS cell lines from $GFP^+$ colonies was similar between OSK and OSKT transduction, but almost two-fold higher than OSKC and OSKCT (FIG. 11). For all the iPS cell lines obtained, we performed PCR analysis on genomic DNA and confirmed integration of the respective transduced gene plasmids (FIG. 2D).

Figure 2E:
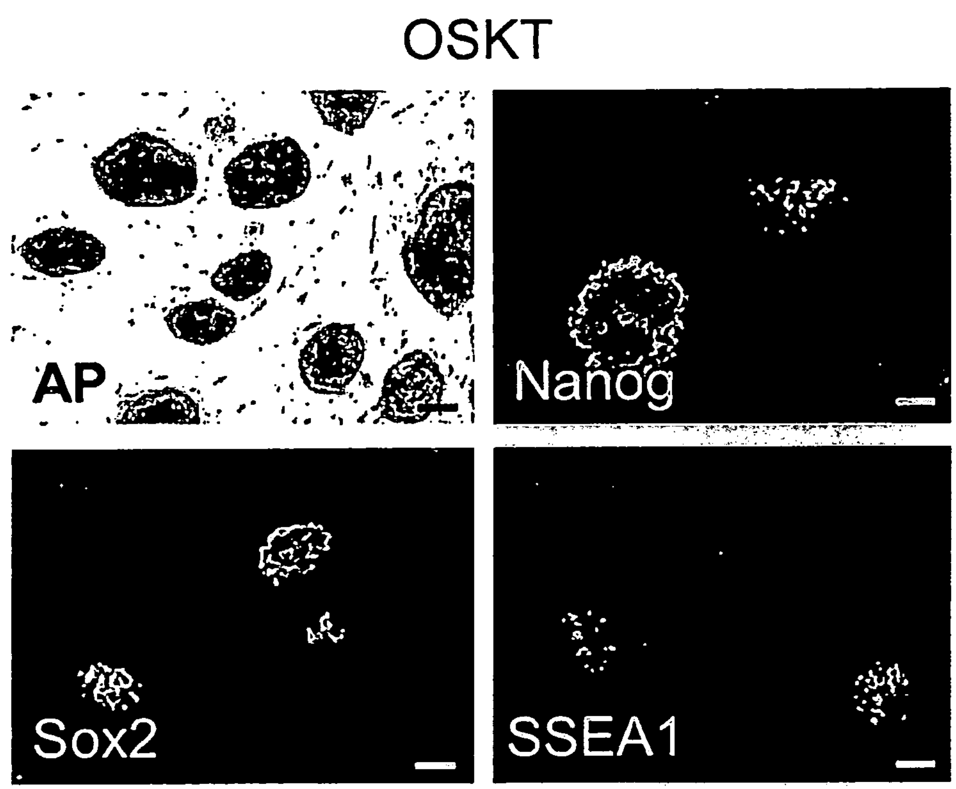
Figure 12:
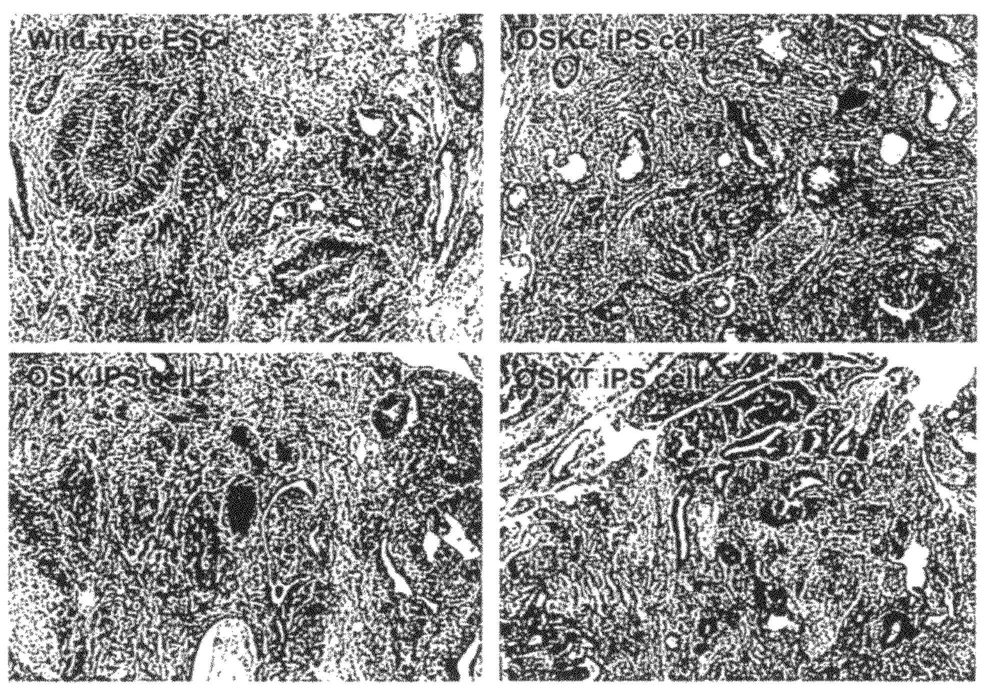
FIG. 12 is a diagram showing differentiation of iPS cells into teratomas. Induced-PS cells were injected subcutaneously into SCID mice. Tumor growths were observed in all instances, extracted, fixed, paraffin embedded, sectioned, and stained with hematoxylin and eosin (H&E). Teratomas obtained from iPS cells induced with OSKC, OSK and OSKT all showed extensive in vivo differentiation into different cell types.

Molecular characterization of iPS cells from OSKT confirmed these were alkaline phosphatase-positive and expressed Nanog, Sox2 and SSEA1 (FIG. 2E). Similar to ESCs, they also form teratomas comprised of multiple differentiated cell types when xenografted into SCID mice (FIG. 12).

Example 16

Results—Global Gene Expression Profiles

Next we sought to examine the differences in global gene expression profiles between iPS cells generated using different factor combinations.

In order to eliminate any variations that could have arisen from handling techniques, and to further ensure the reproducibility of properties inherent to iPS cell lines generated with different combinations, clones were isolated from two or more independent transduction experiments performed at separate time points for microarray profiling.

Figure 3A:
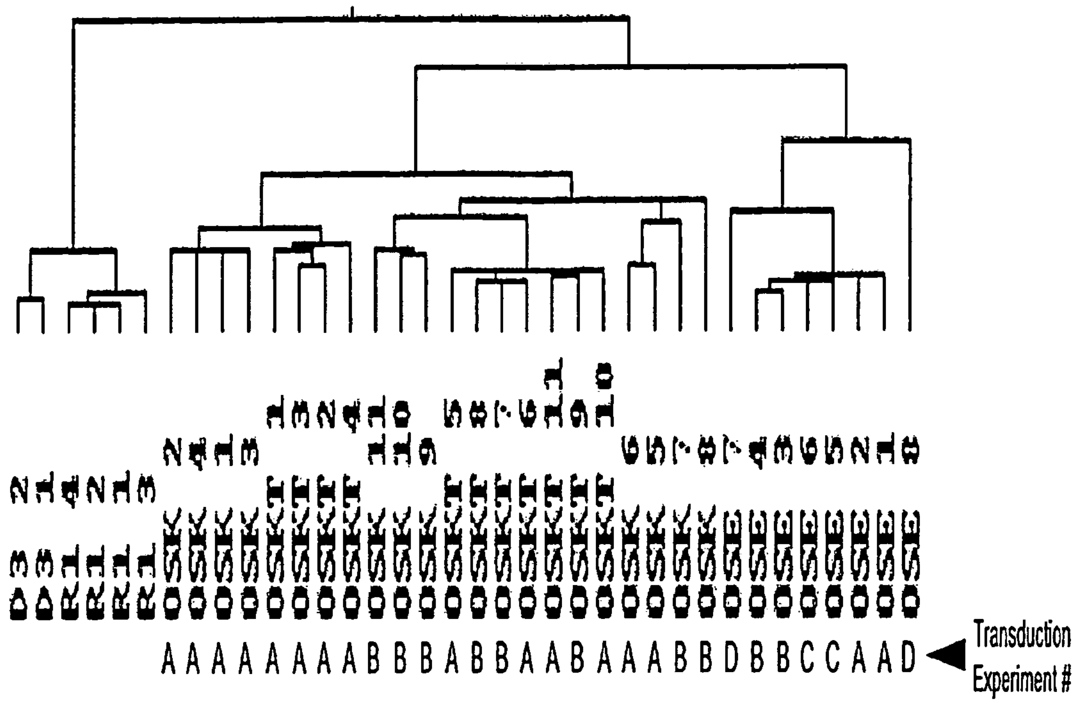
FIG. 3A and FIG. 3B are figures showing that the transcriptome of iPS cell clones generated with different combinations of reprogramming factors.
Figure 3A:
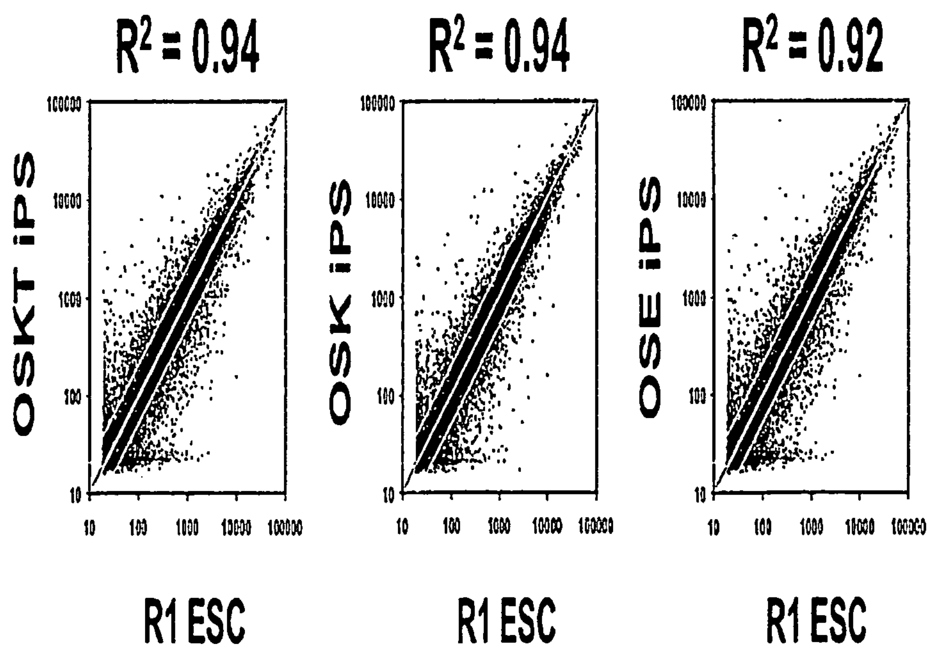

Hierarchical clustering revealed that the recently reported iPS cells generated with OS +Esrrb (OSE)[7] were most dissimilar to wild-type R1 and D3 ESCs with a correlation coefficient ($R^2$) of 0.92 (FIG. 3A).

Figure 3B:
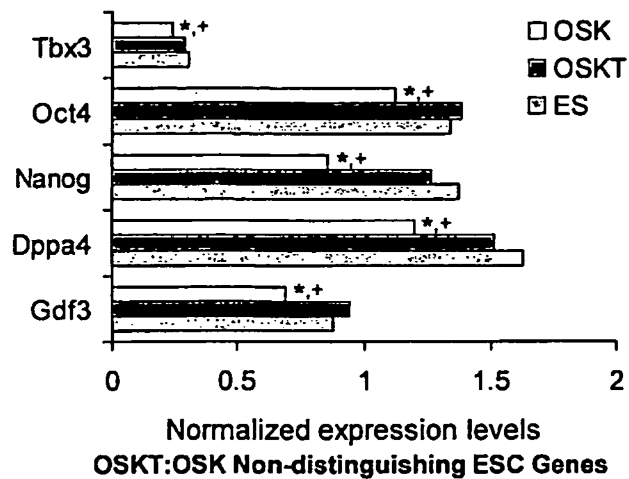
Figure 3B:
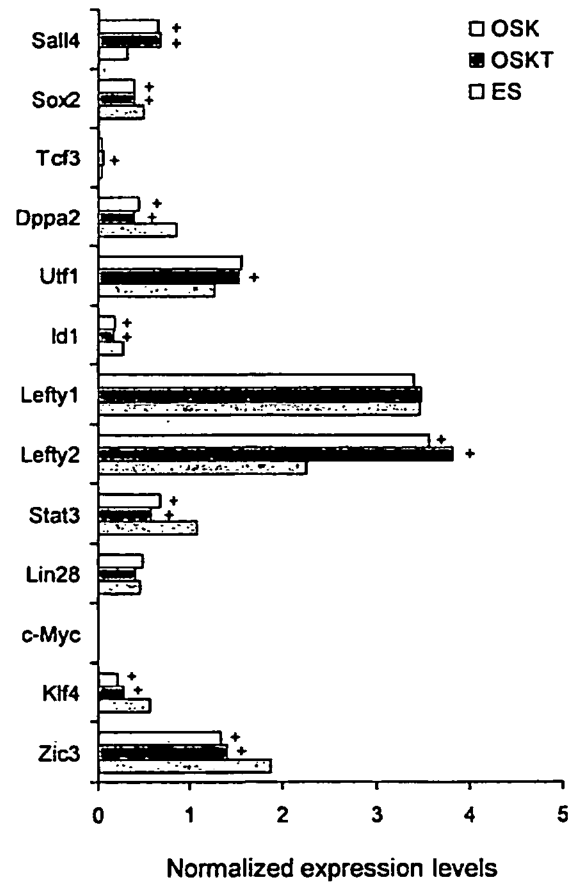
Figure 13:
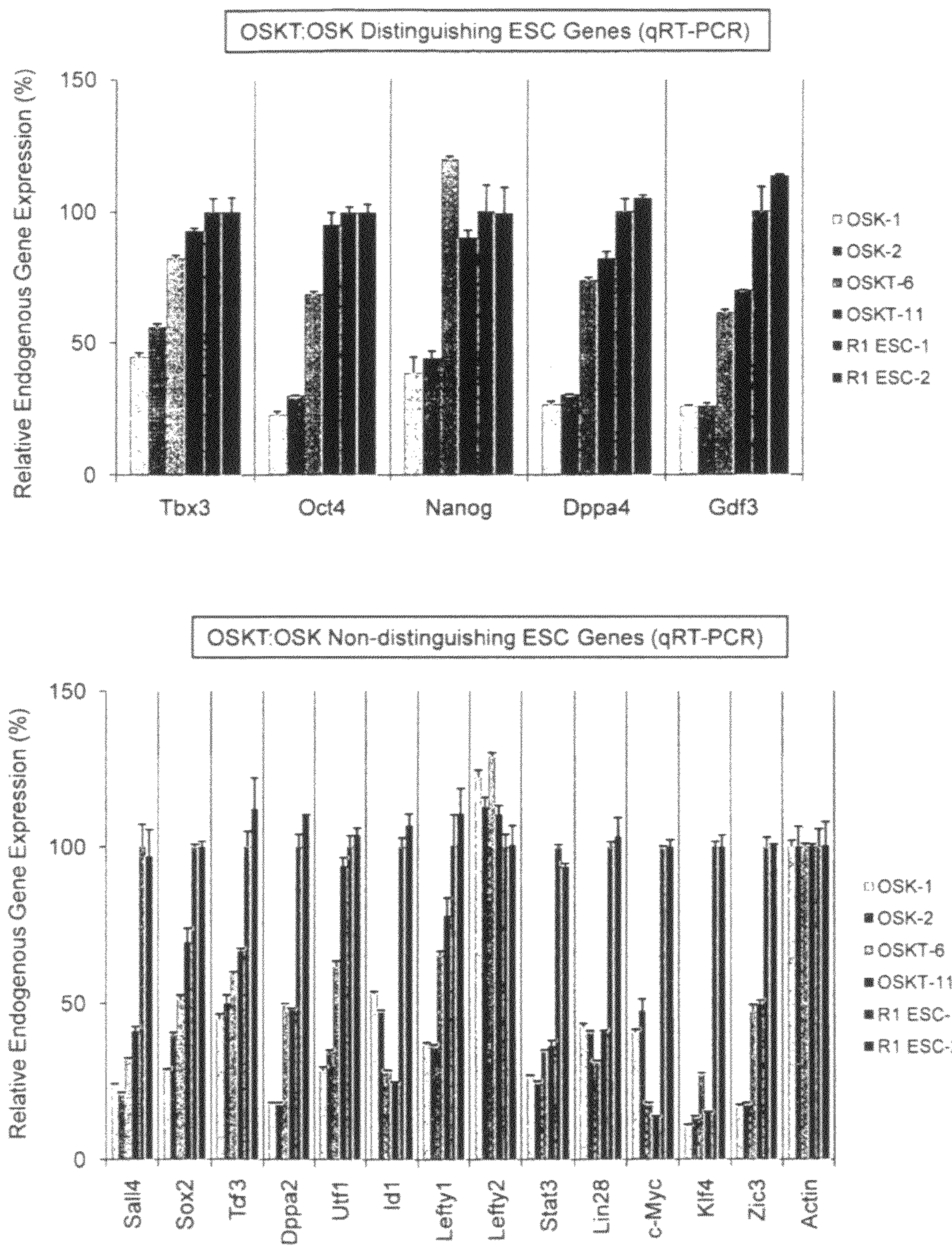
FIG. 13 is a diagram showing validation of gene expression levels obtained from microarray in FIG. 3B by qPCR. Transcript levels for the genes of interest were normalized to β-actin as an internal control, followed by normalization to R1 ESC-1. n=3 technical replicates for each iPS cell clone; error bars represent s.e.m.
Figure 14:
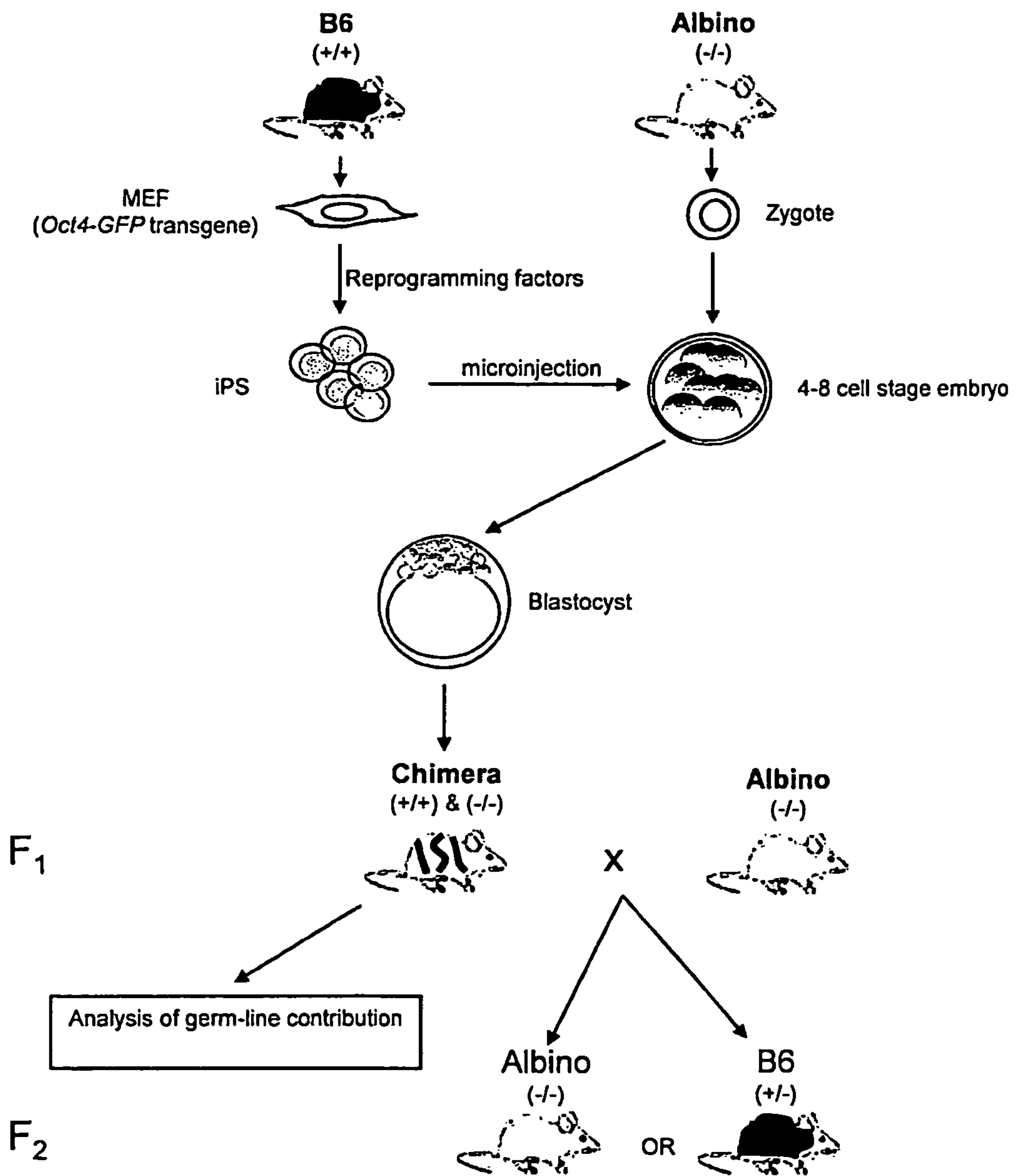
FIG. 14 is a diagram showing a scheme for the analysis of germ-line transmission competency of iPS cells. MEFs were derived from B6 mice bearing the Oct4-GFP transgene.

Both OSK and OSKT iPS cells bore closer resemblance to ESCs but were indistinguishable from each other, $R^2$=0.94. Hence, global expression profiling was not sufficiently sensitive in detecting differences between these iPS cells. In depth examination of specific gene level alterations, however, revealed key differences (FIG. 3B; FIG. 13).

We compared the pluripotency-associated gene levels among OSK, OSKT iPS and ES cells. A large portion of these genes such as Sal14, Tcf3, Sox2, Zfx, Lin28, Utf1 and Zic3 were non-distinguishing between OSKT and OSK iPS cells as their levels were similar. Surprisingly, a small subset of distinguishing features could define OSKT: from OSK: iPS cells.

The levels of Oct4, Nanog, Gdf3, Dppa4 and Tbx3 in OSKT iPS cells were equivalent to ESCs, but significantly reduced in OSK iPS cells. This suggests that exogenous Tbx3 is crucial for assisting in re-establishing proper levels of certain ESC factors critical for the induction of pluripotency that cannot be completely achieved with OSK alone.

Example 17

Results—Tbx3 Improves Quality of iPS Cells

Figure 18A:
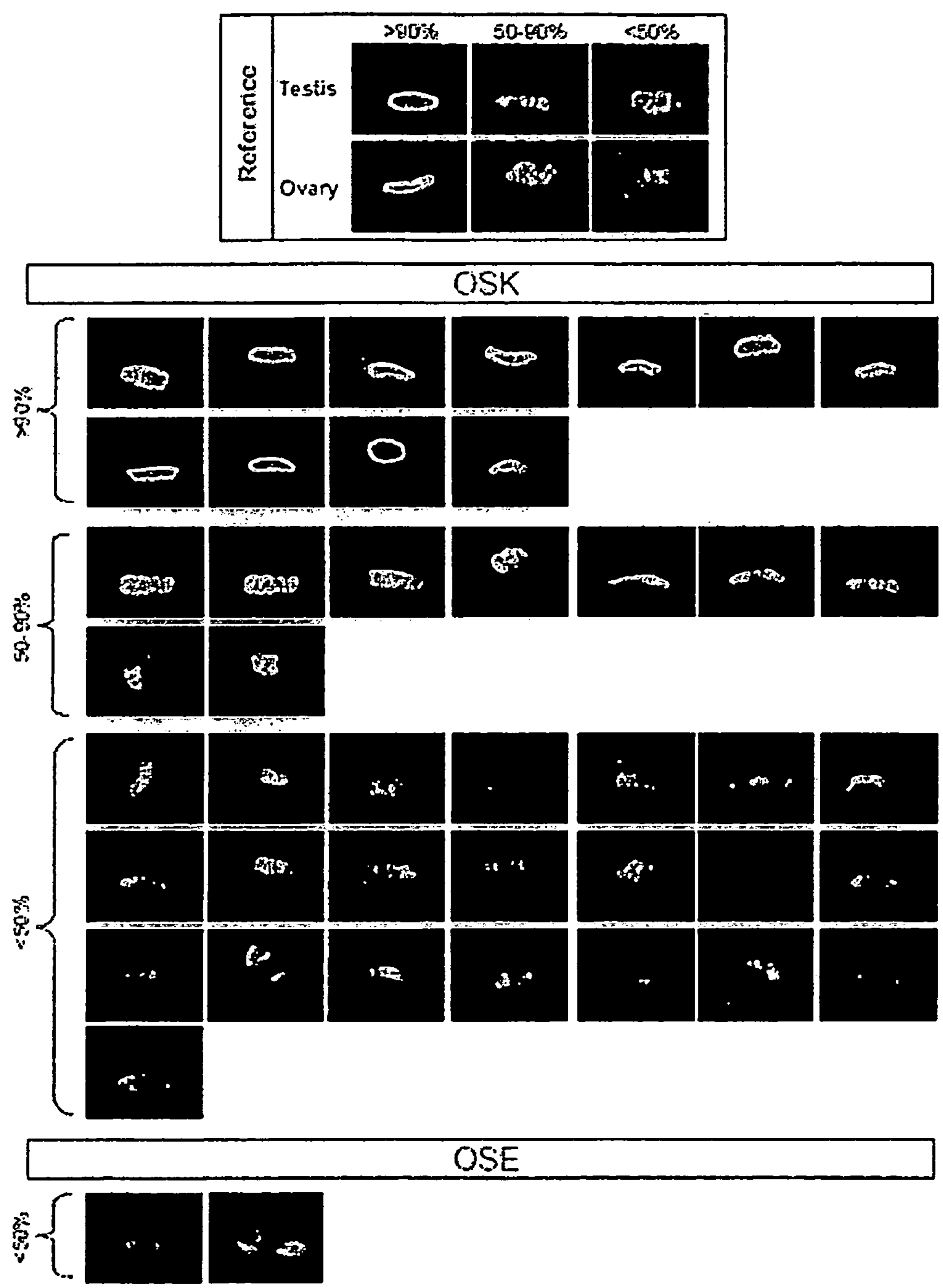
Figure 18B:
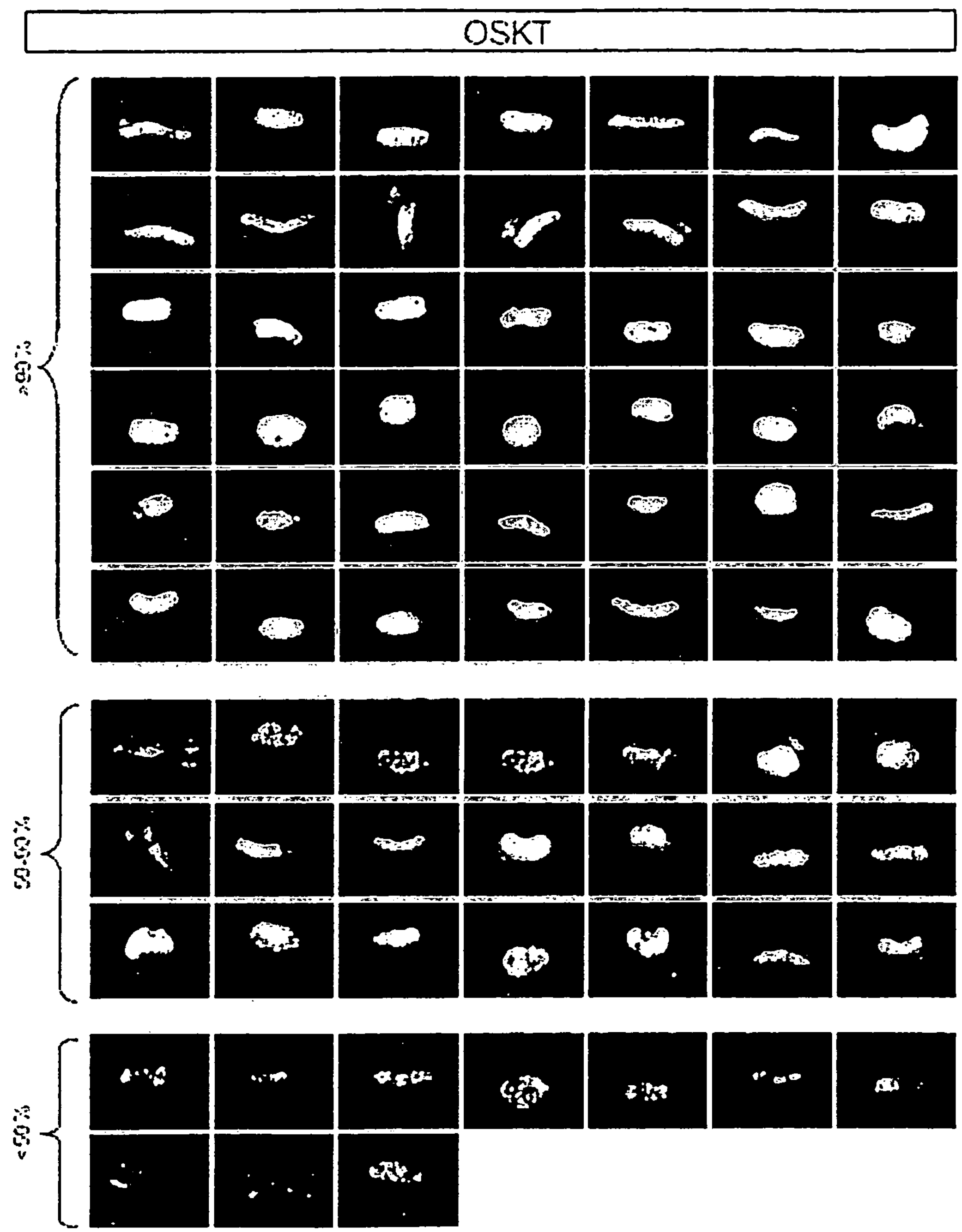

We then investigated whether OSKT iPS cells were of higher quality than OSK and OSE iPS cells (FIG. 18A and FIG. 18B).

TABLE S7

Summary of IPS clones analyses

| Original author's annotation | Clone ID used in manuscript | Transduction experiment | Microarray | Southern | Gonads | Chimera | Germline | Tetraploid |
|---|---|---|---|---|---|---|---|---|
| OSK G-1 (20/10) | OSK #1 | A | Yes | Yes | Yes | Yes | Yes | |
| OSK G-2 | OSK #2 | A | Yes | Yes | Yes | Yes | Yes | |
| OSK G-3 | OSK #3 | A | Yes | | Yes | | | |
| OSK G-4 | OSK #4 | A | Yes | | | | | |
| OSK G-8 P10 (2/11) | OSK #5 | A | Yes | Yes | | | | |
| OSK G-9 P10 (2/11) | OSK #6 | A | Yes | Yes | | | | |
| OSK G-11 P12 | OSK #7 | B | Yes | | | | | |
| OSK G-12 | OSK #8 | B | Yes | | | | | |
| OSK G-13 | OSK #9 | B | Yes | | | | | |
| OSK G-14 | OSK #10 | B | | | | | | |
| OSK G-15 | OSK #11 | B | | | | | | |
| osk 2-1 | OSK #12 | C | | Yes | Yes | Yes | Yes | Yes |
| osk 2-5 p5 | OSK #13 | C | | | Yes | Yes | Yes | |
| osk 2-6 | OSK #14 | C | | Yes | | Yes | Yes | |
| osk 3-1 | OSK #15 | D | | Yes | | | | |
| osk 3-2 | OSK #16 | D | | Yes | Yes | | | Yes |
| osk 3-5 | OSK #17 | D | | | Yes | | | Yes |
| osk 3-6 | OSK #18 | D | | | Yes | | | Yes |
| osk 3-8 | OSK #19 | D | | | Yes | | | |
| osk 3-9 | OSK #20 | D | | | Yes | | | |
| osk 3-10 | OSK #21 | D | | | Yes | | | |
| osk 4-1 | OSK #22 | E | | | | | | Yes |
| Original author's annotation | Clone ID used in manuscript | Transduction experiment | Microarray | Southern | Gonads | Chimera | Germline | Tetraploid |
| OSKT G-1 (20/11) | OSKT #1 | A | Yes | Yes | Yes | | | |
| OSKT G-2 | OSKT #2 | A | Yes | Yes | Yes | | | |
| OSKT G-3 | OSKT #3 | A | Yes | | | | | |
| OSKT G-4 | OSKT #4 | A | Yes | | Yes | | | |
| OSKT G-11 P10 | OSKT #5 | A | Yes | Yes | | | | |
| OSKT G-12 P12 | OSKT #6 | A | Yes | | Yes | Yes | Yes | |
| OSKT G-13 | OSKT #7 | B | Yes | | | | | |
| OSKT G-14 | OSKT #8 | B | Yes | | | | | |
| OSKT G-15 | OSKT #9 | B | Yes | | | | | |
| OSKT G-6 P10 | OSKT #10 | A | | | | | | |
| OSKT G-5 | OSKT #11 | A | | Yes | Yes | Yes | Yes | |
| oskt 2-1 | OSKT #12 | C | | Yes | | Yes | Yes | |
| oskt 2-4 p5 | OSKT #13 | C | | | Yes | Yes | Yes | |
| oskt 2-8 | OSKT #14 | C | | Yes | Yes | Yes | Yes | Yes |
| oskt 2-11 | OSKT #15 | C | | | | Yes | Yes | |
| oskt 3-1 | OSKT #16 | D | | Yes | Yes | | | Yes |
| oskt 3-3 | OSKT #17 | D | | | Yes | | | |
| oskt 3-4 | OSKT #18 | D | | | Yes | | | Yes |
| oskt 3-5 | OSKT #19 | D | | | Yes | | | Yes |
| oskt 3-7 | OSKT #20 | D | | | Yes | | | |
| oskt 3-8 | OSKT #21 | D | | Yes | Yes | | | |
| oskt 4-1 | OSKT #22 | E | | | | | | Yes |
| OSE 1-2 | OSE #1 | A | Yes | | Yes | Yes | Yes | Yes |
| OSE 1-3 | OSE #2 | A | Yes | | Yes | Yes | Yes | |
| OSE D45-1 | OSE #3 | B | Yes | | | | | |
| OSE D45-2 | OSE #4 | B | Yes | | | | | |
| OSE D48-1 | OSE #5 | C | Yes | | | | | |
| OSE D48-2 | OSE #6 | C | Yes | | | | | |
| OSE CD1-5 | OSE #7 | D | Yes | | | | | |
| OSE D27 | OSE #8 | D | Yes | | | | | |
| ose 2-3 p5 | OSE #9 | F | | | Yes | | | Yes |

We selected numerous iPS cell lines from each factor combination which showed homogeneous activation of Oct4-GFP within each colony: OSKT #1,2,4,6,11,13,14,16-21; OSK #1-3,12,13,16,17-21; OSE #1,2.

Figure 4A:
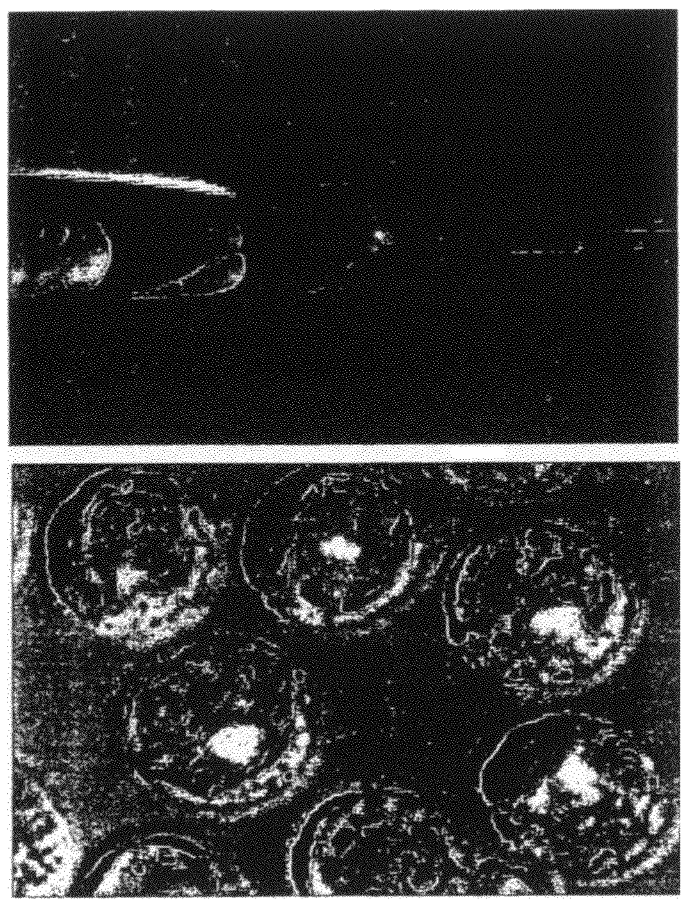

It is of note that these iPS cell lines were derived from a total of four independent transduction experiments performed at different times, thereby eliminating any biasness in clonal selection that may arise from the stochastic behavior of individual clones. Induced-PS cells were then injected into 4-8 cell embryos and cultured in vitro to blastocysts (FIG. 4A). There was no difference in the maturation efficiency (~95%) between the three iPS cell lines (data not shown).

All blastocysts transplanted into the surrogate female mice initially had shown contribution of $GFP^+$ cells to the inner cell mass (ICM) (FIG. 4A) and live chimeras were obtained from the three combinations. As evaluated by coat color, all OSKT and OSK iPS chimeras showed coats with varying density of black fur, signifying iPS cell contribution; whereas OSE iPS chimeras clearly had less black coat (FIG. 4D, top panels), indicating that OSE iPS cells tend to contribute poorly to chimerism.

Figure 4B:
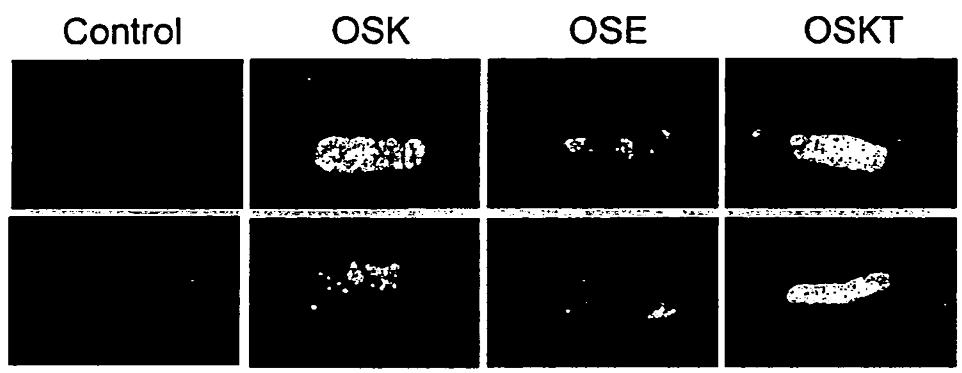
Figure 15A:
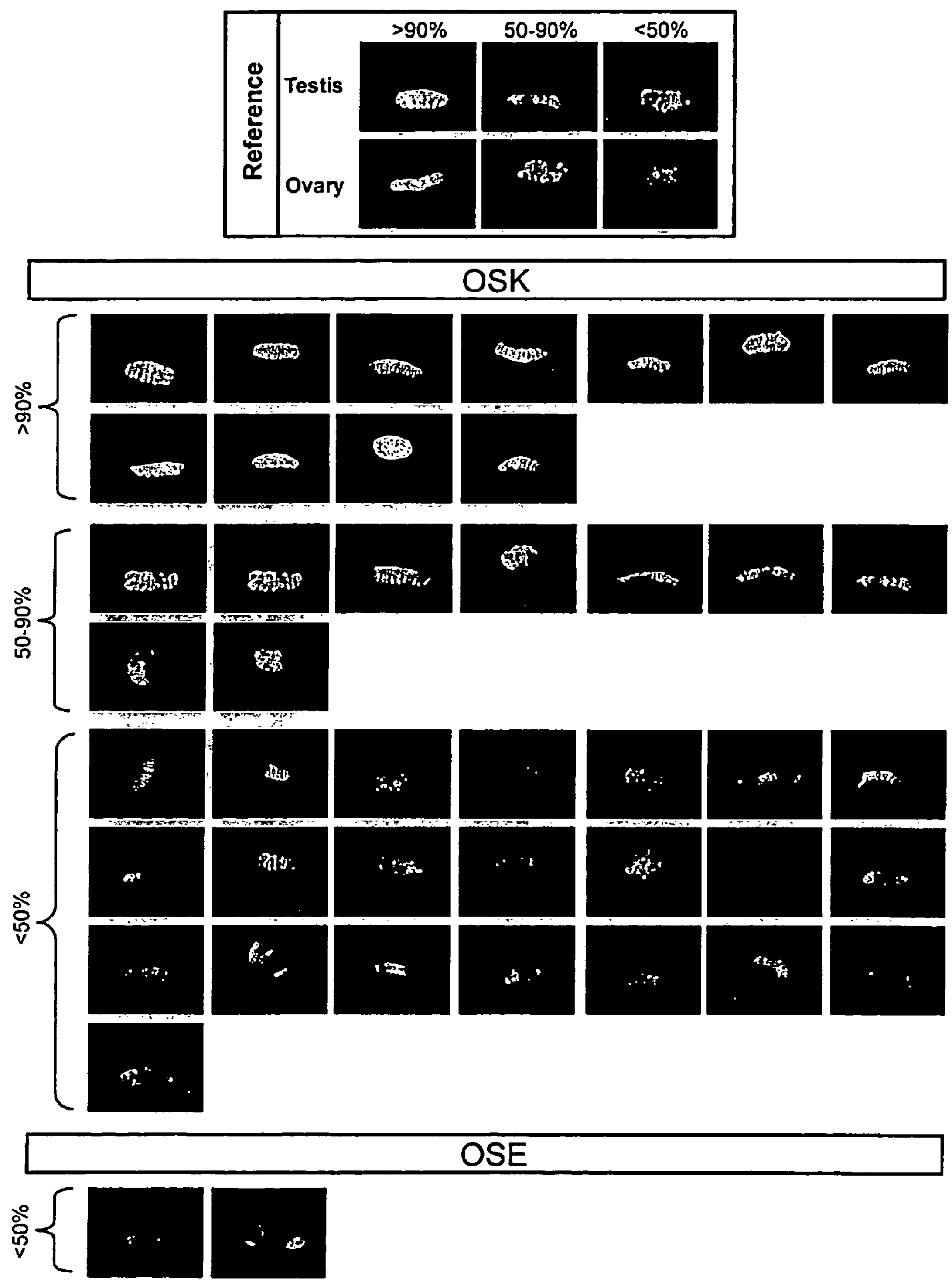
Figure 15B:
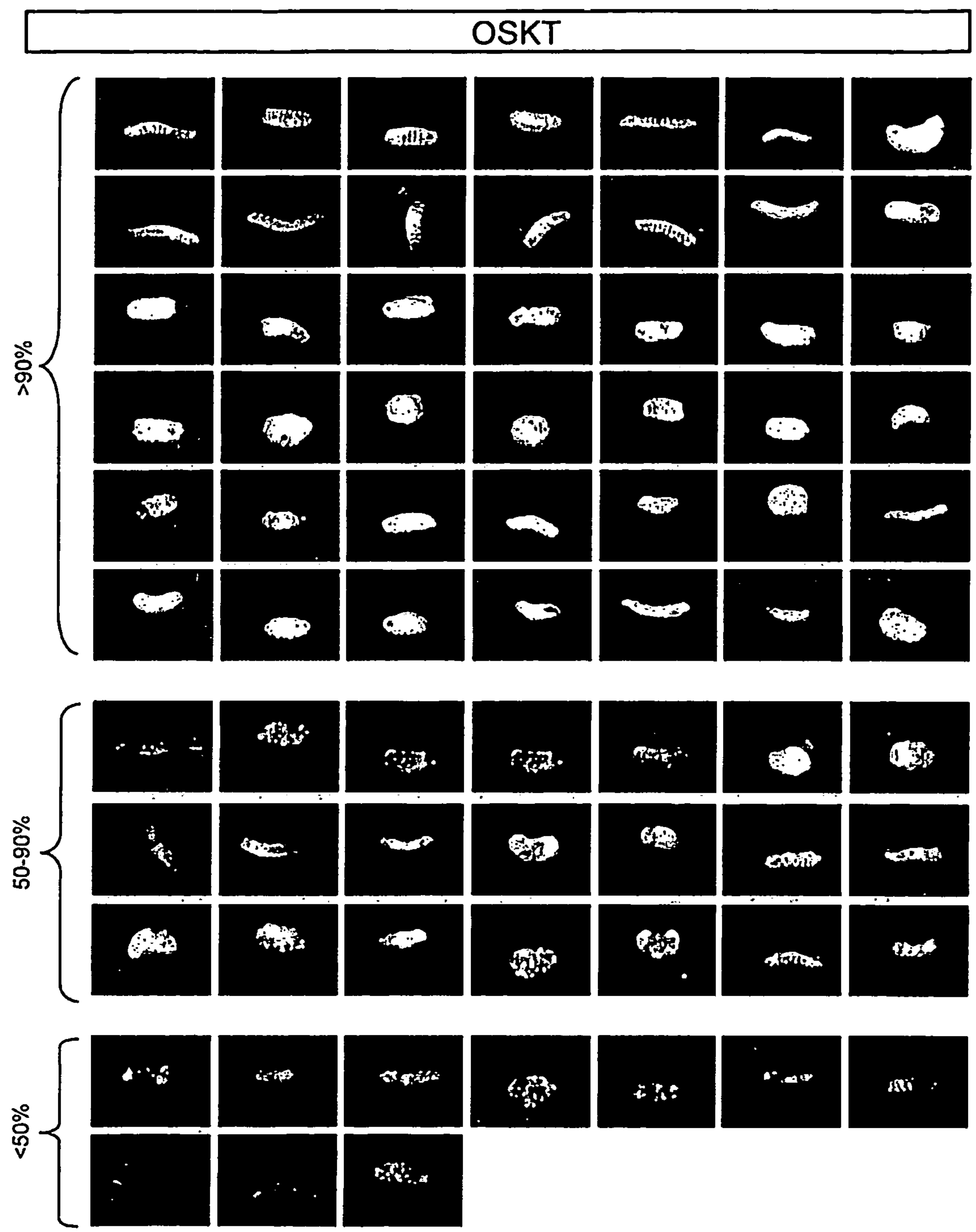

More interestingly, obvious differences can be discerned between OSKT and OSK iPS cells in their ability to colonize the germ tissues. At E13.5, the gonads (testis or ovaries) were obtained from the $F_1$ chimeric embryos. 34.9% of the gonads from OSKT iPS embryos showed contribution of iPS cells with GFP expression contrasting significantly with 23.6% from OSK iPS and 12.5% from OSE iPS embryos (FIG. 4B; FIG. 15A and FIG. 15B; p<0.01).

Further assessment based on GFP distribution within these gonads revealed extensive contribution by OSKT iPS cells as 57.5% of the chimeric gonads contained >90% $GFP^{+}$ compared to 26.2% of those from OSK iPS embryos (FIG. 4C; p<0.01). This indicates OSKT iPS cells were more effective in colonizing the germ tissues while OSK and OSE iPS cells were much less efficient.

Figure 4D:
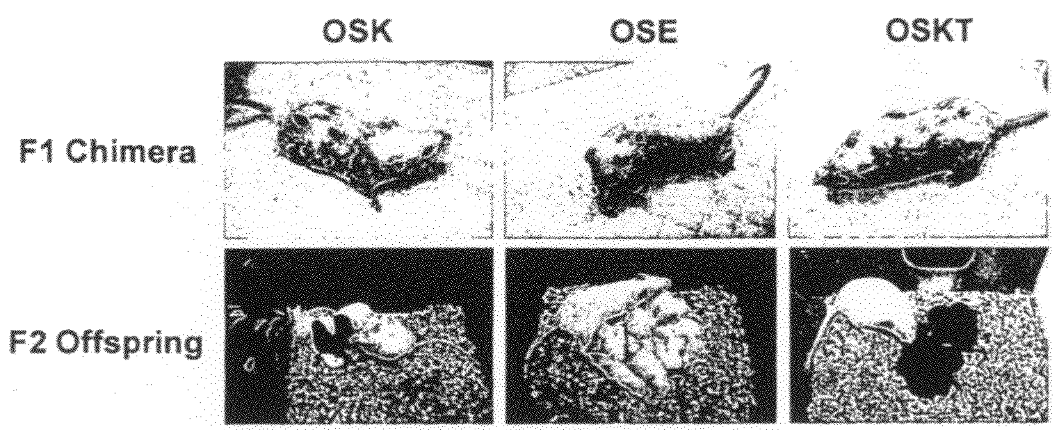

Using one of the most stringent criteria for demonstrating the quality of iPS cell clones and their resemblance to wild-type ESCs, we tested their frequency of germ-line transmission and production of viable $F_2$ offspring. Once again, we used several iPS lines from each combination to eliminate any stochastic clonal variation and biasness in clone selection. Induced-PS cells generated with OSE had very poor capacity for germ-line transmission (FIG. 4D, bottom panels; and FIG. 4E).

Using five chimeras from two iPS cell lines which were bred with albino mice, a total of seven litters were obtained. Only one litter contained two of 10 offspring that had iPS cell-derived black coat. With OSK, nine chimeras from five iPS cell lines were used for breeding 13 litters were produced, of which only two had 100% black offspring, and another four had an average of ~33%. Strikingly, with the nine OSKT chimeras obtained from six iPS cell lines, nine of 14 litters had 100% black offspring, three had 41%, 50% and 28% each, and only two with none (FIG. 4E; p<0.005).

It has been previously reported that improper retroviral silencing can alter the efficiency of generating iPS cells and their resultant properties. It has also been suggested that the frequency of retroviral integration into the somatic cell genome can affect the behavior of iPS cells as a result of DNA damage.

To exclude these possibilities, we confirmed that exogenous expression from the retroviral plasmids has been silenced in the iPS cell clones for all combinations of factors tested (FIG. 16). Southern blot analyses showed that retroviral integration the different OSK factors into either OSK or OSKT iPS cells was comparable (FIG. 17).

Importantly, even with the additional integration of exogenous Tbx3, iPS cells were consistently of higher quality, thus ruling out the effects of DNA damage on their properties.

Example 18

Results—OSKT-Derived iPS Cells can Generate Viable Mice

We then speculated that the higher quality OSKT-derived iPS cells could be used to generate viable mice composed entirely of the engineered cells through tetraploid complementation[16,17].

This has not been previously shown, perhaps owing to the difficulty of generating high quality iPS cells with the standard factor combinations. In the two cell lines tested, OSKT #14 iPS cells supported embryonic development of two fetuses until E19 when C-section was performed because of suspected uterine regression.

Figure 4F:
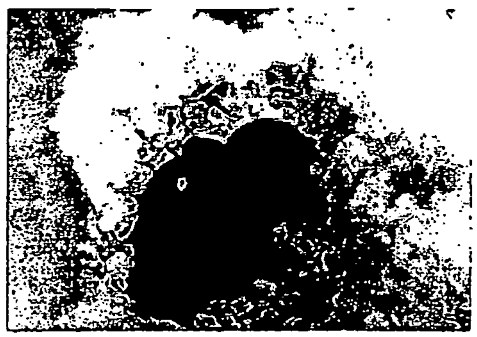
Figure 4F:
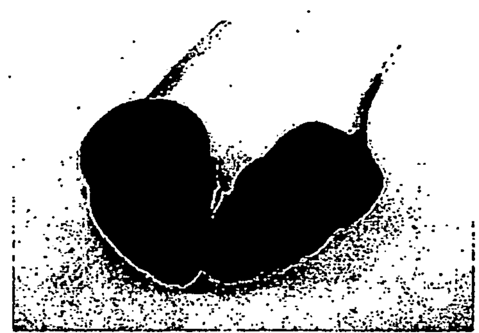
Figure 4F:
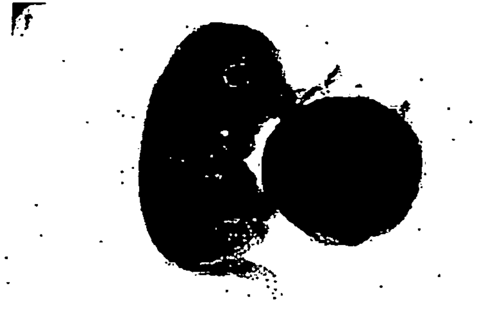

It would seem likely that live births may be expected in this case (FIG. 4F). With OSKT #16, we were successful in obtaining 10 live births (20%) from 50 aggregated embryos transferred into four surrogate recipients. Of these, eight survived to day 1; five to day 2, three to week I, and two survived past two months and continued to thrive.

Example 19

Results—Regulatory Targets of Tbx3

To better understand how Tbx3 may contribute to improving the quality of iPS cells, we performed Solexa ChIP-sequencing to uncover the direct regulatory targets of Tbx3 in ESCs.

Figure 4G:
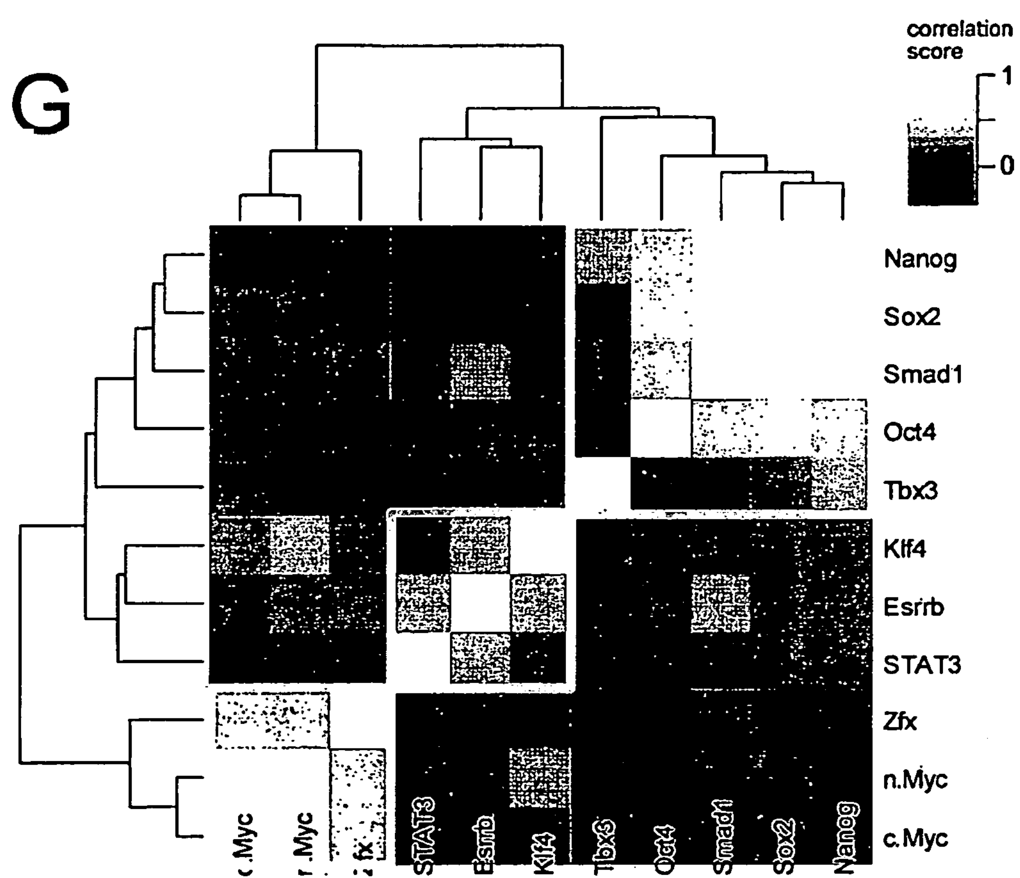

Strikingly, hierarchical clustering of Tbx3 with the previously mapped ESC factors[18] revealed that it shares a large number of common binding sites with the classic pluripotency-associated transcription factors Oct4, Sox2, Nanog and Smad1 (FIG. 4G).

Tbx3 is also found to target the ESC factors Oct4, Sox2, Sal14, Lefty1/2, Zfp42, as well as reprogramming factors Klf2/4/5 and n/c-Myc (FIG. 18A and FIG. 18B). This finding is consistent with our initial reason for focusing on Tbx3 regulated by Nanog and Tcf3 and supporting LIF-independent ESC growth, and is further supported by recent evidence that Tbx3 or Klf4 over-expression confers LIF-independence[19].

Example 20

Results—Induction of Human iPS by Tbx3

The experiments on mouse cells described in the Examples above were repeated with human cells.

In the human system, the data obtained shows that a combination of OSKC and Tbx3 (OSKCT), when compared to OSKC, resulted in a higher efficiency of generating iPS cells.

Furthermore, some of the human iPS cells look more like murine ES cells with the typical tight and dome shaped colonies.

Finally, a number of the human iPS clones grow and proliferate in response to ES medium with FCS, and LIF, even with no FGF. The growth factor usually used for human ES cell expansion is FGF. Conventional human ES cells cannot respond to LIF.

Tbx3 thus appears to be a key factor to generate a new type of human pluripotent cell with pluripotency potential similar to murine ES cells. This will offer a tremendous advantage over the conventional human ES or human iPS cells since mouse ES cells are much easier to expand, culture and maintain. Mouse ES cells are thought to be derived from more primitive embryo stage compared to human ES cells that are thought to be derived from epiblast stage.

Thus Tbx3 may be useful to generate human iPS cells that are more embryonic, better and more versatile for generating different lineages including germ cells.

Example 21

Discussion

Taken altogether, our study highlights the remarkable success of OSKT combination in generating high quality iPS cells capable of germ-line transmission at high efficiency.

Previous studies have primarily employed morphological assessment and global gene expression analyses as indicators of iPS cell pluripotency. However, we have demonstrated here that in vitro analyses is not sufficient to distinguish bona fide iPS cells with truly ESC-like properties from poor quality iPS cells which do not possess germ-line competence. Our demonstration that OSKT iPS cells can also generate high frequency live birth mice by tetraploid complementation further strengthens our data implicating the qualitative impact of Tbx3.

With the emergence of modified genetic and chemical methods, and the emphasis on the use of minimal reprogramming factors to derive iPS cells, we would like to suggest that some benchmark, as exemplified here by OSKT-derived iPS cells, should be employed to evaluate the quality and biological properties of iPS cells (FIG. 19).

The mechanistic explanation for the specific role of Tbx3 in vastly improving iPS cell quality needs more detailed clarification. Tbx3 belongs to a family of highly conserved T-box genes which have broad developmental roles and implications for human diseases[20-22]. Tbx3 has also been implicated in maintaining the pluripotency of ESCs where its loss leads to differentiation[15,23]. It is the earliest T-box member to be expressed during pre-implantation embryonic development where it localized to the ICM of the blastocyst[24]. These, together with our ChIP-seq data, suggest that Tbx3 is important for the effective re-establishment of the ESC circuitry during the onset of reprogramming, and its subsequent maintenance.

The presence of exogenous Tbx3 during the initiation of reprogramming may ensure proper titration of pluripotency and other yet unidentified reprogramming factors which are reactivated by OSK to the optimal level, resulting in the emergence of a higher frequency of truly ESC-like iPS cells. We therefore propose a model whereby the re-establishment of pluripotency from a somatic state is achieved in an increasing probabilistic step-wise manner (FIG. 19).

The use of different factor combinations result in the generation of iPS populations and clones with markedly different developmental potentials centered upon progressive "landmarks" of pluripotency. The addition of Tbx3 to a particular combination of reprogramming factors increases the probabilistic frequency of iPS cells that can attain a pluripotent state equivalent or closest to ESCs within the entire population of reprogrammed cells.

REFERENCES

1. Takahashi, K.& Yamanaka, S. Induction of pluripotent stem cells from mouse embryonic and adult fibroblast cultures by defined factors. *Cell* 126, 663-76 (2006).

2. Huangfu, D. et al. Induction of pluripotent stem cells by defined factors is greatly improved by small-molecule compounds. *Nat Biotechnol* 26, 795-7 (2008).

3. Huangfu, D. et al. Induction of pluripotent stem cells from primary human fibroblasts with only Oct4 and Sox2. *Nat Biotechnol* 26, 1269-75 (2008).

4. Shi, Y. et al. Induction of pluripotent stem cells from mouse embryonic fibroblasts by Oct4 and Klf4 with small-molecule compounds. *Cell Stem Cell* 3, 568-74 (2008).

5. Silva, J. et al. Promotion of reprogramming to ground state pluripotency by signal inhibition. *PLoS Biol* 6, e253 (2008).

6. Okita, K., Nakagawa, M., Hyenjong, H., Ichisaka, T. & Yamanaka, S. Generation of mouse induced pluripotent stem cells without viral vectors. *Science* 322; 949-53 (2008).

7. Feng, B. et al. Reprogramming of fibroblasts into induced pluripotent stem cells with orphan nuclear receptor Esrrb. *Nat Cell Biol* (2009).

8. Marson, A. et al. Wnt signaling promotes reprogramming of somatic cells to pluripotency. *Cell Stem Cell* 3, 132-5 (2008).

9. Kim, J. B. et al. Oct4-induced pluripotency in adult neural stem cells. *Cell* 136, 411-9 (2009).

10. Chin, M. H. et al. Induced pluripotent stem cells and embryonic stem cells are distinguished by gene expression signatures. *Cell Stem Cell* 5, 111-23 (2009).

11. Mitsui, K. et al. The homeoprotein Nanog is required for maintenance of pluripotency in mouse epiblast and ES cells. *Cell* 113, 631-42 (2003).

12. Chambers, I. et al. Functional expression cloning of Nanog, a pluripotency sustaining factor in embryonic stem cells. *Cell* 113, 643-55 (2003).

13. Silva, J., Chambers, I., Pollard, S. & Smith, A. Nanog promotes transfer of pluripotency after cell fusion. *Nature* 441, 997-1001 (2006).

14. Tam, W. L. et al. T-cell factor 3 regulates embryonic stem cell pluripotency and self-renewal by the transcriptional control of multiple lineage pathways. *Stem Cells* 26, 2019-31 (2008).

15. Ivanova, N. et al. Dissecting self-renewal in stem cells with RNA interference. *Nature* 442, 533-8 (2006).

16. Eakin, G. S. & Hadjantonakis, A. K. Production of chimeras by aggregation of embryonic stem cells with diploid or tetraploid mouse embryos. *Nat Protoc* 1, 1145-53 (2006).

17. Ohta, H., Sakaide, Y., Yamagata, K. & Wakayama, T. Increasing the cell number of host tetraploid embryos can improve the production of mice derived from embryonic stem cells. *Biol Reprod* 79, 486-92 (2008).

18. Chen, X. et al. Integration of external signaling pathways with the core transcriptional network in embryonic stem cells. *Cell* 133; 1106-17 (2008).

19. Niwa, H., Ogawa, K., Shimosato, D. & Adachi, K. A parallel circuit of LIF signalling pathways maintains pluripotency of mouse ES cells. *Nature* 460, 118-22 (2009).

20. Bamshad, M. et al. Mutations in human TBX3 alter limb, apocrine and genital development in ulnar-mammary syndrome. *Nat Genet* 16, 311-5 (1997).

21. Packham, E. A. & Brook, J. D. T-box genes in human disorders. *Hum Mol Genet* 12 Spec No 1, R37-44 (2003).

22. Simon, H. T-box genes and the formation of vertebrate forelimb- and hindlimb specific pattern. *Cell Tissue Res* 296, 57-66 (1999).

23. Galan-Caridad, J. M. et al. Zfx controls the self-renewal of embryonic and hematopoietic stem cells. *Cell* 129, 345-57 (2007).

24. Chapman, D. L. et al. Expression of the T-box family genes, Tbx1-Tbx5, during early mouse development. *Dev Dyn* 206, 379-90 (1996).

25. Zhang, J. et al. Sal14 modulates embryonic stem cell pluripotency and early embryonic development by the transcriptional regulation of Pou5f1. *Nat Cell Biol* 8, 1114-23 (2006).

26. Yu, J. et al. Induced pluripotent stem cell lines derived from human somatic cells. *Science* 318, 1917-20 (2007).

27. Reynolds, A. et al. Rational siRNA design for RNA interference. *Nat Biotechnol* 22, 326-30 (2004).

28. Chua, S. W. et al. A novel normalization method for effective removal of systematic variation in microarray data. *Nucleic Acids Res* 34, e38 (2006).

29. Loh, Y. H. et al. The Oct4 and Nanog transcription network regulates pluripotency in mouse embryonic stem cells. *Nat Genet* 38, 431-40 (2006).

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

The invention claimed is:

1. A method of producing induced pluripotent stem cells, the method comprising introducing into a somatic cell one or more retroviral vectors encoding Oct-4, Sox-2, Klf-4, and Tbx3, wherein said cells are cultured to produce induced pluripotent stem cells.

2. A method of identifying a candidate molecule capable of modulating the production of induced pluripotent stem cells from a somatic cell, comprising performing the method of claim 1 in the presence of one or more candidate molecules;

performing the method of claim 1 in the absence of the one or more candidate molecules;

determining whether one or more activities of the somatic cell selected from the group consisting of: induction of pluripotency, reprogramming, and expression of one or more characteristics of a pluripotent cell, are modulated by the presence of the one or more candidate molecules; and selecting a candidate molecule that modulates one or more of said activities of the somatic cell.

3. The method of claim 2, wherein the selected candidate molecule increases one or more of said activities of the somatic cell.

* * * * *

SEQUENCE LISTING

<160> NUMBER OF SEQ ID NOS: 25

<210> SEQ ID NO 1
<211> LENGTH: 4754
<212> TYPE: DNA
<213> ORGANISM: Homo sapiens

<400> SEQUENCE: 1
gaattctaga ggcggcggag ggtggcgagg agctctcgct ttctctcgct ccctccctct 60
ccgactccgt ctctctctct ctctctctct ctcccctccc tctctttccc tctgttccat 120
tttttccccc tctaaatcct ccctgccctg cgcgcctgga cacagattta ggaagcgaat 180
tcgctcacgt tttaggacaa ggaagagaga gaggcacggg agaagagccc agcaagattt 240
ggattgaaac cgagacaccc tccggaggct cggagcagag gaaggaggag gagggcggcg 300
aacggaagcc agtttgcaat tcaagttttg atagcgctgg tagaaggggg tttaaatcag 360 atttttttttt ttttaaagga gagagacttt ttccgctctc tcgctccctg ttaaagccgg 420
gtctagcaca gctgcagacg ccaccagcga gaaagaggga gaggaagaca gatagggggc 480
gggggaagaa gaaaaagaaa ggtaaaaagt cttctaggag aacctttcac atttgcaaca 540
aaagacctag gggctggaga gagattcctg ggacgcaggg ctggagtgtc tatttcgagc 600
tcagcggcag ggctcgggcg cgagtcgaga ccctgctcgc tcctctcgct tctgaaaccg 660
acgttcagga gcggcttttt aaaaacgcaa ggcacaagga cggtcacccg cgcgactatg 720
tttgctgatt tttcgccttg ccctctttaa aagcggcctc ccattctcca aaagacactt 780
cccctcctcc ctttgaagtg cattagttgt gatttctgcc tccttttctt ttttctttct 840
tttttgtttt gctttttccc cccttttgaa ttatgtgctg ctgttaaaca acaacaaaaa 900
aacaacaaaa cacagcagct gcggacttgt ccccggctgg agcccagcgc ccgcctgga 960 gtggatgagc ctctccatga gagatccggt cattcctggg acaagcatgg cctaccatcc 1020
gttcctacct caccgggcgc cggacttcgc catgagcgcg gtgctgggtc accagccgcc 1080
gttcttcccc gcgctgacgc tgcctcccaa cggcgcggcg gcgctctcgc tgccgggcgc 1140
cctggccaag ccgatcatgg atcaattggt gggggcggcc gagaccggca tcccgttctc 1200
ctccctgggg ccccaggcgc atctgaggcc tttgaagacc atggagcccg aagaagaggt 1260
ggaggacgac cccaaggtgc acctggaggc taaagaactt tgggatcagt ttcacaagcg 1320
gggcaccgag atggtcatta ccaagtcggg aaggcgaatg tttcctccat ttaaagtgag 1380
atgttctggg ctggataaaa aagccaaata cattttattg atggacatta tagctgctga 1440
tgactgtcgt tataaatttc acaattctcg gtggatggtg gctggtaagg ccgaccccga 1500
aatgccaaag aggatgtaca ttcacccgga cagccccgct actggggaac agtggatgtc 1560
caaagtcgtc actttccaca aactgaaact caccaacaac atttcagaca aacatggatt 1620
tactatattg aactccatgc acaaatacca gccccggttc cacattgtaa gagccaatga 1680
catcttgaaa ctcccttata gtacatttcg gacatacttg ttccccgaaa ctgaattcat 1740

```
cgctgtgact gcataccaga atgataagat aacccagtta aaaatagaca acaacccttt   1800
tgcaaaaggt ttccgggaca ctggaaatgg ccgaagagaa aaaagaaaac agctcaccct   1860
gcagtccatg agggtgtttg atgaaagaca caaaaaggag aatgggacct ctgatgagtc   1920
ctccagtgaa caagcagctt tcaactgctt cgcccaggct tcttctccag ccgcctccac   1980
tgtagggaca tcgaacctca aagatttatg tcccagcgag ggtgagagcg acgccgaggc   2040
cgagagcaaa gaggagcatg gccccgaggc ctgcgacgcg gccaagatct ccaccaccac   2100
gtcggaggag ccctgccgtg acaagggcag ccccgcggtc aaggctcacc ttttcgctgc   2160
tgagcggccc cgggacagcg ggcggctgga caaagcgtcg cccgactcac gccatagccc   2220
cgccaccatc tcgtccagca ctcgcggcct gggcgcggag gagcgcagga gcccggttcg   2280
cgagggcaca gcgccggcca aggtggaaga ggcgcgcgcg ctcccgggca aggaggcctt   2340
cgcgccgctc acggtgcaga cggacgcggc cgccgcgcac ctggcccagg gccccctgcc   2400
tggcctcggc ttcgccccgg gcctggcggg ccaacagttc ttcaacgggc acccgctctt   2460
cctgcacccc agccagtttg ccatgggggg cgccttctcc agcatggcgg ccgctggcat   2520
gggtcccctc ctggccacgg tttctggggc ctccaccggt gtctcgggcc tggattccac   2580
ggccatggcc tctgccgctg cggcgcaggg actgtccggg gcgtccgcgg ccaccctgcc   2640
cttccacctc cagcagcacg tcctggcctc tcagggcctg gccatgtccc ctttcggaag   2700
cctgttccct tacccctaca cgtacatggc cgcagcggcg gccgcctcct ctgcggcagc   2760
ctccagctcg gtgcaccgcc acccctacct caatctgaac accatgcgcc cgcggctgcg   2820
ctacagcccc tactccatcc cggtgccggt cccggacggc agcagtctgc tcaccaccgc   2880
cctgccctcc atggcggcgg ccgcggggcc cctggacggc aaagtcgccg ccctggccgc   2940
cagcccggcc tcggtggcag tggactcggg ctctgaactc aacagccgct cctccacgct   3000
ctcctccagc tccatgtcct tgtcgcccaa actctgcgcg gagaaagagg cggccaccag   3060
cgaactgcag agcatccagc ggttggttag cggcttggaa gccaagccgg acaggtcccg   3120
cagcgcgtcc ccgtagaccc gtcccagaca cgtcttttca ttccagtcca gttcaggctg   3180
ccgtgcactt tgtcggatat aaaataaacc acgggcccgc catggcgtta gcccttcctt   3240
ttgcagttgc gtctgggaag ggcccccgga ctccctcgag agaatgtgct agagacagcc   3300
cctgtcttct tggcgtggtt tatatgtccg ggatctggat cagattctgg gggctcagaa   3360
acgtcggttg cattgagcta ctgggggtag gagttccaac atttatgtcc agagcaactt   3420
ccagcaaggc tggtctgggt ctctgcccac caggcgggga ggtgttcaaa gacatctccc   3480
tcagtgcgga tttatatata tatttttcct tcactgtgtc aagtggaaac aaaaacaaaa   3540
tctttcaaaa aaaaaatcgg gacaagtgaa cacattaaca tgattctgtt tgtgcagatt   3600
aaaaacttta tagggacttg cattatcggt tctcaataaa ttactgagca gctttgtttg   3660
gggagggaag tccctaccat ccttgtttag tctatattaa gaaaatctgt gtctttttaa   3720
tattcttgtg atgttttcag agccgctgta ggtctcttct tgcatgtcca cagtaatgta   3780
tttgtggttt ttattttgaa cgcttgcttt tagagagaaa acaatatagc cccctaccct   3840
tttcccaatc ctttgccctc aaatcagtga cccaagggag ggggggattt aaagggaagg   3900
agtgggcaaa acacataaaa tgaatttatt atatctaagc tctgtagcag gattcatgtc   3960
gttctttgac agttctttct ctttcctgta tatgcaataa caaggtttta aaaaaataat   4020
aaagaagtga gactattaga caaagtattt atgtaattat ttgataactc ttgtaaatag   4080
```

```
gtggaatatg aatgcttgga aaattaaact ttaatttatt gacattgtac atagctctgt   4140

gtaaatagaa ttgcaactgt caggttttgt gttcttgttt tcctttagtt gggtttattt   4200

ccaggtcaca gaattgctgt taacactaga aaacacactt cctgcaccaa caccaatacc   4260

ctttcaaaag agttgtctgc aacatttttg ttttcttttt taatgtccaa aagtggggga   4320

aagtgctatt tcctattttc accaaaattg ggaaggagt gccactttcc agctccactt   4380

caaattcctt aaaatataac tgagattgct gtggggaggg aggagggcag aggctgcggt   4440

ttgacttttt aatttttctt ttgttatttg tatttgctag tctctgattt cctcaaaacg   4500

aagtggaatt tactactgtt gtcagtatcg gtgttttgaa ttggtgcctg cctatagaga   4560

tatattcaca gttcaaaagt caggtgctga gagatggttt aaagacaaat tcatgaaggt   4620

atattttgtg ttatagttgt tgatgagttc tttggttttc tgtatttttc cccctctctt   4680

taaaacatca ctgaaatttc aataaatttt tattgaaatg tctaaaaaaa aaaaaaaaaa   4740

aaaaaaaaaa aaaa                                                     4754
```

<210> SEQ ID NO 2
<211> LENGTH: 723
<212> TYPE: PRT
<213> ORGANISM: Homo sapiens

<400> SEQUENCE: 2

```
Met Ser Leu Ser Met Arg Asp Pro Val Ile Pro Gly Thr Ser Met Ala
1               5                   10                  15

Tyr His Pro Phe Leu Pro His Arg Ala Pro Asp Phe Ala Met Ser Ala
            20                  25                  30

Val Leu Gly His Gln Pro Pro Phe Phe Pro Ala Leu Thr Leu Pro Pro
        35                  40                  45

Asn Gly Ala Ala Ala Leu Ser Leu Pro Gly Ala Leu Ala Lys Pro Ile
    50                  55                  60

Met Asp Gln Leu Val Gly Ala Ala Glu Thr Gly Ile Pro Phe Ser Ser
65                  70                  75                  80

Leu Gly Pro Gln Ala His Leu Arg Pro Leu Lys Thr Met Glu Pro Glu
                85                  90                  95

Glu Glu Val Glu Asp Asp Pro Lys Val His Leu Glu Ala Lys Glu Leu
            100                 105                 110

Trp Asp Gln Phe His Lys Arg Gly Thr Glu Met Val Ile Thr Lys Ser
        115                 120                 125

Gly Arg Arg Met Phe Pro Pro Phe Lys Val Arg Cys Ser Gly Leu Asp
    130                 135                 140

Lys Lys Ala Lys Tyr Ile Leu Leu Met Asp Ile Ile Ala Ala Asp Asp
145                 150                 155                 160

Cys Arg Tyr Lys Phe His Asn Ser Arg Trp Met Val Ala Gly Lys Ala
                165                 170                 175

Asp Pro Glu Met Pro Lys Arg Met Tyr Ile His Pro Asp Ser Pro Ala
            180                 185                 190

Thr Gly Glu Gln Trp Met Ser Lys Val Val Thr Phe His Lys Leu Lys
        195                 200                 205

Leu Thr Asn Asn Ile Ser Asp Lys His Gly Phe Thr Ile Leu Asn Ser
    210                 215                 220

Met His Lys Tyr Gln Pro Arg Phe His Ile Val Arg Ala Asn Asp Ile
225                 230                 235                 240

Leu Lys Leu Pro Tyr Ser Thr Phe Arg Thr Tyr Leu Phe Pro Glu Thr
                245                 250                 255
```

```
Glu Phe Ile Ala Val Thr Ala Tyr Gln Asn Asp Lys Ile Thr Gln Leu
            260                 265                 270

Lys Ile Asp Asn Asn Pro Phe Ala Lys Gly Phe Arg Asp Thr Gly Asn
        275                 280                 285

Gly Arg Arg Glu Lys Arg Lys Gln Leu Thr Leu Gln Ser Met Arg Val
    290                 295                 300

Phe Asp Glu Arg His Lys Lys Glu Asn Gly Thr Ser Asp Glu Ser Ser
305                 310                 315                 320

Ser Glu Gln Ala Ala Phe Asn Cys Phe Ala Gln Ala Ser Ser Pro Ala
                325                 330                 335

Ala Ser Thr Val Gly Thr Ser Asn Leu Lys Asp Leu Cys Pro Ser Glu
            340                 345                 350

Gly Glu Ser Asp Ala Glu Ala Glu Ser Lys Glu Glu His Gly Pro Glu
        355                 360                 365

Ala Cys Asp Ala Ala Lys Ile Ser Thr Thr Thr Ser Glu Glu Pro Cys
    370                 375                 380

Arg Asp Lys Gly Ser Pro Ala Val Lys Ala His Leu Phe Ala Ala Glu
385                 390                 395                 400

Arg Pro Arg Asp Ser Gly Arg Leu Asp Lys Ala Ser Pro Asp Ser Arg
                405                 410                 415

His Ser Pro Ala Thr Ile Ser Ser Ser Thr Arg Gly Leu Gly Ala Glu
            420                 425                 430

Glu Arg Arg Ser Pro Val Arg Glu Gly Thr Ala Pro Ala Lys Val Glu
        435                 440                 445

Glu Ala Arg Ala Leu Pro Gly Lys Glu Ala Phe Ala Pro Leu Thr Val
    450                 455                 460

Gln Thr Asp Ala Ala Ala Ala His Leu Ala Gln Gly Pro Leu Pro Gly
465                 470                 475                 480

Leu Gly Phe Ala Pro Gly Leu Ala Gly Gln Gln Phe Phe Asn Gly His
                485                 490                 495

Pro Leu Phe Leu His Pro Ser Gln Phe Ala Met Gly Gly Ala Phe Ser
            500                 505                 510

Ser Met Ala Ala Ala Gly Met Gly Pro Leu Leu Ala Thr Val Ser Gly
        515                 520                 525

Ala Ser Thr Gly Val Ser Gly Leu Asp Ser Thr Ala Met Ala Ser Ala
    530                 535                 540

Ala Ala Ala Gln Gly Leu Ser Gly Ala Ser Ala Ala Thr Leu Pro Phe
545                 550                 555                 560

His Leu Gln Gln His Val Leu Ala Ser Gln Gly Leu Ala Met Ser Pro
                565                 570                 575

Phe Gly Ser Leu Phe Pro Tyr Pro Tyr Thr Tyr Met Ala Ala Ala Ala
            580                 585                 590

Ala Ala Ser Ser Ala Ala Ala Ser Ser Ser Val His Arg His Pro Phe
        595                 600                 605

Leu Asn Leu Asn Thr Met Arg Pro Arg Leu Arg Tyr Ser Pro Tyr Ser
    610                 615                 620

Ile Pro Val Pro Val Pro Asp Gly Ser Ser Leu Leu Thr Thr Ala Leu
625                 630                 635                 640

Pro Ser Met Ala Ala Ala Ala Gly Pro Leu Asp Gly Lys Val Ala Ala
                645                 650                 655

Leu Ala Ala Ser Pro Ala Ser Val Ala Val Asp Ser Gly Ser Glu Leu
            660                 665                 670
```

-continued

```
Asn Ser Arg Ser Ser Thr Leu Ser Ser Ser Ser Met Ser Leu Ser Pro
        675                 680                 685

Lys Leu Cys Ala Glu Lys Glu Ala Ala Thr Ser Glu Leu Gln Ser Ile
    690                 695                 700

Gln Arg Leu Val Ser Gly Leu Glu Ala Lys Pro Asp Arg Ser Arg Ser
705                 710                 715                 720

Ala Ser Pro


<210> SEQ ID NO 3
<211> LENGTH: 4814
<212> TYPE: DNA
<213> ORGANISM: Homo sapiens

<400> SEQUENCE: 3

gaattctaga ggcggcggag ggtggcgagg agctctcgct ttctctcgct ccctccctct     60

ccgactccgt ctctctctct ctctctctct ctcccctccc tctctttccc tctgttccat    120

tttttccccc tctaaatcct ccctgccctg cgcgcctgga cacagattta ggaagcgaat    180

tcgctcacgt tttaggacaa ggaagagaga gaggcacggg agaagagccc agcaagattt    240

ggattgaaac cgagacaccc tccggaggct cggagcagag gaaggaggag gagggcggcg    300

aacggaagcc agtttgcaat tcaagttttg atagcgctgg tagaaggggg tttaaatcag    360

attttttttt ttttaaagga gagagacttt ttccgctctc tcgctccctg ttaaagccgg    420

gtctagcaca gctgcagacg ccaccagcga gaaagaggga gaggaagaca gatagggggc    480

gggggaagaa gaaaaagaaa ggtaaaaagt cttctaggag aacctttcac atttgcaaca    540

aaagacctag ggctggagaa gagattcctg ggacgcaggg ctggagtgtc tatttcgagc    600

tcagcggcag ggctcgggcg cgagtcgaga ccctgctcgc tcctctcgct tctgaaaccg    660

acgttcagga gcggcttttt aaaaacgcaa ggcacaagga cggtcacccg cgcgactatg    720

tttgctgatt tttcgccttg ccctctttaa aagcggcctc ccattctcca aaagacactt    780

cccctcctcc ctttgaagtg cattagttgt gatttctgcc tccttttctt ttttctttct    840

tttttgtttt gctttttccc ccctttttgaa ttatgtgctg ctgttaaaca acaacaaaaa    900

aacaacaaaa cacagcagct gcggacttgt ccccggctgg agcccagcgc cccgcctgga    960

gtggatgagc ctctccatga gagatccggt cattcctggg acaagcatgg cctaccatcc   1020

gttcctacct caccgggcgc cggacttcgc catgagcgcg gtgctgggtc accagccgcc   1080

gttcttcccc gcgctgacgc tgcctcccaa cggcgcggcg gcgctctcgc tgccgggcgc   1140

cctggccaag ccgatcatgg atcaattggt gggggcggcc gagaccggca tcccgttctc   1200

ctccctgggg ccccaggcgc atctgaggcc tttgaagacc atggagcccg aagaagaggt   1260

ggaggacgac cccaaggtgc acctggaggc taaagaactt tgggatcagt ttcacaagcg   1320

gggcaccgag atggtcatta ccaagtcggg aaggcgaatg tttcctccat ttaaagtgag   1380

atgttctggg ctggataaaa aagccaaata cattttattg atggacatta tagctgctga   1440

tgactgtcgt tataaatttc acaattctcg gtggatggtg gctggtaagg ccgaccccga   1500

aatgccaaag aggatgtaca ttcacccgga cagccccgct actggggaac agtggatgtc   1560

caaagtcgtc actttccaca aactgaaact caccaacaac atttcagaca aacatggatt   1620

tactttggcc ttcccaagtg atcacgctac gtggcagggg aattatagtt ttggtactca   1680

gactatattg aactccatgc acaaatacca gccccggttc cacattgtaa gagccaatga   1740

catcttgaaa ctcccttata gtacatttcg gacatacttg ttccccgaaa ctgaattcat   1800
```

```
cgctgtgact gcataccaga atgataagat aacccagtta aaaatagaca acaacccttt   1860
tgcaaaaggt ttccgggaca ctggaaatgg ccgaagagaa aaaagaaaac agctcaccct   1920
gcagtccatg agggtgtttg atgaaagaca caaaaaggag aatgggacct ctgatgagtc   1980
ctccagtgaa caagcagctt tcaactgctt cgcccaggct tcttctccag ccgcctccac   2040
tgtagggaca tcgaacctca aagatttatg tcccagcgag ggtgagagcg acgccgaggc   2100
cgagagcaaa gaggagcatg gccccgaggc ctgcgacgcg gccaagatct ccaccaccac   2160
gtcggaggag ccctgccgtg acaagggcag ccccgcggtc aaggctcacc ttttcgctgc   2220
tgagcggccc cgggacagcg ggcggctgga caaagcgtcg cccgactcac gccatagccc   2280
cgccaccatc tcgtccagca ctcgcggcct gggcgcggag gagcgcagga gcccggttcg   2340
cgagggcaca gcgccggcca aggtggaaga ggcgcgcgcg ctcccgggca aggaggcctt   2400
cgcgccgctc acggtgcaga cggacgcggc cgccgcgcac ctggcccagg gcccccctgcc  2460
tggcctcggc ttcgccccgg gcctggcggg ccaacagttc ttcaacgggc acccgctctt   2520
cctgcacccc agccagtttg ccatgggggg cgccttctcc agcatggcgg ccgctggcat   2580
gggtcccctc ctggccacgg tttctggggc ctccaccggt gtctcgggcc tggattccac   2640
ggccatggcc tctgccgctg cggcgcaggg actgtccggg gcgtccgcgg ccaccctgcc   2700
cttccacctc cagcagcacg tcctggcctc tcagggcctg gccatgtccc ctttcggaag   2760
cctgttccct taccccctaca cgtacatggc cgcagcggcg gccgcctcct ctgcggcagc  2820
ctccagctcg gtgcaccgcc acccccttcct caatctgaac accatgcgcc cgcggctgcg  2880
ctacagcccc tactccatcc cggtgccggt cccggacggc agcagtctgc tcaccaccgc   2940
cctgccctcc atggcggcgg ccgcggggcc cctggacggc aaagtcgccg ccctggccgc   3000
cagcccggcc tcggtggcag tggactcggg ctctgaactc aacagccgct cctccacgct   3060
ctcctccagc tccatgtcct tgtcgcccaa actctgcgcg gagaaagagg cggccaccag   3120
cgaactgcag agcatccagc ggttggttag cggcttggaa gccaagccgg acaggtcccg   3180
cagcgcgtcc ccgtagaccc gtcccagaca cgtcttttca ttccagtcca gttcaggctg   3240
ccgtgcactt tgtcggatat aaaataaacc acgggcccgc catggcgtta gcccttcctt   3300
ttgcagttgc gtctgggaag ggcccccgga ctccctcgag agaatgtgct agagacagcc   3360
cctgtcttct tggcgtggtt tatatgtccg ggatctggat cagattctgg gggctcagaa   3420
acgtcggttg cattgagcta ctgggggtag gagttccaac atttatgtcc agagcaactt   3480
ccagcaaggc tggtctgggt ctctgcccac caggcgggga ggtgttcaaa gacatctccc   3540
tcagtgcgga tttatatata tatttttcct tcactgtgtc aagtggaaac aaaaacaaaa   3600
tctttcaaaa aaaaaatcgg gacaagtgaa cacattaaca tgattctgtt tgtgcagatt   3660
aaaaacttta tagggacttg cattatcggt tctcaataaa ttactgagca gctttgtttg   3720
gggagggaag tccctaccat ccttgtttag tctatattaa gaaaatctgt gtctttttaa   3780
tattcttgtg atgttttcag agccgctgta ggtctcttct tgcatgtcca cagtaatgta   3840
tttgtggttt ttattttgaa cgcttgcttt tagagagaaa acaatatagc cccctaccct   3900
tttcccaatc ctttgccctc aaatcagtga cccaagggag ggggggattt aaagggaagg   3960
agtgggcaaa acacataaaa tgaatttatt atatctaagc tctgtagcag gattcatgtc   4020
gttctttgac agttctttct ctttcctgta tatgcaataa caaggtttta aaaaaataat   4080
aaagaagtga gactattaga caaagtattt atgtaattat ttgataactc ttgtaaatag   4140
gtggaatatg aatgcttgga aaattaaact ttaatttatt gacattgtac atagctctgt   4200
```

```
gtaaatagaa ttgcaactgt caggttttgt gttcttgttt tcctttagtt gggtttattt   4260

ccaggtcaca gaattgctgt taacactaga aaacacactt cctgcaccaa caccaatacc   4320

ctttcaaaag agttgtctgc aacatttttg ttttcttttt taatgtccaa aagtggggga   4380

aagtgctatt tcctattttc accaaaattg gggaaggagt gccactttcc agctccactt   4440

caaattcctt aaaatataac tgagattgct gtggggaggg aggagggcag aggctgcggt   4500

ttgacttttt aatttttctt ttgttatttg tatttgctag tctctgattt cctcaaaacg   4560

aagtggaatt tactactgtt gtcagtatcg gtgttttgaa ttggtgcctg cctatagaga   4620

tatattcaca gttcaaaagt caggtgctga gagatggttt aaagacaaat tcatgaaggt   4680

atattttgtg ttatagttgt tgatgagttc tttggttttc tgtatttttc cccctctctt   4740

taaaacatca ctgaaatttc aataaatttt tattgaaatg tctaaaaaaa aaaaaaaaaa   4800

aaaaaaaaaa aaaa                                                     4814
```

```
<210> SEQ ID NO 4
<211> LENGTH: 743
<212> TYPE: PRT
<213> ORGANISM: Homo sapiens

<400> SEQUENCE: 4

Met Ser Leu Ser Met Arg Asp Pro Val Ile Pro Gly Thr Ser Met Ala
1               5                   10                  15

Tyr His Pro Phe Leu Pro His Arg Ala Pro Asp Phe Ala Met Ser Ala
            20                  25                  30

Val Leu Gly His Gln Pro Pro Phe Phe Pro Ala Leu Thr Leu Pro Pro
        35                  40                  45

Asn Gly Ala Ala Ala Leu Ser Leu Pro Gly Ala Leu Ala Lys Pro Ile
    50                  55                  60

Met Asp Gln Leu Val Gly Ala Ala Glu Thr Gly Ile Pro Phe Ser Ser
65                  70                  75                  80

Leu Gly Pro Gln Ala His Leu Arg Pro Leu Lys Thr Met Glu Pro Glu
                85                  90                  95

Glu Glu Val Glu Asp Asp Pro Lys Val His Leu Glu Ala Lys Glu Leu
            100                 105                 110

Trp Asp Gln Phe His Lys Arg Gly Thr Glu Met Val Ile Thr Lys Ser
        115                 120                 125

Gly Arg Arg Met Phe Pro Pro Phe Lys Val Arg Cys Ser Gly Leu Asp
    130                 135                 140

Lys Lys Ala Lys Tyr Ile Leu Leu Met Asp Ile Ile Ala Ala Asp Asp
145                 150                 155                 160

Cys Arg Tyr Lys Phe His Asn Ser Arg Trp Met Val Ala Gly Lys Ala
                165                 170                 175

Asp Pro Glu Met Pro Lys Arg Met Tyr Ile His Pro Asp Ser Pro Ala
            180                 185                 190

Thr Gly Glu Gln Trp Met Ser Lys Val Val Thr Phe His Lys Leu Lys
        195                 200                 205

Leu Thr Asn Asn Ile Ser Asp Lys His Gly Phe Thr Leu Ala Phe Pro
    210                 215                 220

Ser Asp His Ala Thr Trp Gln Gly Asn Tyr Ser Phe Gly Thr Gln Thr
225                 230                 235                 240

Ile Leu Asn Ser Met His Lys Tyr Gln Pro Arg Phe His Ile Val Arg
                245                 250                 255
```

```
Ala Asn Asp Ile Leu Lys Leu Pro Tyr Ser Thr Phe Arg Thr Tyr Leu
            260                 265                 270

Phe Pro Glu Thr Glu Phe Ile Ala Val Thr Ala Tyr Gln Asn Asp Lys
        275                 280                 285

Ile Thr Gln Leu Lys Ile Asp Asn Asn Pro Phe Ala Lys Gly Phe Arg
    290                 295                 300

Asp Thr Gly Asn Gly Arg Arg Glu Lys Arg Lys Gln Leu Thr Leu Gln
305                 310                 315                 320

Ser Met Arg Val Phe Asp Glu Arg His Lys Lys Glu Asn Gly Thr Ser
                325                 330                 335

Asp Glu Ser Ser Ser Glu Gln Ala Ala Phe Asn Cys Phe Ala Gln Ala
            340                 345                 350

Ser Ser Pro Ala Ala Ser Thr Val Gly Thr Ser Asn Leu Lys Asp Leu
        355                 360                 365

Cys Pro Ser Glu Gly Glu Ser Asp Ala Glu Ala Glu Ser Lys Glu Glu
    370                 375                 380

His Gly Pro Glu Ala Cys Asp Ala Ala Lys Ile Ser Thr Thr Thr Ser
385                 390                 395                 400

Glu Glu Pro Cys Arg Asp Lys Gly Ser Pro Ala Val Lys Ala His Leu
                405                 410                 415

Phe Ala Ala Glu Arg Pro Arg Asp Ser Gly Arg Leu Asp Lys Ala Ser
            420                 425                 430

Pro Asp Ser Arg His Ser Pro Ala Thr Ile Ser Ser Ser Thr Arg Gly
        435                 440                 445

Leu Gly Ala Glu Glu Arg Arg Ser Pro Val Arg Glu Gly Thr Ala Pro
    450                 455                 460

Ala Lys Val Glu Glu Ala Arg Ala Leu Pro Gly Lys Glu Ala Phe Ala
465                 470                 475                 480

Pro Leu Thr Val Gln Thr Asp Ala Ala Ala Ala His Leu Ala Gln Gly
                485                 490                 495

Pro Leu Pro Gly Leu Gly Phe Ala Pro Gly Leu Ala Gly Gln Gln Phe
            500                 505                 510

Phe Asn Gly His Pro Leu Phe Leu His Pro Ser Gln Phe Ala Met Gly
        515                 520                 525

Gly Ala Phe Ser Ser Met Ala Ala Ala Gly Met Gly Pro Leu Leu Ala
    530                 535                 540

Thr Val Ser Gly Ala Ser Thr Gly Val Ser Gly Leu Asp Ser Thr Ala
545                 550                 555                 560

Met Ala Ser Ala Ala Ala Ala Gln Gly Leu Ser Gly Ala Ser Ala Ala
                565                 570                 575

Thr Leu Pro Phe His Leu Gln Gln His Val Leu Ala Ser Gln Gly Leu
            580                 585                 590

Ala Met Ser Pro Phe Gly Ser Leu Phe Pro Tyr Pro Tyr Thr Tyr Met
        595                 600                 605

Ala Ala Ala Ala Ala Ala Ser Ser Ala Ala Ala Ser Ser Ser Val His
    610                 615                 620

Arg His Pro Phe Leu Asn Leu Asn Thr Met Arg Pro Arg Leu Arg Tyr
625                 630                 635                 640

Ser Pro Tyr Ser Ile Pro Val Pro Val Pro Asp Gly Ser Ser Leu Leu
                645                 650                 655

Thr Thr Ala Leu Pro Ser Met Ala Ala Ala Ala Gly Pro Leu Asp Gly
            660                 665                 670

Lys Val Ala Ala Leu Ala Ala Ser Pro Ala Ser Val Ala Val Asp Ser
```

```
        675                 680                 685

Gly Ser Glu Leu Asn Ser Arg Ser Ser Thr Leu Ser Ser Ser Ser Met
    690                 695                 700

Ser Leu Ser Pro Lys Leu Cys Ala Glu Lys Glu Ala Ala Thr Ser Glu
705                 710                 715                 720

Leu Gln Ser Ile Gln Arg Leu Val Ser Gly Leu Glu Ala Lys Pro Asp
                725                 730                 735

Arg Ser Arg Ser Ala Ser Pro
            740


<210> SEQ ID NO 5
<211> LENGTH: 600
<212> TYPE: PRT
<213> ORGANISM: Homo sapiens

<400> SEQUENCE: 5

Met Ser Leu Ser Met Arg Asp Pro Val Ile Pro Gly Thr Ser Met Ala
1               5                   10                  15

Tyr His Pro Phe Leu Pro His Arg Ala Pro Asp Phe Ala Met Ser Ala
            20                  25                  30

Val Leu Gly His Gln Pro Pro Phe Phe Pro Ala Leu Thr Leu Pro Pro
        35                  40                  45

Asn Gly Ala Ala Ala Leu Ser Leu Pro Gly Ala Leu Ala Lys Pro Ile
    50                  55                  60

Met Asp Gln Leu Val Gly Ala Ala Glu Thr Gly Ile Pro Phe Ser Ser
65                  70                  75                  80

Leu Gly Pro Gln Ala His Leu Arg Pro Leu Lys Thr Met Glu Pro Glu
                85                  90                  95

Glu Glu Val Glu Asp Asp Pro Lys Val His Leu Glu Ala Lys Glu Leu
            100                 105                 110

Trp Asp Gln Phe His Lys Arg Gly Thr Glu Met Val Ile Thr Lys Ser
        115                 120                 125

Gly Arg Arg Met Phe Pro Pro Phe Lys Val Arg Cys Ser Gly Leu Asp
    130                 135                 140

Lys Lys Ala Lys Tyr Ile Leu Leu Met Asp Ile Ile Ala Ala Asp Asp
145                 150                 155                 160

Cys Arg Tyr Lys Phe His Asn Ser Arg Trp Met Val Ala Gly Lys Ala
                165                 170                 175

Asp Pro Glu Met Pro Lys Arg Met Tyr Ile His Pro Asp Ser Pro Ala
            180                 185                 190

Thr Gly Glu Gln Trp Met Ser Lys Val Val Thr Phe His Lys Leu Lys
        195                 200                 205

Leu Thr Asn Asn Ile Ser Asp Lys His Gly Phe Thr Leu Ala Phe Pro
    210                 215                 220

Ser Asp His Ala Thr Trp Gln Gly Asn Tyr Ser Phe Gly Thr Gln Thr
225                 230                 235                 240

Ile Leu Asn Ser Met His Lys Tyr Gln Pro Arg Phe His Ile Val Arg
                245                 250                 255

Ala Asn Asp Ile Leu Lys Leu Pro Tyr Ser Thr Phe Arg Thr Tyr Leu
            260                 265                 270

Phe Pro Glu Thr Glu Phe Ile Ala Val Thr Ala Tyr Gln Asn Asp Lys
        275                 280                 285

Ile Thr Gln Leu Lys Ile Asp Asn Asn Pro Phe Ala Lys Gly Phe Arg
    290                 295                 300
```

```
Asp Thr Gly Asn Gly Arg Arg Glu Lys Arg Lys Gln Leu Thr Leu Gln
305                 310                 315                 320

Ser Met Arg Val Phe Asp Glu Arg His Lys Lys Glu Asn Gly Thr Ser
                325                 330                 335

Asp Glu Ser Ser Ser Glu Gln Ala Ala Phe Asn Cys Phe Ala Gln Ala
            340                 345                 350

Ser Ser Pro Ala Ala Ser Thr Val Gly Thr Ser Asn Leu Lys Asp Leu
        355                 360                 365

Cys Pro Ser Glu Gly Glu Ser Asp Ala Glu Ala Glu Ser Lys Glu Glu
    370                 375                 380

His Gly Pro Glu Ala Cys Asp Ala Ala Lys Ile Ser Thr Thr Thr Ser
385                 390                 395                 400

Glu Glu Pro Cys Arg Asp Lys Gly Ser Pro Ala Val Lys Ala His Leu
                405                 410                 415

Phe Ala Ala Glu Arg Pro Arg Asp Ser Gly Arg Leu Asp Lys Ala Ser
            420                 425                 430

Pro Asp Ser Arg His Ser Pro Ala Thr Ile Ser Ser Ser Thr Arg Gly
        435                 440                 445

Leu Gly Ala Glu Glu Arg Arg Ser Pro Val Arg Glu Gly Thr Ala Pro
    450                 455                 460

Ala Lys Val Glu Glu Ala Arg Ala Leu Pro Gly Lys Glu Ala Phe Ala
465                 470                 475                 480

Pro Leu Thr Val Gln Thr Asp Ala Ala Ser Ala Ala Ala Ser Ser Ser
                485                 490                 495

Val His Arg His Pro Phe Leu Asn Leu Asn Thr Met Arg Pro Arg Leu
            500                 505                 510

Arg Tyr Ser Pro Tyr Ser Ile Pro Val Pro Val Pro Asp Gly Ser Ser
        515                 520                 525

Leu Leu Thr Thr Ala Leu Ala Ala Ser Pro Ala Ser Val Ala Val Asp
    530                 535                 540

Ser Gly Ser Glu Leu Asn Ser Arg Ser Ser Thr Leu Ser Ser Ser Ser
545                 550                 555                 560

Met Ser Leu Ser Pro Lys Leu Cys Ala Glu Lys Glu Ala Ala Thr Ser
                565                 570                 575

Glu Leu Gln Ser Ile Gln Arg Leu Val Ser Gly Leu Glu Ala Lys Pro
            580                 585                 590

Asp Arg Ser Arg Ser Ala Ser Pro
        595                 600


<210> SEQ ID NO 6
<211> LENGTH: 19
<212> TYPE: DNA
<213> ORGANISM: Artificial sequence
<220> FEATURE:
<223> OTHER INFORMATION: Synthetic sequence: Sequence targeted by shRNA

<400> SEQUENCE: 6

gagccaacga tatcctgaa                                                19


<210> SEQ ID NO 7
<211> LENGTH: 19
<212> TYPE: DNA
<213> ORGANISM: Artificial sequence
<220> FEATURE:
<223> OTHER INFORMATION: Synthetic sequence: Control shRNA sequence

<400> SEQUENCE: 7
```

```
gatgaaatgg gtaagtaca                                                  19


<210> SEQ ID NO 8
<211> LENGTH: 20
<212> TYPE: DNA
<213> ORGANISM: Artificial sequence
<220> FEATURE:
<223> OTHER INFORMATION: Synthetic sequence: Forward primer

<400> SEQUENCE: 8

aaagcaactc agagggaacc                                                 20


<210> SEQ ID NO 9
<211> LENGTH: 20
<212> TYPE: DNA
<213> ORGANISM: Artificial sequence
<220> FEATURE:
<223> OTHER INFORMATION: Synthetic sequence: Reverse primer

<400> SEQUENCE: 9

ggcagaggaa aggatacagc                                                 20


<210> SEQ ID NO 10
<211> LENGTH: 20
<212> TYPE: DNA
<213> ORGANISM: Artificial sequence
<220> FEATURE:
<223> OTHER INFORMATION: Synthetic sequence: Forward primer

<400> SEQUENCE: 10

agaaccccaa gatgcacaac                                                 20


<210> SEQ ID NO 11
<211> LENGTH: 21
<212> TYPE: DNA
<213> ORGANISM: Artificial sequence
<220> FEATURE:
<223> OTHER INFORMATION: Synthetic sequence: Reverse primer

<400> SEQUENCE: 11

agtgggagga agaggtaacc a                                               21


<210> SEQ ID NO 12
<211> LENGTH: 20
<212> TYPE: DNA
<213> ORGANISM: Artificial sequence
<220> FEATURE:
<223> OTHER INFORMATION: Synthetic sequence: Forward primer

<400> SEQUENCE: 12

tttgtgctga aggcgtctct                                                 20


<210> SEQ ID NO 13
<211> LENGTH: 19
<212> TYPE: DNA
<213> ORGANISM: Artificial sequence
<220> FEATURE:
<223> OTHER INFORMATION: Synthetic sequence: Reverse primer

<400> SEQUENCE: 13

tgtgtgtttg cggtagtgc                                                  19


<210> SEQ ID NO 14
<211> LENGTH: 20
<212> TYPE: DNA
<213> ORGANISM: Artificial sequence
```

<220> FEATURE:
<223> OTHER INFORMATION: Synthetic sequence: Forward primer

<400> SEQUENCE: 14
agagtgtttg aggagaggca 20

<210> SEQ ID NO 15
<211> LENGTH: 20
<212> TYPE: DNA
<213> ORGANISM: Artificial sequence
<220> FEATURE:
<223> OTHER INFORMATION: Synthetic sequence: Reverse primer

<400> SEQUENCE: 15
taggggtaag gaaacaggct 20

<210> SEQ ID NO 16
<211> LENGTH: 3480
<212> TYPE: DNA
<213> ORGANISM: Mus musculus

<400> SEQUENCE: 16
cctttgcctc cggacttctc tggggccagc agccgcccga cctggggccc ggggccacgg 60
gctcagcaga cgaccatggg ctcggtgtcc aaccagcagt ttgcaggtgg ctgcgccaag 120
gcagcggaga aggcgccaga ggaggcgccg cctgacgcgg cccgagcggc agacgagccg 180
cagctgctgc acggggccgg catctgtaag tggttcaacg tgcgcatggg gttcggcttc 240
ctgtctatga ccgcccgcgc tggggtcgcg ctcgaccccc cggtggacgt ctttgtgcac 300
cagagcaagc tgcacatgga agggttccga agcctcaagg agggtgaggc ggtggagttc 360
acctttaaga agtctgccaa gggtctggaa tccatccgtg tcactggccc tggtggtgtg 420
ttctgtattg ggagtgagcg gcggccaaaa gggaagaaca tgcagaagcg aagatccaaa 480
ggagacaggt gctacaactg cggtgggcta gaccatcatg ccaaggaatg caagctgcca 540
ccccagccca agaagtgcca cttttgccaa agcatcaacc atatggtggc ctcgtgtcca 600
ctgaaggccc agcagggccc cagttctcag ggaaagcctg cctacttccg ggaggaagag 660
gaagagatcc acagccctgc cctgctccca gaagcccaga attgaggccc aggagtcagg 720
gttattcttt ggctaatggg gagtttaagg aaagaggcat caatctgcag agtggagaaa 780
gtgggggtaa gggtgggttg cgtgggtagc ttgcactgcc gtgtctcagg ccggggttcc 840
cagtgtcacc ctgtctttcc ttggagggaa ggaaaggatg agacaaagga actcctacca 900
cactctatct gaaagcaagt gaaggctttt gtggggagga accaccctag aacccgaggc 960
tttgccaagt ggctgggcta gggaagttct tttgtagaag gctgtgtgat atttcccttg 1020
ccagacggga agcgaaacaa gtgtcaaacc aagattactg aacctacccc tccagctact 1080
atgttctggg gaagggactc ccaggagcag ggcgaggtta ttttcacacc gtgcttattc 1140
ataaccctgt cctttggtgc tgtgctggga atggtctcta gcaacgggtt gtgatgacag 1200
gcaaagaggg tggttgggga gacaactgct gacctgctgc ccacacctca ctcccagccc 1260
tttctgggcc aatgggattt taatttattt gctcccttag gtaactgcac cttgggtccc 1320
actttctcca ggatgccaac tgcactatct acgtgcgaat gacgtatctt gtgcgttttt 1380
ttttttttta atttttaaaa ttttttttca tcttcttaat ataaataatg ggtttgtatt 1440
tttgtatatt ttaatcttaa ggccctcatt cctgcactgt gttctcaggt acatgagcaa 1500
tctcagggat aataagtccg tagcagctcc aggtctgctc agcaggaata ctttgttttg 1560

```
ttttgttttg atcaccatgg agaccaacca tttggagtgc acagcctgtt gaactacctc   1620
atttttgccg attacagctg gcttttctgc catagcgtcc ttgaaaaatg tgtctcacgg   1680
gtttcgattg agctgcccca agacttgatc tggatttggc aaaacatagg acatcactct   1740
aaacaggaaa gggtggtaca gagacattaa aaggctgggc caggtgaaag gcacaagagg   1800
aactttccat accagatcca tccttttgcc agattagtgg aagcctgcca tgcacagcag   1860
ggtgtgagag agagagtgtg tatgtatgtg tgtgtggatt ttttttaatg caaatttatg   1920
aagacgaggt gggttttgtt tatttgattg ctttttgtgc tggggatgga atcttgggct   1980
tcatttgtgc taggaagtac actgccactg agttatccca gtaagaatgc aacttaagac   2040
cagtaccctt attcccacac tgtgctgtcc aggcatggga acatgaggca gggactcaac   2100
tccttagcct ttcacaatct tggctttctg agagactcat gagtatgggc ctcagtggca   2160
agtgtcctgc cctgctgtag cgtgatggtt gatagctaaa ggaaagaggg ggtggggagt   2220
ttcgtttaca tgctttgaga tcgccacaaa cctacctcac tgtgttgaaa cgggacaaat   2280
gcaatagaac acattgggtg gtgtgtgtgt gtgtctgatc ttggtttctt gtctccctct   2340
ccccccaaat gctgccctca cccctagtta attgtattcg tctggccttt gtaggacttt   2400
tactgtctct gagttggtga ttgctaggtg gcctagttgt gtaaatataa atgtgttggt   2460
cttcatgttc ttttggggtt ttattgttta caaaactttt gttgtattga gagaaaaata   2520
gccaaagcat ctttgacaga aagctctgca ccagacaaca ccatctgaaa cttaaatgtg   2580
cggtcctctt ctcaaagtga acctctggga ccatggctta tccttacctg ttcctcctgt   2640
gtctcccatt ctggaccaca gtgaccttca gacagcccct cttctccctc gtaagaaaac   2700
ttaggctcat ttacttcttt gagcatctct gtaactcttg aaggacccat gtgaaaattc   2760
tgaagaagcc aggaacctca ttctttcctt gtccctaact cagtgaagag ttttggttgg   2820
tggttttgag acagggcctc actctgtagc tggagataga gagcctcggg ttcctggctc   2880
tcctcctgcc ttctgcacag agtcccctgt gcagggattg caggtgccgc ttctccctgg   2940
caagaccatt tatttcatgg tgtgattcgc ctttggatgg atcaaaccaa tgtaatctgt   3000
cacccttagg tcgagagaag caattgtggg gccttccatg tagaaagttg gaatctggac   3060
accagaaaag ggactatgaa tgtacagtga gtcactcagg aacttaatgc cggtgcaaga   3120
aacttatgtc aaagaggcca caagattgtt actaggagac ggacgaatgt atctccatgt   3180
ttactgctag aaaccaaagc tttgtgagaa atcttgaatt tatggggagg gtgggaaagg   3240
gtgtacttgt ctgtcctttc cccatctctt tcctgaactg caggagacta aggcccccca   3300
ccccccgggg cttggatgac ccccacccct gcctggggtg ttttatttcc tagttgattt   3360
ttactgtacc cgggcccttg tattcctatc gtataatcat cctgtgacac atgctgactt   3420
ttccttccct tctcttccct gggaaaataa agacttattg gtactccaga gttggtactg   3480
```

```
<210> SEQ ID NO 17
<211> LENGTH: 4014
<212> TYPE: DNA
<213> ORGANISM: Homo sapiens

<400> SEQUENCE: 17

gtgcggggga agatgtagca gcttcttctc cgaaccaacc ctttgccttc ggacttctcc     60
ggggccagca gccgcccgac caggggcccg gggccacggg ctcagccgac gaccatgggc    120
tccgtgtcca accagcagtt tgcaggtggc tgcgccaagg cggcagaaga ggcgcccgag    180
gaggcgccgg aggacgcggc ccgggcggcg gacgagcctc agctgctgca cggtgcgggc    240
```

```
atctgtaagt ggttcaacgt gcgcatgggg ttcggcttcc tgtccatgac cgcccgcgcc    300
ggggtcgcgc tcgacccccc agtggatgtc tttgtgcacc agagtaagct gcacatggaa    360
gggttccgga gcttgaagga gggtgaggca gtggagttca cctttaagaa gtcagccaag    420
ggtctggaat ccatccgtgt caccggacct ggtggagtat tctgtattgg gagtgagagg    480
cggccaaaag gaaagagcat gcagaagcgc agatcaaaag gagacaggtg ctacaactgt    540
ggaggtctag atcatcatgc caaggaatgc aagctgccac cccagcccaa gaagtgccac    600
ttctgccaga gcatcagcca tatggtagcc tcatgtccgc tgaaggccca gcagggccct    660
agtgcacagg gaaagccaac ctactttcga gaggaagaag aagaaatcca cagccctacc    720
ctgctcccgg aggcacagaa ttgagccaca atgggtgggg gctattcttt tgctatcagg    780
aagttttgag gagcaggcag agtggagaaa gtgggaatag ggtgcattgg ggctagttgg    840
cactgccatg tatctcaggc ttgggttcac accatcaccc tttcttccct ctaggtgggg    900
ggaaagggtg agtcaaagga actccaacca tgctctgtcc aaatgcaagt gagggttctg    960
ggggcaacca ggagggggga atcaccctac aacctgcata ctttgagtct ccatccccag   1020
aatttccagc ttttgaaagt ggcctggata gggaagttgt tttcctttta aagaaggata   1080
tataataatt cccatgccag agtgaaatga ttaagtataa gaccagattc atggagccaa   1140
gccactacat tctgtggaag gagatctctc aggagtaagc attgtttttt tttcacatct   1200
tgtatcctca tacccacttt tgggataggg tgctggcagc tgtcccaagc aatgggtaat   1260
gatgatggca aaaagggtgt ttgggggaac agctgcagac ctgctgctct atgctcaccc   1320
ccgccccatt ctgggccaat gtgattttat ttatttgctc ccttggatac tgcaccttgg   1380
gtcccacttt ctccaggatg ccaactgcac tagctgtgtg cgaatgacgt atcttgtgca   1440
ttttaacttt ttttccttaa tataaatatt ctggttttgt atttttgtat attttaatct   1500
aaggccctca tttcctgcac tgtgttctca ggtacatgag caatctcagg gatagccagc   1560
agcagctcca ggtctgcgca gcaggaatta ctttttgttg tttttgccac cgtggagagc   1620
aactatttgg agtgcacagc ctattgaact acctcatttt tgccaataag agctggcttt   1680
tctgccatag tgtcctcttg aaacccccctc tgccttgaaa atgttttatg ggagactagg   1740
ttttaactgg gtggccccat gacttgattg ccttctactg gaagattggg aattagtcta   1800
aacaggaaat ggtggtacac agaggctagg agaggctggg cccggtgaaa aggccagaga   1860
gcaagccaag attaggtgag ggttgtctaa tcctatggca caggacgtgc tttacatctc   1920
cagatctgtt cttcaccaga ttaggttagg cctaccatgt gccacagggt gtgtgtgtgt   1980
ttgtaaaact agagttgcta aggataagtt taaagaccaa taccccctgta cttaatcctg   2040
tgctgtcgag ggatggatat atgaagtaag gtgagatcct taacctttca aaattttcgg   2100
gttccaggga gacacacaag cgagggtttt gtggtgcctg gagcctgtgt cctgccctgc   2160
tacagtagtg attaatagtg tcatggtagc taaaggagaa aaagggggtt tcgtttacac   2220
gctgtgagat caccgcaaac ctaccttact gtgttgaaac gggacaaatg caatagaacg   2280
cattgggtgg tgtgtgtctg atcctgggtt cttgtctccc ctaaatgctg ccccccaagt   2340
tactgtattt gtctgggctt tgtaggactt cactacgttg attgctaggt ggcctagttt   2400
gtgtaaatat aatgtattgg tctttctccg tgttctttgg gggttttgtt tacaaacttc   2460
tttttgtatt gagagaaaaa tagccaaagc atctttgaca gaaggttctg caccaggcaa   2520
aaagatctga aacattagtt tggggggccc tcttcttaaa gtggggatct tgaaccatcc   2580
```

```
tttcttttgt attcccttc ccctattacc tattagacca gatcttctgt cctaaaaact   2640

tgtcttctac cctgccctct tttctgttca cccccaaaag aaaacttaca cacccacaca   2700

catacacatt tcatgcttgg agtgtctcca caactcttaa atgatgtatg caaaaatact   2760

gaagctagga aaaccctcca tcccttgttc ccaacctcct aagtcaagac cattaccatt   2820

tctttctttc tttttttttt ttttttaaaa tggagtctca ctgtgtcacc caggctggag   2880

tgcagtggca tgatcggctc actgcagcct ctgcctcttg ggttcaagtg attctcctgc   2940

ctcagcctcc tgagtagctg ggatttcagg cacccgccac actcagctaa tttttgtatt   3000

tttagtagag acggggtttc accatgttgt ccaggctggt ctggaactcc tgacctcagg   3060

tgatctgccc accttggctt cccaaagtgc tgggattaca ggcatgagcc accatgctgg   3120

gccaaccatt tcttggtgta ttcatgccaa acacttaaga cactgctgta gcccaggcgc   3180

ggtggctcac acctgtaatc ccagcacttt ggaaggctga ggcgggcgga tcacaaggtc   3240

acgagttcaa aactatcctg gccaacacag tgaaaccccg tctctactaa aatacaaaaa   3300

aattagccgg gtgtggtggt gcatgccttt agtcctagct attcaggagg ctgaggcagg   3360

ggaatcgctt gaacccgaga ggcagaggtt gcagtgagct gagatcgcac cactgcactc   3420

cagcctggtt acagagcaag actctgtctc aaacaaaaca aaacaaaaca aaaacacact   3480

actgtatttt ggatggatca aacctcctta attttaattt ctaatcctaa agtaaagaga   3540

tgcaattggg ggccttccat gtagaaagtg gggtcaggag gccaagaaag ggaatatgaa   3600

tgtatatcca agtcactcag gaacttttat gcaggtgcta gaaactttat gtcaaagtgg   3660

ccacaagatt gtttaatagg agacgaacga atgtaactcc atgtttactg ctaaaaacca   3720

aagctttgtg taaaatcttg aatttatggg gcgggagggt aggaaagcct gtacctgtct   3780

gtttttttcc tgatcctttt ccctcattcc tgaactgcag gagactgagc ccctttgggc   3840

tttggtgacc ccatcactgg ggtgtgttta tttgatggtt gattttgctg tactgggtac   3900

ttcctttccc attttctaat cattttttaa cacaagctga ctcttccctt cccttctcct   3960

ttccctggga aaatacaatg aataaataaa gacttattgg tacgcaaact gtca         4014
```

```
<210> SEQ ID NO 18
<211> LENGTH: 5390
<212> TYPE: DNA
<213> ORGANISM: Mus musculus

<400> SEQUENCE: 18

aagaaggaaa gcacattaga ccatgcgaac taaatttgtg atcgcacaaa atcaagatgt     60

tagactgatg ctgaagatca ctccggtcca aagggaaagt tttcatctct ggagtttgaa    120

gctgagggcc ggtggggcaa catggccgaa ggcggggcaa gcaaaggtga agagccagaa    180

aaactgcccg ggctggcaga ggacgaaccc caggttctgc atggcactgg ccactgtaaa    240

tggttcaacg tgcgcatggg attcggattc atctccatga taagtcgaga gggaaatccc    300

ttggatattc cagtggatgt atttgtacac caaagcaaac tattcatgga aggatttaga    360

agcttgaaag aaggagagcc agtggaattt acatttaaaa aatcccccaa aggccttgag    420

tcaatacggg taacaggccc aggtgggagc ccctgcttag gaagtgaaag aagacctaaa    480

gggaagaccc tgcaaaagag aaagccaaag ggagataggt ggagacggca ggatttactg    540

atggatcaga tgtggactgt gcgagaagaa gagtccagga tgattccaag atgctacaac    600

tgtggtggtc tcgaccatca tgctaaagaa tgcagtctac ctcctcagcc aaagaagtgc    660

cattactgtc agagcatcat gcacatggtg gccaactgcc cacacaagct tgccgctcag    720
```

```
ctgcccgcca gttctcaggg aagacaggag gcagaatccc agccatgcag ctctgcggca    780
ccaagagaag tgggaggggg gcatggctgc acagtactgt ttcctcagga ggtgaagtca    840
gaaatggcag agcactcaga caggtcaccc caagaagttt cttccacgaa agcgtttgca    900
gcaataggag agcaaaacaa aaaggggcct ttgattcaga aacggaaaaa gacttagtac    960
ttgtcagtgt tcccttcacc cgggcgggaa gtctacctca tgcaagcaca ggggaatagt   1020
ggtccacaga gagcagccgg ccgggatgtt aactactgct gaggaactgg gaagttctta   1080
attagacaaa tcactcttaa gcaaactaca tttaagcagg gtgtcatgtt ttatagaatt   1140
gagatactac atatagtatg tgcataagtg agaggggaga cttgaatctg tatgtatgtg   1200
tgaggatttc acataagagt acaggcacac acacacatat atatatacac ttttatatat   1260
ctgtggttgt ctttgtgtgt gtgtgtgtgt gtatgtgtgt gtgtgtgtgt gtgtatgtag   1320
ataaaagcac atactcttcc tcagataatt gggcatctct aagcattgaa aatccatgtg   1380
aagcatttga gatggtttca tagttaaccc ttggaatttt ttctaaatac tacttctttt   1440
atattatgta aaaaatgacc acgtgactgt tacctttcat gtgaaccaaa gcatacttca   1500
gatctcagag ctgccagtca aatggtacta aaggcttttg ggatacttgg tgcctcccaa   1560
gtctgtattc ataactctat cttgatgctg atagagtgtt ttgctgttgc tgttatctgt   1620
cttctcctgt ttgaaggtag taacttaact ctagatgcct ccgactgcca taagctttta   1680
atccttggat acgtagctcc agaaaagaca atgaatgtga acttcctgtg ctgatatttc   1740
agtgtctttt attctgtttg attgtaaatt acatggctat taagaaaaat gaaggggagg   1800
gtaatgtata tagtaacatg gtccttttca gtggtatttt gatgctaggt cttttacaag   1860
ggttctgagg tttttaaggg atggtggcaa cagaagcctc ctttgactaa gtagcttttg   1920
aaccatcact tagatcagga aggtctctta cttactactg aagccttaga gaaaatttta   1980
attatttggg tatattttg gtagctgttt ttatttcccc tggagagtcc tcagacctgt    2040
ttataaaaca aacaaaagca gcatagaaat aaaatagtgg ggcttagaat gaaaattaag   2100
ttgcccaata gatacagccc atgattgata ctaaaaagaa tagtgtttga tggccagcag   2160
agtgaatgag tggagcagag ttaccaaagt gcccactgtt ctgtggctag aaatacttta   2220
tatgataata ttgatgccat ggcaggttcc ttgagtatag aagcggaagt atggtgtgtg   2280
atagattcag gatgagcact cagatcaagt tataggatct tctcagatgg attctcagtt   2340
tgctaagatt ggctaggaac tgattgtagt attgggctgt tttccatcat gttttgtttt   2400
cttttgtttt ttgaatggag ttagcctggt tctaaatgtc atgagcaaac ttttgaaaca   2460
tcttcaagaa ggtaccaagg gattgcagtg cataattttg gctgtaacta tatgggcctg   2520
ttggtataag ctcagataat caaacaagaa agcatcgtga ctcatgagac acattctacg   2580
gaggagtcgc ttcctcctgt gtgtcttgtc atgggagttg ggtggtgcta aggtttcatc   2640
aagccactag aagaagaaag tgtctccgac tagcttacca gtcttttcca gagtagcttg   2700
aattgcttga cagtatttat gagagttcct atagtgtttt acccgaagtg tcagtgtgct   2760
gtaatacaga gcttaccttt gacgatattg aatgtgatgt agccatagag aagtgctgcc   2820
ttgccttacg tgaggatttc aagcttattt aaattatgta gacaaatcaa aggtcatcca   2880
agtataatga gcaaggtaac agttgtacaa gcaaaatatg ataggtcact ctgaacgctc   2940
aaaccaaagt tccttgacta tcaaaatagg aaataatgga cttgaaaact ggacattctg   3000
tttacattta aaatttaaga gctgaggtca ttttaacaaa tgaaagtaga aaattcagaa   3060
```

```
acacttgaat atagacctta tgggtgcagt caacttcttt tcagcatcta accagaccga   3120
cttactaaaa gcacatacca aacctatctt atggttaaaa gtttattttt tatatgaaaa   3180
tagtgtcact attacatgct caggacaaag aactttgctc agggaacata ccatataatg   3240
tttttattgt ttttttttgt tttgttttgt tttgttttgt ttttttacag actaatgtat   3300
aatcctgctt tctcagagca agccaaataa attaagtctt tatgtacgta catatacttg   3360
ttagtaacta cctctgagtt tgacattgat cataattctg aatatcagat attggtcctc   3420
ccttttttaaa tttcatgtca aagtcttgta aagcggaatt ccactacctg cagatgtgaa   3480
ctcactgata tgagcacttg ctcattcaca caagtgaaaa ttctgtttac agcacatggc   3540
tacctcccag ctaccacaga gcacaccttg atgctgctgc agcctgcagg ttgctgataa   3600
ttctctggta cagacgcttt taatctgtag cacagatagg catttgcaac tgcatgtttc   3660
tgaaaaacgc ctgtttttct catagatttc tcatgttaag tagcaaaatc tccaagcatt   3720
tccttagagt tatcatgtat taaatgtaag gaagtatgga cactctaatt tatcctaggc   3780
caaacagaac acagaaacaa tcttgaaaat agctctgtta cctagaggtg aggggcagca   3840
gagataacaa aaggaaactt ggtgtttgta ttttgctgac aagtgttata aaagattcct   3900
accgcttcac ttgtatctct acagtactga aggcaaagca tactgcagca ttccaagcct   3960
caggcacaca actaactagc accagcttgc catgggggaa cttaaagtgc agtgttgcct   4020
tgagccagag gggaacgggg tctgtggagc accactttgc aggggttcct catagtgcgg   4080
tgtggtttga gccatctttt gacctccccc ttacagcaac acaaatgtaa ctcctaaaaa   4140
acgattcact accagccttt agcctgcgaa ctattcgttc tctacacagc aggacacagt   4200
ggacacattt ttatacttgc atttctaatc tttggatgta tttttacaaa tgaaagactt   4260
aggaagattt ttatctgctt atcacctgga aattttagtg tgcaatctaa agaaaaagat   4320
aaagacatca cattattagc atcagtccac ctcccaaata taggatgttt tattgccaat   4380
tatttttgta ttctggctga gctttatttt gcaccagggc aggcctaact tgccgctggt   4440
tgtatgtagt ttgtgaatag aagcccataa gtgttaatag accttgtaac attcgctgta   4500
agatgaatta tacaggatgt ggggaatctc agtaagtctt aaagttaatt taaagtaatt   4560
tatctgtttt ctctaagaaa tgtttatcat aaaatatata tgtaacttcc catttttggta   4620
taaaatctag ggaagtgtgt gcaagtggag ttgtgctgac tttgaatttc tagatgtctt   4680
aatgagattt atttgtttta gaaaaagaac aacttgttga aagcacccag ttctgtctta   4740
catactgtca acagcctctt caagttgtgc ctgtgtgatc tgtgacctcc tgttccttta   4800
aagtgagaca gtgacctatg actcattgtt gaccttatac ttggaacaga actacggcat   4860
ttacggtgga gtcctgtacg acgagaaagt gtcaggatat gcaacgcacc tgtggcttac   4920
cccttgacgg cccagcttgg aaatgatggc accgactacc tcttcaatca cttgtggcta   4980
tcaaccacag gcacttagca ccaggctggc tttaattagt gtgtgttgtt tttgtggtgg   5040
taacaactct atccatatga agaccaaagt gaaccctggt ttctatatgt ctttaatgca   5100
gtgttgtatc tagtatttgg aaattatctc attcagtgtt tagattacct cactccattt   5160
tgattcatgt tgtttacaag tgaacatttt tttaaagata cacttgaaat tgcgttagaa   5220
agaacaaagg aggagttgct attagactgg cacagtgcat tccacagact tggtggactg   5280
ctctctgcag acatgggcct aggactgtct ttgtaccgaa tgtcttactc tgttggctat   5340
tgatgtttaa aatttcatga tagaaaataa aagacacaat gttggtgttt              5390
```

```
<210> SEQ ID NO 19
<211> LENGTH: 5504
<212> TYPE: DNA
<213> ORGANISM: Homo sapiens

<400> SEQUENCE: 19

aattgacaaa gtcacgtgtg ctcagggggc cagaaactgg agagaggaga gaaaaaaatc     60

aaaagaagga aagcacatta gaccatgcga gctaaatttg tgatcgcaca aaatcaagat    120

gttagattga tgcagaagat cactccgttc caaagggaaa gttttcatct cacgagtttg    180

gagctgaggg cccgtggggc aacatggccg aaggcggggc tagcaaaggt ggtggagaag    240

agcccgggaa gctgccggag ccggcagagg aggaatccca ggttttgcgc ggaactggcc    300

actgtaagtg gttcaatgtg cgcatgggat ttggattcat ctccatgata aaccgagagg    360

gaagcccctt ggatattcca gtcgatgtat ttgtacacca aagcaaacta ttcatggaag    420

gatttagaag cctaaaagaa ggagaaccag tggaattcac atttaaaaaa tcttccaaag    480

gccttgagtc aatacgggta acaggacctg gtgggagccc ctgtttagga agtgaaagaa    540

gacccaaagg gaagacacta cagaaaagaa aaccaaaggg agatagatgc tacaactgtg    600

gtggccttga tcatcatgct aaggaatgta gtctacctcc tcagccaaag aagtgccatt    660

actgtcagag catcatgcac atggtggcaa actgcccaca taaaaatgtt gcacagccac    720

ccgcgagttc tcagggaaga caggaagcag aatcccagcc atgcacttca actctccctc    780

gagaagtggg aggcgggcat ggctgtacat caccaccgtt tcctcaggag gctagggcag    840

agatctcaga acggtcaggc aggtcacctc aagaagcttc ctccacgaag tcatctatag    900

caccagaaga gcaaagcaaa aaggggcctt cagttcaaaa aaggaaaaag acataacagg    960

tcttcttcat atgttctttc ctttacccgg ttgcaaagtc tacctcatgc aagtataggg   1020

gaacagtatt tcacaagcag tagctgacct gggattttaa ctactattgg ggaactgtga   1080

atttttaaa cagacaaatc actctaagca aattacattt gagcagggtg tcatgtttta    1140

tgttaattca gagaataaga tactatgtct gtcaatatgt gcatgtgtga gagggagaga   1200

gcctgagtct gtgtgtgtac atgaggattt ttatatagga atgtagacac atatataaag   1260

aggctttgtc tttatatatt tgtgtataga tcaaagcaca caccctctct catataattg   1320

gatatttcca agaattgaaa acccatgtga agcattatag atagttttaa atttaaccca   1380

ctggagtttt cttgaaatac cacttctttt atattatata aaactaaaaa cacgactgtt   1440

acctttgtg tgaaccaaag gatacttcag atctcagagc tgccaattat ggggtactaa    1500

aggtttttaa gacatccagt tctcccgaat ttgggattgc ctctttttct tgaaatctct   1560

ggagtagtaa tttttttccc ccttttttga aggcagtacc ttaacttcat atgcctctga   1620

ctgccataag ctttttgat tctgggataa cataactcca gaaaagacaa tgaatgtgta    1680

atttgggccg atatttcact gttttaaatt ctgtgtttaa ttgtaaaatt agatgcctat   1740

taagagaaat gaaggggagg atcatcttag tggcttgttt tcagtagtat tttaatatca   1800

gcttcttgta accttttcca tgttgtgagg gttgtaaggg attgtgtggc aacagcagct   1860

tcccttggct aactcaatct tctacccatt gcttagagca gggagccctc cttatttact   1920

actgaagacc ttagagaact ccaattgttt ggcatatatt tttggtggtg gtttttattc   1980

ctcctggaga gttatctaat ttgtttctaa aacaaacaag cagcaaagaa atgaattaaa   2040

tactggggtt gagaattaaa attaagtgga tgttcacagt tgcccaatat atatgacctg   2100

caaatgatac gaaaaagtgc agcatttagt ggcagttaac aagagtgaca agcctggggc   2160
```

```
agaggtacca aacctctccc accagagagc tagaagtatt ttatacagta actttgatct   2220
tatggaagtg accttcaatg cttattctga agtaacctat atggtggata caggatgaac   2280
attcagtgcc agggagaatc ttctcaggtt ggttctcgtt agagtgataa actggctagg   2340
ggccatagta ttggtcctgt taggtttcgg tcatggaaaa aaaaattatt ttggggtcat   2400
cctggctcta gatgttatgg gcaaatttct gaaacatctg caagaaggta ccagttaatt   2460
atagtgctta atattgggaa taagattaag cattataatt ataatgtatg ggcctgttgg   2520
tgtaagctca gataattaaa taaaaatagc atgactcaaa tgagacatat tctgctgaac   2580
agtttctact tcctctcccg cctgtcctgt catgggagac gtgtatagtt gctgctgttt   2640
cagcaaacca ccataagacg aaaatgcctc aggttgggtt gccagtcctt tacaactcag   2700
cttgaatttc acaacagtga ttgtgagaat ctgcgtggta tacactgaaa tatcggtgtg   2760
ctgtgatgca aagcttacct ttgacgatat tgaatgtgat atagctgtag agaagtactt   2820
ccttgcctta tgtgaggatt tcaaacttat ttaaattatg tagacaaatc aaagtggcat   2880
tgcttaattt ttagcaggca taataagcaa gttaacagta aaatgcaaaa catgataagc   2940
gttgctcaat ttttagcagg tataataagc aggttaacag taaaaatgca aaacatgata   3000
gataagtcac tttgaaaatt caaaccaaag ttccttcacc ttatggaaat aggaaattat   3060
ggacttcaaa attggacact tcctgtttac aaaaagaaat tcagagctaa aatcatggta   3120
aaaaaaaata gaaacacttg agaactatgg tctttatggg tgcaatttga aatccttttc   3180
atcatcttac cagactaaac taagagcaca taccaaacct atcttatggt tgaaagttgg   3240
ggtttatttt ttatatgaga atattatcac tattacataa catactcagg acaaagaact   3300
ttgctcaggg aacataccat gtaatatttt tgttgtttct ttacagacta gtctacagtc   3360
ctgcttactc aaaacaaacc aaataactta tacctttata taagtattat gtactgatga   3420
tagtaactac ctctgagttt gacacagatc aaaatttttg aatatcagat atcagttatc   3480
ctatttttat ttcatgtgaa aactcctcta aagcagattc cctcaactct gtgcatatgt   3540
gaatatcact gatgtgaaca cattgttcat ttacataggt aaaatattac tctgtttaca   3600
gcaaaaggct acctcatagt tgatacatag cacacctgta tgtatgctgt tccagcctta   3660
caggtggctg ataattctct ggtacagaac ctttttatct gtattataaa tagcaattca   3720
caactgcatg tttctgacaa acacttgtga ataatgaagc atctcgtttt agttagcaaa   3780
gtctccaaac atttccttaa aataatcatg tatttagttt aaagaattat gggcactgtt   3840
caacttaagc aaaacagaac acggaagcag tcttagaagc accactttgc ccagaggtgg   3900
aggttggaag gggtagcagg gagaggggtt ggtgtatgca ggtattcatg ctaggcaaag   3960
agtttaaaag acgccaatgt ccttcattta ctgtctgtgc tgccctgaag ccaagcgtat   4020
tgcagcatta tagccccagg cacataacta actagcactg gcttgccaag gaatgaacat   4080
gcaatgccat tactagctat tgagggaaaa gggtctgtgt gaagcatcac tttgcaggga   4140
ttactaatgg tggggcagca ggtctgtgaa ttaagttatc tcttgacctc accctcatgt   4200
caacacaaat gtaattccta aacaagatgc attgccagtc tcttagccct gtaagctgat   4260
cttttgctac atggcagact ataatgaaaa catttttata cttgggtttc tagtcttcac   4320
tagaaggcct tggatgtatt tttgcagttg aaagatttag aaagattttt acctgcttat   4380
aacttggaag tttagagtgc aatgtaagaa aaaagatcaa gaaatgtcat gttattagca   4440
tcagtccacc tccaatattg ccgatacttt ttttattctg gctcagtttt attttgcacc   4500
agtgcggccc caagttactg ctggttgtat ttagtttgtg aataggagcc cataagtgtt   4560
```

```
aatagacttt gtaacattca ctataagatg aattatacag gacatgggaa atctcattaa   4620
gtcttaaagt taatttaaat taatttatct gttttctcta agaaatgttt atcataaaat   4680
atatatgtgt atttcccctt tggttataaa atttgggaaa gtatgtacaa gtgcagctgc   4740
actgacttta attttctaga tgtcttaatg agatttattt gttttagaga agaacatctt   4800
gttaaaagca tcaaactctg tcttacatag ctgtcaacag cctctttaag atgtggtggt   4860
tgtatgatct gtgtcttaat tgttcagtta gagtgagaag ttgacctatg attcattttt   4920
aaattttata tttggaacaa agctgcaagt tatggtaaag tactgtactg tgagaagtat   4980
tatgatattt aatgcatctg tggcttaaca cttgtgagag ttaccagctt gaaaatgatg   5040
gtgttgacta cctcttgaat cacatctatc aaccactggc acctaccacc aagctggctt   5100
caattagtat gtgttgcttt ttggtattaa caactaaccg tactagagac caaagtgaac   5160
cctgattttt atatgtcttt aataatggtg ttttatctag tgtttttaaa ttatcctgtg   5220
tagtatttag attacctcat tgtccatttt gactcatgtt gtttacaagt gaaaataaaa   5280
acacttgaac tgtatgtttt taaaagacaa aaaaggggta gatgtttgga atgcgtttca   5340
ctcgcatgca gtcatctgga gggactgaag cactgtttgc ctttctgtac actctgggtt   5400
ttatattctc atttcatgcc taatgtctta ttctgtcaat tatggatatg ttgaggttta   5460
aaaaaattac ttgattaaaa ataaaacata taacgttggc attt                    5504
```

<210> SEQ ID NO 20
<211> LENGTH: 20911
<212> TYPE: DNA
<213> ORGANISM: Homo sapiens

<400> SEQUENCE: 20

```
agggatctcc aggctgtcat ggttgctggg aaagatgagg gagggaaagg gggcagagta     60
cggaggcacc aggtcagaaa gacaggagag aattcagaca ggaccaaaac agccagaaaa    120
aataggataa agaaggtaga aaaaaaaaaa aaacaaaaca aaacatgaga agttaaagcc    180
tgggaaatag atacaagaca agaaagagaa atagaaacca agaacaagat tgatgaaagg    240
aggagaagag aaagtagaag gaaaaagaat aagaaagatt ccagacacgc attcaaataa    300
tcctaaatgg ggatgagcag aaagacaagg agaccaaaag aaaagggggg ggggggggtgg    360
tggggaggag aaagaaagga atggaaaaag aaacaaaagg tgaatgtcct gccctgtctg    420
tctggtccaa ccaagaagct agtgtctgcc ctggagggag gaaaggtggg ggagtccagc    480
ctgtctccaa gggactgaca ggcagcttct ggaccagaga ggaactaagc tctcaaagca    540
agctttgggg aggaggaagg gatgggggtg catggtgagt ggagactcct ggaggaagag    600
caagcctcca ctgggttcag cactgccagg gggagagtca gggttcaggg tagcatagca    660
gtgctaatgt atgtacccca gaggggtagg gggtgctagg gcaatttgca ggaggaccac    720
aaacagtaaa ctagagagct acttccctgg gatccgtgat aagaaaatca cttcctcagg    780
tgggagaatt gagcccgaaa gagaatggga gcccttgggg ggcaggcacc tggtcagttt    840
caaagctcgt caatatcaaa agaggctggg atcctgagat caaatgggct ggggcactgg    900
gcagaaacga ggagccattg ccaaactgcc aggatgacca gaacgcccct cccccaggaa    960
aagttcatat atgaacccac ccctgtatga aacttcttaa ttaggtctca tacccccggt   1020
gaatcttgga tgcccttctg tcaacagaat tcccaattta gtgacacctc ggactgaaaa   1080
gagctctgcg gcaaacgggg gtgaaagttt aagagggaat aagcatataa tactcccttg   1140
```

-continued

```
ccagacctca cacatgctga agggaatatt tacagcaaac tggccaaagc aaacgacccc   1200
gcctacccac catcctttta ccctcctccc cgcccttttt gtaaactcca gataaacacc   1260
atttgatcac aaaagggtcg gtttgtcccc tttatagttt gaggcaggca gtgcggcagg   1320
gaaaagtggc gtgggctaag cttccgtctc gggcaaggcc agcttctttg ctggcaccgt   1380
ggcctgggct aaggacagtt gatttggttt tgtttccccc gacccccacc ccgaccccac   1440
ccccacaaag gaacattatt ttcagggtcc tccccccacc cagctttaac actcgcctac   1500
ttgcacccgc actactttaa atgctgcggg cattgcagat agagaggttt ttcagttaat   1560
ttactttttt aattctagag ctacaattaa gtgaaaactc tttttgcgaa aaggtggagg   1620
aatatttcag agacgccaga aattatctgg gtcttttctg acccggaatc tgccctcttt   1680
ctcccttctc ctccccttaa gtcacccttt tctgggactc tgttgaaggg caggctcttt   1740
caacgtctct agtctgtctt ttgttgagtg tgagaccgaa ggaaagagga tcgaggggtc   1800
tgcagagaga aaaagaccgc agatagccgg cagctggcgc ctaatgccgg ggtccgggga   1860
gcgctggcct cgtgggttct cctggaggcc aggcccagca caagccttcg gaacacgctg   1920
gccaatgttt aacccgaatg cagtggccac caggccgctt ttgtttgttc gcaaattaat   1980
cacccagcgc atggccggcg ccagagtggg tttatcaccc accgggaggg gggcgcgccg   2040
ggcacgcaga gacaaagagg agttcgcacc ttcccgcttt tgatcccaga attacggcgg   2100
cctccctgcc taatacgagc ctcctggggc cgagtctggg aggtcagtca taattggcgg   2160
aagtttgcag accattagca agatgtcgac attttcgatt cgaaccccgc aaactttcct   2220
ctcgttctct gcttcgcgcg ctggaggttg gtgtgggaga ggagatgggg gtcagaagta   2280
gcgatctggg gtgatcacag ggttaagtta gagctatggg caaaaaatag gcaattgagg   2340
gaggaggaca gtgtgagggg cagaactccc tctcagtcca cccgcggagc caaaaacaaa   2400
tctagacatt tttaagtaaa atccgcaagc tcccctccca tttccaaagc tgacagctgg   2460
ccagaatgca gaggaatgtc tctctgctgt gcgtgggacg cttgggggca ccgagtgggt   2520
gaggaggagg tcggtcacag tgtggttgta gaactacttt gcttccaccc caagtagtgg   2580
ggcagagatt ggcctgcgag ggcaggcagg caaaaccaga tcgctgggat ttggggccgc   2640
tcttgaaaga gcagcgaagg ggccccaggc cccggaggcg agcagtctgg gggagggggt   2700
gcactttttt tttctatttc tttcttttct tttctttttc ttttttttgg ggcgggggtc   2760
cccagagact catgaaaccc tgcagtgact tccgtgttct gtgtaaggcg ggaaatggcc   2820
tggcctttcg cacccttcag gtggggagga ggggatgcgg gagggggtgt tatgagccaa   2880
cactctgggg caccaccacc tcgtaatttt ccctctctct cctttctcta ttttaaccac   2940
tggcagagac agagaggacg ccagagaaag acagactgaa agggaaagaa aggggcgaga   3000
tggcgagcca gacggagttc gcagaaccac actattctct ctggtgactt cagggaattc   3060
tcaacgctgg cgccaagctc tcttaaccat gtgcgtcaaa aatgcgaggc tggagaagcc   3120
tgtcgcctca aaagatcctc ccctatctca gcgtggttgg cccacaagag cacttcattt   3180
tcacccttcc cttggtgcca cgttggggtt tcggggttgc tgggggttgc gcgggtgcac   3240
aaggcaaaat gcgagagagg cctgtgctgg cctacagaga cacacacatc caaagccctg   3300
agtctcttaa accccctaagc ccccagatca gccctttctc cgttcccttt ccatcgaaga   3360
agctttcatc tcaggaaaga taaaagaaca ttgttttcaa gatttccctc catctaagca   3420
aggatggtcc aagacattgg cccccagaat caagaactgt gggcttaggc gaatcctctg   3480
accccgaccg ggcgctgcgg taacagagtt ggtaattcgg cgattggtaa gatccggtcg   3540
```

```
tttccctccc gtccgcctaa gaggaggccc ccaccctacc cgtactaaaa acagtcaact   3600
cgcctctgag gtgggggcgt ttcacggttt gttttacaaa ttcaccctcc ctccccgact   3660
tctggccaga ttaagtcccc ggggtggaga aagaactgag gcaccgagag ataagtgcga   3720
tgcctagaga agataccagg ctggcgcgcc tcccccaacc caatcgccca ccccttaccc   3780
tgtgctgtgc acccagccgg gcctcgaggt gagggcagcg gcttggaggg gacaggctca   3840
gaacccagtc tctcgctgtg ctcgctttgt ccagatcctc cattctcttc tctacaccca   3900
cacccacatc caggtggaat atgggggccc gcatgcaaat gaaagacgag atccaaaagg   3960
gctggtaaat gcatttcata aaaatcccaa atccatcttc cccaggagct caggcagggc   4020
cagccgcgca ggctgtgtac gtgtttgtgt gtacgtgttt ttcggtgtgt gtttcagtcc   4080
cagtgtgttg gcgcgtgttc gagtacagat acaccggggg tgtttgggta cccgcacatg   4140
gctgcgggtg gggcgcagtg gagaggaagc ccacacatgc gtgtgctgag atatggccgc   4200
atccttgtgc tcccccagcc cagacgcagg ggagaccagc accgagacac ccgagctcgg   4260
gagcccttca gcggcggccg ggcggagctt ggctccacgt ggggctggag agcacgcaag   4320
cctggagtct cggcgctcgc ttctcggctg ccgccggctt ttgtagaacc gagtggccgg   4380
atggcagctc gcggggaggc tcggccaccc gcccggctcg cccggggcgg ggagaagaag   4440
gagagctgga gagagaaccg gccgcggcgg tcggagaggc gagcggagtg caagagaggc   4500
gagcgcccct gcccggcgcc cgggcgcgct ctccgccttc cccgcccggc tcgcctgctc   4560
gctggctccc tccctctctc cctccccctt cctccttggc cctgcctcct ccctcgatcc   4620
ccggctggat gactgaggca tttcagacgt gggctgaacc agagcgagcg agcgagctca   4680
ggggctgcag cgatctctcg ataagccacc tagaggcgac tctgtgcgcg cgcgctcccc   4740
agtggctccc gcccgccctc tgatcatgtt gacatattca caggacaggc agtagtaccg   4800
atgcggcgct gcgacgttac agtttccgac accttctttt tataactcag ctctatcccc   4860
cagcactcga cctgtgaaaa ccacgcctat gcagcaacac aattggtccg aaagcgtcaa   4920
agagccaatc aagaggcctc cggctccccg cagcccacag cgcagcccga ccttctagag   4980
ccgccgagca gacgcccggt gaattctaga ggcggcggag ggtggcgagg agctctcgct   5040
ttctctcgct ccctccctct ccgactccgt ctctctctct ctctctctct ctcccctccc   5100
tctctttccc tctgttccat tttttccccc tctaaatcct ccctgccctg cgcgcctgga   5160
cacagattta ggaagcgaat tcgctcacgt tttaggacaa ggaagagaga gaggcacggg   5220
agaagagccc agcaagattt ggattgaaac cgagacaccc tccggaggct cggagcagag   5280
gaaggaggag gagggcggcg aacggaagcc agtttgcaat tcaagttttg atagcgctgg   5340
tagaaggggg tttaaatcag attttttttt ttttaaagga gagagacttt ttccgctctc   5400
tcgctccctg ttaaagccgg gtctagcaca gctgcagacg ccaccagcga gaaagaggga   5460
gaggaagaca gatagggggc gggggaagaa gaaaaagaaa ggtaaaaagt cttctaggag   5520
aacctttcac atttgcaaca aaagacctag gggctggaga gagattcctg ggacgcaggg   5580
ctggagtgtc tatttcgagc tcagcggcag ggctcgggcg cgagtcgaga ccctgctcgc   5640
tcctctcgct tctgaaaccg acgttcagga gcggcttttt aaaaacgcaa ggcacaagga   5700
cggtcacccg cgcgactatg tttgctgatt tttcgccttg ccctctttaa aagcggcctc   5760
ccattctcca aaagacactt cccctcctcc ctttgaagtg cattagttgt gatttctgcc   5820
tccttttctt ttttctttct tttttgtttt gctttttccc cccttttgaa ttatgtgctg   5880
```

-continued

```
ctgttaaaca acaacaaaaa aacaacaaaa cacagcagct gcggacttgt ccccggctgg   5940
agcccagcgc cccgcctgga gtggatgagc ctctccatga gagatccggt cattcctggg   6000
acaagcatgg cctaccatcc gttcctacct caccgggcgc cggacttcgc catgagcgcg   6060
gtgctgggtc accagccgcc gttcttcccc gcgctgacgc tgcctcccaa cggcgcggcg   6120
gcgctctcgc tgccgggcgc cctggccaag ccgatcatgg atcaattggt gggggcggcc   6180
gagaccggca tcccgttctc ctccctgggg ccccaggcgc atctgaggcc tttgaagacc   6240
atggagcccg aagaagaggt ggaggacgac cccaaggtgc acctggaggc taaagaactt   6300
tgggatcagt ttcacaagcg gggcaccgag atggtcatta ccaagtcggg aaggtaagca   6360
gtgggggcct cctcccctaa gctgttggag agtttttttcc tccctttatt tctctgctcc   6420
cagaacagtc ggttggtcgg ttattacggc ttggacgaaa agttagttcc cctagaaatg   6480
tatgcacaga cttccaggcc ctgccccggt ggcaggaaat ttcagcttac ctgggcatct   6540
gcatgggtct tgcatttggt ctgcatcctg ggttccctcc cgaacagaca gaatttttca   6600
gtggagcaca gacatccctg cagggagcag gaaagaaaaa aaaaaaaggc actctactgc   6660
aagaaactca ctcttcaaac cctcctggaa catccttatt tctttgttga tgttgtgttg   6720
tctgttttat tttgttctca gagagaaaaa cttaaagccc tttccttttg tgtgggtatt   6780
gggaggcctg acaccattcc ccggcccttt ctgccctcca gtctagcctc tgggtctaaa   6840
ggggcctgct gctgccctgg tcagagagaa atcgaagggc attttggttt gtttgcccac   6900
actacttcac gtgtctgtaa cccaagggcg agttcagcag gcaattttgc ataatttaag   6960
attatgtttg cagacttaag gagccagtga ggagacacac accttttttt taatgtgtga   7020
atattatcaa ccatatttta cataatgttt aaaggtcctt gcctgaccaa aacctgcctg   7080
gaagagaaga tcctgtaata gtcatttaaa atcactgatt tttttttgt aatagcattg   7140
aagcctgtaa aggcataaag ttgatacaaa aataaaatcc ccttcatgat atcttaagcg   7200
ttctgtctcc ttccaagcta aatgaggcca aagtttggca taaaatcctc ctcaaactca   7260
caagacattt agtcagtttt ccagcaaagt gcttccttgc ttccttttaa gtcaagacta   7320
cagaatgcca acccttctgt gaaattaaca gcaatgtggt ggcacagtct tgcggttttg   7380
gactggccta agaagtgggg gaatgtgtta gcagctccac gggcagatcg gttatcaggc   7440
ccaggagtgc accgaagtct gcaaaattcg ttctgggaac tcactgaagt ccagtttcac   7500
ttcgcccaca gcgggattgc tattctgcag cagggagggg tgcaacttga cgttcatttc   7560
cttgataagt ttaacatttt ctcatcaatg ggtggtggaa aattctagtc ttaactgacc   7620
gcgctttaca aaaatcttac cccaacctgt ttagatctag atacccacag aaaaagacat   7680
gggcaagaat ttgctctcag gagggcaatc tgtaaagtca agcaaggaca aaaaaaatat   7740
tgaagaaatt gttagacaat gtagagaatt gcagtgccac aatgcatttg ttttgaacct   7800
tgggacgtct aaatatggcg aaactgagaa tatttaatac gttagttgtg gaagaaaacg   7860
attttgcaac cagttgcctc actctgaaac atgtaagctt atcagtcaca atataaagtc   7920
ttagacttgg tttcaatatt atgtgataca taggaaatca aacccaagat tacgggtggt   7980
ttatctttct ttttcttttc tattctttcg ttttataggc gaatgtttcc tccatttaaa   8040
gtgagatgtt ctgggctgga taaaaaagcc aaatacattt tattgatgga cattatagct   8100
gctgatgact gtcgttataa atttcacaat tctcggtgga tggtggctgg taaggccgac   8160
cccgaaatgc caaagaggat gtacattcac ccggacagcc ccgctactgg ggaacagtgg   8220
atgtccaaag tcgtcacttt ccacaaactg aaactcacca acaacatttc agacaaacat   8280
```

```
ggatttgtaa gtttcattgc tctcttcagt aaaattttct cctccttcac tcagtcaaag   8340
gcagtgcttc ccatttcatg agtttcagcc cagacttctc ctttgcttct ccctaagcat   8400
agcaaacttg tcctcgtctg gaaaaaggat tcggggtgtt tctctccaaa taatggaagg   8460
cctggcgttc taaaagaaat ggggcaagaa aacttaccgg cttgtgttct atagcaattc   8520
cagctctttg gtagattcct gacctgagag tgaagttaaa aaccattttt taagagctaa   8580
aatcaatttc aaggctatgt attcctaaag gatttgtttt gttttaaaat atcatacttc   8640
tgttttgaaa ccagtgatat tattttctca ggagagttta cgtttcggag ccttgactct   8700
gttggttaaa tggtgtgaat acatttttaa aaactcgttc ttttactaaa aaaagaattg   8760
ggcttaggtg ggagtccggc ttaccctaaa tgaggcttag atcttcagaa aaaaatggtt   8820
tgtgtgttgg gagtgtatat atggattcag tgacagtgct tagaaactta gaaaactttc   8880
attgcttgta gatatcaggc aaaggacctt ttgcgccttt tcctacccct ccccaacatt   8940
tcaataaaat aaacagcgtg ataagcaagg agtaagcaga aagattaggc ccaggaagac   9000
gcgaatggcg cggaaatatc ttcagcgggc aggaattgca tttgaagccc ttgatttgat   9060
taaggcataa atattcctct ctagagttca gcctttcagg gctttaagtg gattgggctc   9120
gtcaattagt gggcgcttaa agtactgaat cattttgtaa attaaaatgc atgtttttct   9180
ctatctttta agactttggc cttcccaagt gatcacgcta cgtggcaggg gaattatagt   9240
tttggtactc aggtaggcta gggttcaagg tatgaatgat ccttagatgg tgagggtggg   9300
gggggccctt tggcaactga ggagcaattt ggattctcca gaagataaca tctgtggagc   9360
gaaacgtacc cagggggtac tccaaggagg tgggctcggt acaagcgtgg taccctgcgg   9420
tggggaagat ttcagcctgg caggggtcct aagatcccgt ttgttctgct aaatccttgt   9480
tttatgtatg tctcctcttc cctgcccctg cagactatat tgaactccat gcacaaatac   9540
cagccccggt tccacattgt aagagccaat gacatcttga aactccctta tagtacattt   9600
cggacatact tgttccccga aactgaattc atcgctgtga ctgcatacca gaatgataag   9660
gtaaactcaa ggggctttcc tttttaatgg tgatattttg ccttcccctt aaaagctgct   9720
ttaagtcagg atgagaaagt tacaagagag tggagacgag agtcttgagt tgtcttttgt   9780
gatttgtgga gcatttgggg ggaaaggaca atgacacctc gaggagacag aaaaacacct   9840
tgactaggta ggaacaatgc tgagcaaaaa aacgccatac taattttgcc acagagaaac   9900
tcctagaact gctgtcattg atgccaccca ctcctccccc cctcttgggc tttgtcctgt   9960
ctgttttaag gttcatcttc ttccccttgg ggaagaagga tcaagaagtc acattcaaaa  10020
ggaaccagct aaaaatttaa ggcaaaagcc atttgggatc ctgggaggag aatcctagta  10080
gagaccagct tttctcccct agccagaaat cctgagtagc tggtctggtt tttattacct  10140
tttatgctgc tgtgttatga tgtgtgtgtg tgtgtgcatg tgtgtgcatg catgcgtgtg  10200
gttggaaaaa cctaccctga tcacagggtc atattaatcg agttgtctga ggcttttgag  10260
ttggggtggc caaagtcacc acttcatttg aattcccccc ctcccccagg cctgaatctg  10320
gaggttagaa ggatccccaa aagggaaagc acctgatatc tagagctatg gtggcctgaa  10380
ggtcatgggc acagaaaaag tgacccttac tgctgattca ccagttccca gattggctgt  10440
tagcagttat ggggtgggag gagggactga agacccctgc tctgcaatcc tggacttcaa  10500
agagagtcca ttttacctga caacacactt cattttgaac tcactgtcat tgtcactgtc  10560
cttgggtcct ctgtggactt catgatgggg atgttccagc taaatttctt tagtgtgaat  10620
```

-continued

```
accaaaacat gatcttctct ccctgtgaaa cctgaagtct tcaatagagc aatttattcc  10680
aagaacatga atccaaccaa gggtcccccct ttccacctct gagtaactct gtgtatataa  10740
cttcttcttc ccaccaaggg gaagggattt gaaagattac acactatagc atttttctca  10800
aagtgcaaaa tgcatgtgcc ctctagaccc agaatcctgt gaaatgaagt tgttaatgta  10860
ataataaaat gtagcatttt tgatcagaca aaaaggccat gggccttctc cacctaatgg  10920
ccatggcaga gcatataaat gaaaacagat gtttccagtg gtcattcagt actgtaactg  10980
tcaatattgt aatttcctca aaccaccccc caggcaaaga aaaaaaaaat taaactcact  11040
cccgcactca ctcccgcaca agggtagtga aaccccataa atcatttatt ggattcatgg  11100
aaaaggagtg tgtgtgtgtg tgtgtgtgtg tgtgtgtgtg tgtgaaggga gtatgctata  11160
atttatgatt aattgcactg tataaaaatc aaaatgaaag cataatttta agatctacag  11220
gttttccctc ttgatgactt tgacaacact tccatgtcta aacccaaact gttggctgcc  11280
caaagaaaag aatttctttg aataatttca tccccaaatc cctggtttgg cctcatatag  11340
gagatacaag ccctgccaca gtttccttat tatctccttt ccctggcata tctatatgac  11400
ttctgttggc agtcacatct ctagacttgt tgagttggga aaaacaccct caaaacattc  11460
tagaaaatga gaacaatgtc tctgtcttgc ttgtgtctct tccaatagat aacccagtta  11520
aaaatagaca acaacccttt tgcaaaaggt ttccgggaca ctggaaatgg ccgaagagaa  11580
aaaaggtgag ttgaaacaat tatttattag atagtttaga aaaatccctt tttttaggat  11640
ccaactctga agtgttagaa gtgagatgca ggcacttatc ctaagagcgg gtggaaatca  11700
ttcactttcc ccactgctac atgcttgccg ctatcagtat acccaggaca agtacttttc  11760
ctacctcctt acctttaagg aaattaacta ggctacacca tacttatctc tggaagagaa  11820
gcatcaggga taatagatta tacagggatg cctattaatt cctaattaat ttaagttcat  11880
cctaggcagg tcccagaaag aaccatgcca ttgagaaaat acttgggaat ttttgcaatc  11940
ctgtcttcca aataccatca gacagagctg gggacttcgg aaagatgtat ggctctctcc  12000
ctccttcgtg gggacatgta tcattttgca ttacgtagac agctggagag tatatgaaag  12060
agggtctccc ctcccccacc ccctttcaaa gaatttctaa aatccagaaa atcacccccca  12120
aatttttaac ctatcccctt ggggcgggca ttaaaaaaata attgctaaca gctaaatata  12180
tttttattcc aattaatttg ttagtaaaac gattacagta aagtgcagca tgaaataacc  12240
acttcctccc aatcttagcc accatccaaa atttgggtat gctggggaca gacagcgttg  12300
tgtttgcagg attggacacc cggttctccc tatataaggc tggcagtcca gctgtctctg  12360
actagatcca gcctcttctc ctgcttttaa ataaaatttc acagcccaag caaatgcctt  12420
ttcctaatga aaccccatct tgaataaatg caactgaagc ctccttcctt tctccctaac  12480
cctctgccac actcttcagc ccagttagag ggtcaaggac aaagcttggg tctatgtggc  12540
tgccctgggg caagcagatt tcagtgaatt agcgttgtcc ctgggcagca ggcagggtgt  12600
gaggtatgtg tgtgccgctt tggaaagggt aagggaaaca aagaggggaa atgtatgtta  12660
cattctgtaa cctgggtgtg ggcttctgcc acagaaaaca gctcaccctg cagtccatga  12720
gggtgtttga tgaaagacac aaaaaggaga atgggacctc tgatgagtcc tccagtgaac  12780
aagcagcttt caactgcttc gcccaggctt cttctccagc cgcctccact gtagggacat  12840
cgaacctcaa aggtaaacca tgtcaccttt gtgatcactg gactccagtc cctcgtggcc  12900
tggaagagtt gaagggggat ggggcaccaa ccagggcact tgccctttaa aagctagaag  12960
ccttctaaac atccttaaac agaagccaga gttcaaaaag ggctatcagg tgtgtctccc  13020
```

```
cttccccgct aaggcagtag aaggagagca cagaggcctt tctcccagat ccttatttgg  13080
ctggtgggga ggggaggtgg gtgtctgttt gcatactacc tcttggcaag cagctttgaa  13140
aacttgcttg aagcgcttct ctcttttctc tctgtctctg tttctttctc ctcccattct  13200
ctccaaccaa cagaggctcc aactgctgac ttttcactgt ctttgaactc taggttacaa  13260
tgtgttggac tgggtggggg ggaagcaagg gactctgcca cctggaaccg agaaggtggc  13320
ctagaaaaca tccagctata aagcaacaat tgacctggga gaggaggtgg agcactgggg  13380
atctgcggtg ggggtagagc tgggggaggt gggtgaggag tggacaagat ggctcaaatc  13440
ccccctcagt tacctgtgtt taaagagcaa gcagtattta tttggaaaga cacacacaca  13500
cacacacaca cacacacaca cacacacaca ctctcaacgg gaagaaacct gttttttagt  13560
gaaataaaat gcaagtcctt tatgtcttca atccatttaa gctttaaaca taaaatagga  13620
tcccttttc ttttcttctg gtggaacacc cacagagggt gtggtaaaag cgaaaaaaga  13680
atctatgatc gtccccgggc tgtgagccat ctgtccgaca ctcatctctc tctgcaggga  13740
ctggggcaaa tacaaacggt tcaactgagt actggtgttg aaggacaggt gtccgttctg  13800
ccattatcaa ttcagatgtc agggttcttg ccaaacaaat ccttccagag taattcacaa  13860
atttgtggaa ggtgctgctc tctgtcattc actgattttt tgatagtaat tagaatatgt  13920
tccagctgtg agttttaatg ttacttttta cttttaaaaa gttaatttgc aatcgaatgg  13980
ggagatgcat gtgaaatctg ccactgtagg aactcaaaaa aagaagtaaa attcattaaa  14040
ataagaagag ctactgatta ggggattgtc catctaaggg aaagtttaaa ctctgggtaa  14100
atactttaaa ttcataatcg cttattgaat tttccagcaa tgttgttggg cacgattatc  14160
cccattttgc agatgacaac actgaggtgc agagaggcta aggggctttc cccgggatta  14220
cacagccact aagccacgag ctgggattcc aacttgggaa ctggagttcc gttggctcat  14280
actggagata acgcccttct gccttggttt tttccttcgc ctgtggtaga tttatgtccc  14340
agcgagggtg agagcgacgc cgaggccgag agcaaagagg agcatggccc cgaggcctgc  14400
gacgcggcca agatctccac caccacgtcg gaggagccct gccgtgacaa gggcagcccc  14460
gcggtcaagg ctcacctttt cgctgctgag cggccccggg acagcgggcg gctggacaaa  14520
gcgtcgcccg actcacgcca tagccccgcc accatctcgt ccagcactcg cggcctgggc  14580
gcggaggagc gcaggagccc ggttcgcgag ggcacagcgc cggccaaggt ggaagaggcg  14640
cgcgcgctcc cgggcaagga ggccttcgcg ccgctcacgg tgcagacgga cgcggccgcc  14700
gcgcacctgg cccagggccc cctgcctggc ctcggcttcg ccccgggcct ggcgggccaa  14760
cagttcttca acgggcaccc gctcttcctg caccccagcc agtttgccat ggggggcgcc  14820
ttctccagca tggcggccgc tggcatgggt cccctcctgg ccacggtttc tggggcctcc  14880
accggtgtct cgggcctgga ttccacggcc atggcctctg ccgctgcggc gcagggactg  14940
tccggggcgt ccgcggccac cctgcccttc cacctccagc agcacgtcct ggcctctcag  15000
gtatggatcc ttcttcctgc ctccaccagt ctttccacct ttcgtccagt ttccctgtcc  15060
tttgccagca gaccctcacc cgatcccttt ggcctagtag ctgtaataat ttttactgag  15120
ccattaccgg gttcaaggct tagctcatgg agttattatg acttcattct ccccattcac  15180
cccaaaaatc tttaaaattt ttccgaagtt aaaggctgtt tccagcagag tagataggta  15240
gtaacaaaga taacagctgg acacagcact tactttcagg cattcttcta agtgcttgct  15300
ctgtattgac tcatttgacc taacccttca ggggtactat tatcacctcc actttacaga  15360
```

```
tgaaggcgaa gacgcccaga gatgttgagt gacttgtcca aggtcacaca gcgggtacat  15420
ggtggagctg agactcaacc ccaggctatc tgactccagg gcctctttga gggtttctga  15480
ttttagcttc agagctgaca tgtctcttaa gtgtctcata gccaaccctt ccccaggaat  15540
gggactctag gcctggggag gggaagtgac tacttcctga gtaggagttc agtcttgatt  15600
cctccagcct ttcctcccag ttcgaagctc ttctccccac ccccaacccc aagcaggcca  15660
gcctattcct cgaagggtta atggtttgtg cacacgtggg aaatgtcaga ggacagggat  15720
aagcagggac tggggcaggc ctggaggcct gtgtgtggct cagacagctg tgctgggggg  15780
aggtctcagg cggctggaaa caccctgaac tcgatgaaaa ggttctatga ggttttgcat  15840
gctgttgcct tttgttttgt ctgagcacat tcgtctggtc tcccttccct gcgccaagaa  15900
accagattgg cctccccact ccagggagga gggagctgag gaaaggcttg gcttctggca  15960
tttctcaatt cctcccatct cctctgctgg cttctccggg agaccctgtc ctaggtgggc  16020
aggtggttgg tacaccaagg actacctgaa cagacaaaac cttaagggca cctcaaggca  16080
tgatgcagag aactggccca ggccagggtg cctgcatctt aaatgctgct tctgccaatt  16140
cccagcttag tgcactcctg aactcctgcg gcctacctcg gcttctcacc tggaacacca  16200
gtgaatcatg ctggacgatt tctttgtctc tgtttataac aaatgccctt tttccctccc  16260
ccagccccag tttccttttg cttaagatct tcactgtctg tttttttgt tttgttttgt  16320
tttgtttgga gaaacttcta ggattggggt gggaggatgg gggttgggga agaagaaaga  16380
tttaaaaaat tattcctact aatttatgtc ctccggcttc cccttggtta cctctgtggg  16440
gtaaactgaa tctgtatccc catttaacag gtgcaaggag atttcctggg ggctgcacac  16500
actgtgtgca gcatattgca ggctttcact catttaatat ctacaaagtc ctcaataagt  16560
atatgaatta cttatgattt ccctgttttt tcttcctata aggaagctga ggcacaagtt  16620
aatcaaagtc tcttggccta gggtgacaca gctaagattt gtacctagag atttctgagt  16680
gttgacttct ctcctgcccc cacctatctc cccccccaaa aaaaaaaaca caacaacaac  16740
aacaacagaa cataccaggg attcatggct tgcccaatgt tggagggggga gaagagagga  16800
gagggatgag ataagctcct cccacccggc tgactcgctg tgtgtctctt ttctcacccc  16860
agggcctggc catgtcccct ttcggaagcc tgttccctta cccctacacg tacatggccg  16920
cagcggcggc cgcctcctct gcggcagcct ccagctcggt gcaccgccac cccttcctca  16980
atctgaacac catgcgcccg cggctgcgct acagccccta ctccatcccg gtgccggtcc  17040
cggacggcag cagtctgctc accaccgccc tgccctccat ggcggcggcc gcggggcccc  17100
tggacggcaa agtcgccgcc ctggccgcca gcccggcctc ggtggcagtg gactcgggct  17160
ctgaactcaa cagccgctcc tccacgctct cctccagctc catgtccttg tcgcccaaac  17220
tctgcgcgga gaaagaggcg gccaccagcg aactgcagag catccagcgg ttggttagcg  17280
gcttggaagc caagccggac aggtcccgca gcgcgtcccc gtagacccgt cccagacacg  17340
tcttttcatt ccagtccagt tcaggctgcc gtgcactttg tcggatataa aataaaccac  17400
gggcccgcca tggcgttagc ccttcctttt gcagttgcgt ctgggaaggg gccccggact  17460
ccctcgagag aatgtgctag agacagcccc tgtcttcttg gcgtggttta tatgtccggg  17520
atctggatca gattctgggg gctcagaaac gtcggttgca ttgagctact gggggtagga  17580
gttccaacat ttatgtccag agcaacttcc agcaaggctg gtctgggtct ctgcccacca  17640
ggcggggagg tgttcaaaga catctccctc agtgcggatt tatatatata tttttccttc  17700
actgtgtcaa gtggaaacaa aaacaaaatc tttcaaaaaa aaaatcggga caagtgaaca  17760
```

```
cattaacatg attctgtttg tgcagattaa aaactttata gggacttgca ttatcggttc  17820
tcaataaatt actgagcagc tttgtttggg gagggaagtc cctaccatcc ttgtttagtc  17880
tatattaaga aaatctgtgt ctttttaata ttcttgtgat gttttcagag ccgctgtagg  17940
tctcttcttg catgtccaca gtaatgtatt tgtggttttt attttgaacg cttgctttta  18000
gagagaaaac aatatagccc cctacccttt tcccaatcct ttgccctcaa atcagtgacc  18060
caagggaggg ggggatttaa agggaaggag tgggcaaaac acataaaatg aatttattat  18120
atctaagctc tgtagcagga ttcatgtcgt tctttgacag ttctttctct ttcctgtata  18180
tgcaataaca aggttttaaa aaaataataa agaagtgaga ctattagaca aagtatttat  18240
gtaattattt gataactctt gtaaataggt ggaatatgaa tgcttggaaa attaaacttt  18300
aatttattga cattgtacat agctctgtgt aaatagaatt gcaactgtca ggttttgtgt  18360
tcttgttttc ctttagttgg gtttatttcc aggtcacaga attgctgtta acactagaaa  18420
acacacttcc tgcaccaaca ccaataccct ttcaaaagag ttgtctgcaa catttttgtt  18480
ttctttttta atgtccaaaa gtgggggaaa gtgctatttc ctattttcac caaaattggg  18540
gaaggagtgc cactttccag ctccacttca aattccttaa aatataactg agattgctgt  18600
ggggagggag gagggcagag gctgcggttt gactttttaa tttttctttt gttatttgta  18660
tttgctagtc tctgatttcc tcaaaacgaa gtggaattta ctactgttgt cagtatcggt  18720
gttttgaatt ggtgcctgcc tatagagata tattcacagt tcaaaagtca ggtgctgaga  18780
gatggtttaa agacaaattc atgaaggtat attttgtgtt atagttgttg atgagttctt  18840
tggttttctg tatttttccc cctctcttta aaacatcact gaaatttcaa taaattttta  18900
ttgaaatgtc tttgggcctt gtgttaaatg tttttttcttt gggaaccttt cctgaagatg  18960
gacagtcagg ggagggttta gtatcttctt gttctgagtt taccccccttc ccttcgcctt  19020
taaataatta agaccgcccc cagcgaacca aaatgagatg tcactcaagt tacaaagcta  19080
aaaacaaaag tcccttactt gagcgaaggg agccacttca atctgaaatt acttttcctt  19140
taaattaggg agcaaagcag ggagacggaa aggggcctga tgagaataca gaaagaaggg  19200
taatttcaga tacttttaag ttttaatgga aaaagactga tgtgctccct aagtcaggtt  19260
ttcccacccg aatccgacca aaagtaagct cggcaagtac gaatgttttt cgttttaagc  19320
tcgccctcag ttttgacatc aatctggcga atccaagtcg aaaataccttt cttgcaccag  19380
tgtgtttggc tcggggaaaa ggccagcaga atgccccagc agtccgagcg ggcttggcta  19440
ggcagcaacc ctccaggttg tagaagtgga caagacgcaa cgcctttcca ctcggcaacc  19500
ccccacacag cctgcagtcc ctggtgcctc aaattgaacc cggctggccc aaggcgcccc  19560
tacgaggccc catccatccc gagttgtgcg tgcaaagcgc ggccagctcc gcgaaaactt  19620
agctgtgtca cgcgagggag gagggaaatt atccccgaaa ggggaaaggt aattccaggg  19680
tgcacatttc accccctcca cggcaaaagt cacccaggag gctgacatcc tcccctagtc  19740
tcccccttcaa acccgtctcc aggctgttcg gggagttgcc ttttgaagtt caatttatct  19800
ttgaaacatt caataaaaaa tgatgaggca ctgtcagtct tttggtctcc cgaccccccag  19860
cctcgcctcc gaggtgtgtg tctgttgggg ggcgggggcg gcacgggaag gttcgagggt  19920
tagtccttag cccttttctt gccctggggg ccatgacgtg aagacccagc tggagcctgc  19980
ctggcggctg cctccctccc caccccccac ccgccacccc ctggagcccg ccagcccggc  20040
cccaagtccc tgtcaccttc aggcctcttg aatgaccgga gaggaggacg ccccctccct  20100
```

tccctcatcc tgtacttgga agggatcgag gtcgagacct tttggagagc ggggcaaagc 20160
cccttccatc tctggccagg cacgtgggga cccctacagc ctcctctgcg atgtctccgg 20220
gggtgggagg gaagacagac aaccagagta tgttggtgcg gagtcgcggg ggggggggagg 20280 ggcggggtgc gctgcggggg tggcagggcc tgagctgaga cgggccctgg ggacctttga 20340
ggctggggct cccccgagga ctgggagatt tccagggcgc gctccttctg cgcagcggct 20400
acagcctgaa gggggcagct ctggatccag cgacaacgcg cggtgtccgc gcctctgaga 20460
aggtggtagt tggctggttg cgctctcccg aattggggaa aaaagaactc agcctccaaa 20520
agggaagaaa tgctttgctt ttctcttctt tctcagtcca aatttgctta cctcctccct 20580
tctctccccc cgcccccgat ttggggaccc tgctcagact tgtgtccagc ctctcttact 20640
ggcgttcctc ttttttttt tttttttt ttaatctcct gtgtatctca tttgtatatt 20700
gtgatgttaa tgagtaactc ctgtagcgct gatgggcggg gggtggaggg gatgaacggc 20760
tcgcagtctc tctggatttt gctgcctatt actcacctgg cgccggtcgc aatctcgccg 20820
caggctttat ggtggctgcg gccgccccag aggccactca gggcaggcgc cttcgccttt 20880
tttctgggct tcgagtgcca cctatctgtc t 20911

<210> SEQ ID NO 21
<211> LENGTH: 2080
<212> TYPE: DNA
<213> ORGANISM: Homo sapiens

<400> SEQUENCE: 21
ggcctggcca tgtccccttt cggaagcctg ttcccttacc cctacacgta catggccgca 60
gcggcggccg cctcctctgc ggcagcctcc agctcggtgc accgccaccc cttcctcaat 120
ctgaacacca tgcgcccgcg gctgcgctac agcccctact ccatcccggt gccggtcccg 180
gacggcagca gtctgctcac caccgccctg ccctccatgg cggcggccgc ggggcccctg 240
gacggcaaag tcgccgccct ggccgccagc ccggcctcgg tggcagtgga ctcgggctct 300
gaactcaaca gccgctcctc cacgctctcc tccagctcca tgtccttgtc gcccaaactc 360
tgcgcggaga aagaggcggc caccagcgaa ctgcagagca tccagcggtt ggttagcggc 420
ttggaagcca agccggacag gtcccgcagc gcgtccccgt agacccgtcc cagacacgtc 480
ttttcattcc agtccagttc aggctgccgt gcactttgtc ggatataaaa taaaccacgg 540
gcccgccatg gcgttagccc ttccttttgc agttgcgtct gggaaggggc cccggactcc 600
ctcgagagaa tgtgctagag acagcccctg tcttcttggc gtggtttata tgtccgggat 660
ctggatcaga ttctgggggc tcagaaacgt cggttgcatt gagctactgg gggtaggagt 720
tccaacattt atgtccagag caacttccag caaggttggt ctgggtctct gcccaccagg 780
cggggaggtg ttcaaagaca tctccctcag tgcggattta tatatatatt tttccttcac 840
tgtgtcaagt ggaaacaaaa acaaaatctt tcaaaaaaaa aatcgggaca agtgaacaca 900
ttaacatgat tctgtttgtg cagattaaaa actttatagg gacttgcatt atcggttctc 960
aataaattac tgagcagctt tgtttgggga gggaagtccc taccatcctt gtttagtcta 1020
tattaagaaa atctgtgtct ttttaatatt cttgtgatgt tttcagagcc gctgtaggtc 1080
tcttcttgca tgtccacagt aatgtatttg tggtttttat tttgaacgct tgcttttaga 1140
gagaaaacaa tatagccccc taccctttc ccaatccttt gccctcaaat cagtgaccca 1200
agggaggggg ggatttaaag ggaaggagtg ggcaaaacac ataaaatgaa tttattatat 1260
ctaagctctg tagcaggatt catgtcgttc tttgacagtt ctttctcttt cctgtatatg 1320

```
caataacaag gttttaaaaa aataataaag aagtgagact attagacaaa gtatttatgt   1380

aattatttga taactcttgt aaataggtgg aatatgaatg cttggaaaat taaactttaa   1440

tttattgaca ttgtacatag ctctgtgtaa atagaattgc aactgtcagg ttttgtgttc   1500

ttgttttcct ttagttgggt ttatttccag gtcacagaat tgctgttaac actagaaaac   1560

acacttcctg caccaacacc aataccettt caaaagagtt gtctgcaaca tttttgtttt   1620

ctttttaat gtccaaaagt gggggaaagt gctatttcct attttcacca aaattgggga   1680

aggagtgcca ctttccagct ccacttcaaa ttccttaaaa tataactgag attgctgtgg   1740

ggagggagga gggcagaggc tgcggtttga ctttttaatt tttcttttgt tatttgtatt   1800

tgctagtctc tgatttcctc aaaacgaagt ggaatttact actgttgtca gtatcggtgt   1860

tttgaattgg tgcctgccta tagagatata ttcacagttc aaaagtcagg tgctgagaga   1920

tggtttaaag acaaattcat gaaggtatat tttgtgttat agttgttgat gagttctttg   1980

gttttctgta tttttccccc tctctttaaa acatcactga aatttcaata aatttttatt   2040

gaaatgtcta aaaaaaaaaa aaaaaaaaaa aaaaaaaaaa                         2080
```

```
<210> SEQ ID NO 22
<211> LENGTH: 1841
<212> TYPE: DNA
<213> ORGANISM: Homo sapiens

<400> SEQUENCE: 22

gaattctaga ggcggcggag ggtggcgagg agctctcgct ttctctcgct ccctccctct     60

ccgactccgt ccctctctct ctctctctct ctctcccctc cctctctttc cctctgttcc    120

attttttccc cctctaaatc ctccctgccc tgcgcgcctg gacacagatt taggaagcga    180

attcgctcac gttttaggac aaggaagaga gagaggcacg ggagaagagc ccagcaagat    240

ttggattgaa accgagacac cctccggagg ctcggagcag aggaaggagg aggagggcgg    300

cgaacggaag ccagtttgca attcaagttt tgatagcgct ggtagaaggg ggtttaaatc    360

agattttttt ttttttaaa ggagagagac tttttccgct ctctcgctcc ctgttaaagc    420

cgggtctagc acagctgcag acgccaccag cgagaaagag ggagaggaag acagataggg    480

ggcgggggaa gaagaaaaag aaaggtaaaa agtcttctag gagaaccttt cacatttgca    540

acaaaagacc taggggctgg agagagattc ctgggacgca gggctggagt gtctatttcg    600

agctcagcgg cagggctcgg gcgcgagtcg agaccctgct cgctcctctc gcttctgaaa    660

ccgacgttca ggagcggctt tttaaaaacg caaggcacaa ggacggtcac ccgcgcgact    720

atgtttgctg atttttcgcc ttgccctctt taaaagcggc ctcccattct ccaaaagaca    780

cttcccctcc tccctttgaa gtgcattagt tgtgatttct gcctcctttt ctttttttctt    840

tctttttgt tttgcttttt cccccctttt gaattatgtg ctgctgttaa acaacaacaa    900

aaaaacaaca aaacacagca gctgcggact tgtccccggc tggagcccag cgccccgcct    960

ggagtggatg agcctctcca tgagagatcc ggtcattcct gggacaagca tggcctacca   1020

tccgttccta cctcaccggg cgccggactt cgccatgagc gcggtgctgg gtcaccagcc   1080

gccgttcttc cccgcgctga cgctgcctcc caacggcgcg gcggcgctct cgctgccggg   1140

cgccctggcc aagccgatca tggatcaatt ggtgggggcg gccgagaccg gcatcccgtt   1200

ctcctccctg ggccccagg cgcatctgag gcctttgaag accatggagc ccgaagaaga   1260

ggtggaggac gaccccaagg tgcacctgga ggctaaagaa ctttgggatc agtttcacaa   1320
```

```
gcggggcacc gagatggtca ttaccaagtc gggaaggcga atgtttcctc catttaaagt   1380

gagatgttct gggctggata aaaaagccaa atacatttta ttgatggaca ttatagctgc   1440

tgatgactgt cgttataaat ttcacaattc tcggtggatg gtggctggta aggccgaccc   1500

cgaaatgcca aagaggatgt acattcaccc ggacagcccc gctactgggg aacagtggat   1560

gtccaaagtc gtcactttcc acaaactgaa actcaccaac aacatttcag acaaacatgg   1620

atttattata ttgaactcca tgcacaaata ccagccccgg ttccacattg taagagccaa   1680

tgacatcttg aaactccctt atagtacatt tcggacatac ttgttccccg aaactgaatt   1740

catcgctgtg actgcatacc agaatgataa gataacccag ttaaaaatag acaacaaccc   1800

ttttgcaaaa ggtttccggg acactggaaa tggccgaaga g                        1841
```

<210> SEQ ID NO 23
<211> LENGTH: 3515
<212> TYPE: DNA
<213> ORGANISM: Homo sapiens

<400> SEQUENCE: 23

```
gcagggctgg agtgtctatt tcgagctcag cggcagggct cgggcgcgag tcgagaccct     60

gctcgctcct ctcgcttctg aaaccgacgt tcaggagcgg ctttttaaaa acgcaaggca    120

caaggacggt cacccgcgcg actatgtttg ctgatttttc gccttgccct ctttaaaagc    180

ggcctcccat tctccaaaag acacttcccc tcctcccttt gaagtgcatt agttgtgatt    240

tctgcctcct tttcttttt ctttcttttt tgttttgctt tttcccccct tttgaattat    300

gtgctgctgt taaacaacaa caaaaaaaca acaaaacaca gcagctgcgg acttgtcccc    360

ggctggagcc cagcgccccg cctggagtgg atgagcctct ccatgagaga tccggtcatt    420

cctgggacaa gcatggccta ccatccgttc ctacctcacc gggcgccgga cttcgccatg    480

agcgcggtgc tgggtcacca gccgccgttc ttccccgcgc tgacgctgcc tcccaacggc    540

gcggcggcgc tctcgctgcc gggcgccctg gccaagccga tcatggatca attggtgggg    600

gcggccgaga ccggcatccc gttctcctcc ctggggcccc aggcgcatct gaggcctttg    660

aagaccatgg agcccgaaga agaggtggag gacgacccca aggtgcacct ggaggctaaa    720

gaactttggg atcagtttca caagcggggc accgagatgg tcattaccaa gtcgggaagg    780

cgaatgtttc ctccatttaa agtgagatgt tctgggctgg ataaaaaagc caaatacatt    840

ttattgatgg acattatagc tgctgatgac tgtcgttata aatttcacaa ttctcggtgg    900

atggtggctg gtaaggccga ccccgaaatg ccaaagagga tgtacattca cccggacagc    960

cccgctactg gggaacagtg gatgtccaaa gtcgtcactt tccacaaact gaaactcacc   1020

aacaacattt cagacaaaca tggatttact ttggccttcc caagtgatca cgctacgtgg   1080

caggggaatt atagttttgg tactcagact atattgaact ccatgcacaa ataccagccc   1140

cggttccaca ttgtaagagc caatgacatc ttgaaactcc cttatagtac atttcggaca   1200

tacttgttcc ccgaaactga attcatcgct gtgactgcat accagaatga taagataacc   1260

cagttaaaaa tagacaacaa cccttttgca aaaggtttcc gggacactgg aaatggccga   1320

agagaaaaaa gaaaacagct caccctgcag tccatgaggg tgtttgatga aagacacaaa   1380

aaggagaatg ggacctctga tgagtcctcc agtgaacaag cagctttcaa ctgcttcgcc   1440

caggcttctt ctccagccgc ctccactgta gggacatcga acctcaaaga tttatgtccc   1500

agcgagggtg agagcgacgc cgaggccgag agcaaagagg agcatggccc cgaggcctgc   1560

gacgcggcca agatctccac caccacgtcg gaggagccct gccgtgacaa gggcagcccc   1620
```

```
gcggtcaagg ctcacctttt cgctgctgag cggccccggg acagcgggcg gctggacaaa   1680

gcgtcgcccg actcacgcca tagccccgcc accatctcgt ccagcactcg cggcctgggc   1740

gcggaggagc gcaggagccc ggttcgcgag ggcacagcgc cggccaaggt ggaagaggcg   1800

cgcgcgctcc cgggcaagga ggccttcgcg ccgctcacgg tgcagacgga cgcggccgcc   1860

gcgcacctgg cccagggccc cctgcctggc ctcggcttcg ccccgggcct ggcgggccaa   1920

cagttcttca acgggcaccc gctcttcctg caccccagcc agtttgccat ggggggcgcc   1980

ttctccagca tggcggccgc tggcatgggt cccctcctgg ccacggtttc tggggcctcc   2040

accggtgtct cgggcctgga ttccacggcc atggcctctg ccgctgcggc gcagggactg   2100

tccggggcgt ccgcggccac cctgcccttc cacctccagc agcacgtcct ggcctctcag   2160

ggcctggcca tgtccccttt cggaagcctg ttcccttacc cctacacgta catggccgca   2220

gcggcggccg cctcctctgc ggcagcctcc agctcggtgc accgccaccc cttcctcaat   2280

ctgaacacca tgcgcccgcg gctgcgctac agcccctact ccatcccggt gccggtcccg   2340

gacggcagca gtctgctcac caccgccctg ccctccatgg cggcggccgc ggggcccctg   2400

gacggcaaag tcgccgccct ggccgccagc ccggcctcgg tggcagtgga ctcgggctct   2460

gaactcaaca gccgctcctc cacgctctcc tccagctcca tgtccttgtc gcccaaactc   2520

tgcgcggaga aagaggcggc caccagcgaa ctgcagagca tccagcggtt ggttagcggc   2580

ttggaagcca agccggacag gtcccgcagc gcgtccccgt agacccgtcc cagacacgtc   2640

ttttcattcc agtccagttc aggctgccgt gcactttgtc ggatataaaa taaaccacgg   2700

gcccgccatg gcgttagccc ttccttttgc agttgcgtct gggaaggggc cccggactcc   2760

ctcgagagaa tgtgctagag acagcccctg tcttcttggc gtggtttata tgtccgggat   2820

ctggatcaga ttctgggggc tcagaaacgt cggttgcatt gagctactgg gggtaggagt   2880

tccaacattt atgtccagag caacttccag caaggctggt ctgggtctct gcccaccagg   2940

cggggaggtg ttcaaagaca tctccctcag tgcggattta tatatatatt tttccttcac   3000

tgtgtcaagt ggaaacaaaa acaaaatctt tcaaaaaaaa aatccggaca agtgaacaca   3060

ttaacatgat tctgtttgtg cagattaaaa actttatagg gacttgcatt atcggttctc   3120

aataaattac tgagcagctt tgtttgggga gggaagtccc taccatcctt gtttagtcta   3180

tattaagaaa atctgtgtct ttttaatatt cttgtgatgt tttcagagcc gctgtaggtc   3240

tcttcttgca tgtccacagt aatgtatttg tggtttttat tttgaacgct tgcttttaga   3300

gagaaaacaa tatagccccc taccctttc ccaatccttt gccctcaaat cagtgaccca   3360

agggaggggg ggatttaaag ggaaggagtg ggcaaaacac ataaaatgaa tttattatat   3420

ctaagctctg tagcaggatt catgtcgttc tttgacagtt ctttctcttt cctgtatatg   3480

caataacaag gttttaaaaa aaaaaaaaaa aaaaa                              3515
```

<210> SEQ ID NO 24
<211> LENGTH: 2172
<212> TYPE: DNA
<213> ORGANISM: Homo sapiens

<400> SEQUENCE: 24

```
atgagcctct ccatgagaga tccggtcatt cctgggacaa gcatggccta ccatccgttc     60

ctacctcacc gggcgccgga cttcgccatg agcgcggtgc tgggtcacca gccgccgttc    120

ttccccgcgc tgacgctgcc tcccaacggc gcggcggcgc tctcgctgcc gggcgccctg    180
```

```
gccaagccga tcatggatca attggtgggg gcggccgaga ccggcatccc gttctcctcc     240

ctggggcccc aggcgcatct gaggcctttg aagaccatgg agcccgaaga agaggtggag     300

gacgacccca aggtgcacct ggaggctaaa gaactttggg atcagtttca caagcggggc     360

accgagatgg tcattaccaa gtcgggaagg cgaatgtttc ctccatttaa agtgagatgt     420

tctgggctgg ataaaaaagc caaatacatt ttattgatgg acattatagc tgctgatgac     480

tgtcgttata aatttcacaa ttctcggtgg atggtggctg gtaaggccga ccccgaaatg     540

ccaaagagga tgtacattca cccggacagc cccgctactg gggaacagtg gatgtccaaa     600

gtcgtcactt tccacaaact gaaactcacc aacaacattt cagacaaaca tggatttact     660

atattgaact ccatgcacaa ataccagccc cggttccaca ttgtaagagc caatgacatc     720

ttgaaactcc cttatagtac atttcggaca tacttgttcc ccgaaactga attcatcgct     780

gtgactgcat accagaatga taagataacc cagttaaaaa tagacaacaa ccctttttgca    840

aaaggtttcc gggacactgg aaatggccga agagaaaaaa gaaaacagct caccctgcag     900

tccatgaggg tgtttgatga aagacacaaa aaggagaatg ggacctctga tgagtcctcc     960

agtgaacaag cagctttcaa ctgcttcgcc caggcttctt ctccagccgc ctccactgta    1020

gggacatcga acctcaaaga tttatgtccc agcgagggtg agagcgacgc cgaggccgag    1080

agcaaagagg agcatggccc cgaggcctgc gacgcggcca agatctccac caccacgtcg    1140

gaggagccct gccgtgacaa gggcagcccc gcggtcaagg ctcacctttt cgctgctgag    1200

cggccccggg acagcgggcg gctggacaaa gcgtcgcccg actcacgcca tagccccgcc    1260

accatctcgt ccagcactcg cggcctgggc gcggaggagc gcaggagccc ggttcgcgag    1320

ggcacagcgc cggccaaggt ggaagaggcg cgcgcgctcc cgggcaagga ggccttcgcg    1380

ccgctcacgg tgcagacgga cgcggccgcc gcgcacctgg cccagggccc cctgcctggc    1440

ctcggcttcg ccccgggcct ggcgggccaa cagttcttca acgggcaccc gctcttcctg    1500

caccccagcc agtttgccat gggggcgcc ttctccagca tggcggccgc tggcatgggt     1560

cccctcctgg ccacggtttc tggggcctcc accggtgtct cgggcctgga ttccacggcc    1620

atggcctctg ccgctgcggc gcagggactg tccggggcgt ccgcggccac cctgcccttc    1680

cacctccagc agcacgtcct ggcctctcag ggcctggcca tgtccccttt cggaagcctg    1740

ttcccttacc cctacacgta catggccgca gcggcggccg cctcctctgc ggcagcctcc    1800

agctcggtgc accgccaccc cttcctcaat ctgaacacca tgcgcccgcg gctgcgctac    1860

agcccctact ccatcccggt gccggtcccg gacggcagca gtctgctcac caccgccctg    1920

ccctccatgg cggcggccgc ggggcccctg gacggcaaag tcgccgccct ggccgccagc    1980

ccggcctcgg tggcagtgga ctcgggctct gaactcaaca gccgctcctc cacgctctcc    2040

tccagctcca tgtccttgtc gcccaaactc tgcgcggaga aagaggcggc caccagcgaa    2100

ctgcagagca tccagcggtt ggttagcggc ttggaagcca agccggacag gtcccgcagc    2160

gcgtccccgt ag                                                        2172
```

```
<210> SEQ ID NO 25
<211> LENGTH: 2232
<212> TYPE: DNA
<213> ORGANISM: Homo sapiens

<400> SEQUENCE: 25

atgagcctct ccatgagaga tccggtcatt cctgggacaa gcatggccta ccatccgttc      60

ctacctcacc gggcgccgga cttcgccatg agcgcggtgc tgggtcacca gccgccgttc     120
```

```
ttccccgcgc tgacgctgcc tcccaacggc gcggcggcgc tctcgctgcc gggcgccctg    180
gccaagccga tcatggatca attggtgggg gcggccgaga ccggcatccc gttctcctcc    240
ctggggcccc aggcgcatct gaggcctttg aagaccatgg agcccgaaga agaggtggag    300
gacgacccca aggtgcacct ggaggctaaa gaactttggg atcagtttca caagcggggc    360
accgagatgg tcattaccaa gtcgggaagg cgaatgtttc ctccatttaa agtgagatgt    420
tctgggctgg ataaaaaagc caaatacatt ttattgatgg acattatagc tgctgatgac    480
tgtcgttata aatttcacaa ttctcggtgg atggtggctg gtaaggccga ccccgaaatg    540
ccaaagagga tgtacattca cccggacagc cccgctactg gggaacagtg gatgtccaaa    600
gtcgtcactt tccacaaact gaaactcacc aacaacattt cagacaaaca tggatttact    660
ttggccttcc caagtgatca cgctacgtgg caggggaatt atagttttgg tactcagact    720
atattgaact ccatgcacaa ataccagccc cggttccaca ttgtaagagc caatgacatc    780
ttgaaactcc cttatagtac atttcggaca tacttgttcc ccgaaactga attcatcgct    840
gtgactgcat accagaatga taagataacc cagttaaaaa tagacaacaa ccccttttgca    900
aaaggtttcc gggacactgg aaatggccga agagaaaaaa gaaaacagct caccctgcag    960
tccatgaggg tgtttgatga aagacacaaa aaggagaatg ggacctctga tgagtcctcc   1020
agtgaacaag cagctttcaa ctgcttcgcc caggcttctt ctccagccgc ctccactgta   1080
gggacatcga acctcaaaga tttatgtccc agcgagggtg agagcgacgc cgaggccgag   1140
agcaaagagg agcatggccc cgaggcctgc gacgcggcca agatctccac caccacgtcg   1200
gaggagccct gccgtgacaa gggcagcccc gcggtcaagg ctcacctttt cgctgctgag   1260
cggccccggg acagcgggcg gctggacaaa gcgtcgcccg actcacgcca tagccccgcc   1320
accatctcgt ccagcactcg cggcctgggc gcggaggagc gcaggagccc ggttcgcgag   1380
ggcacagcgc cggccaaggt ggaagaggcg cgcgcgctcc cgggcaagga ggccttcgcg   1440
ccgctcacgg tgcagacgga cgcggccgcc gcgcacctgg cccagggccc cctgcctggc   1500
ctcggcttcg ccccgggcct ggcgggccaa cagttcttca acgggcaccc gctcttcctg   1560
caccccagcc agtttgccat ggggggcgcc ttctccagca tggcggccgc tggcatgggt   1620
cccctcctgg ccacggtttc tggggcctcc accggtgtct cgggcctgga ttccacggcc   1680
atggcctctg ccgctgcggc gcagggactg tccggggcgt ccgcggccac cctgcccttc   1740
cacctccagc agcacgtcct ggcctctcag ggcctggcca tgtccccttt cggaagcctg   1800
ttcccttacc cctacacgta catggccgca gcggcggccg cctcctctgc ggcagcctcc   1860
agctcggtgc accgccaccc cttcctcaat ctgaacacca tgcgcccgcg gctgcgctac   1920
agcccctact ccatcccggt gccggtcccg gacggcagca gtctgctcac caccgccctg   1980
ccctccatgg cggcggccgc ggggccccctg gacggcaaag tcgccgccct ggccgccagc   2040
ccggcctcgg tggcagtgga ctcgggctct gaactcaaca gccgctcctc cacgctctcc   2100
tccagctcca tgtccttgtc gcccaaactc tgcgcggaga aagaggcggc caccagcgaa   2160
ctgcagagca tccagcggtt ggttagcggc ttggaagcca agccggacag gtcccgcagc   2220
gcgtccccgt ag                                                       2232
```